(12) United States Patent
Alper et al.

(10) Patent No.: US 8,153,671 B2
(45) Date of Patent: Apr. 10, 2012

(54) HETEROTETRACYCLIC COMPOUNDS AS TPO MIMETICS

(75) Inventors: Phillip B. Alper, San Diego, CA (US); Thomas Marsilje, San Diego, CA (US); Arnab Chatterjee, San Diego, CA (US); Wenshuo Lu, San Diego, CA (US); Daniel Mutnick, San Diego, CA (US); Michael Roberts, Pomona, CA (US); Yun He, Shanghai (CN)

(73) Assignee: IRM LLC, Hamilton (BM)

( * ) Notice: Subject to any disclaimer, the term of this patent is extended or adjusted under 35 U.S.C. 154(b) by 986 days.

(21) Appl. No.: 11/995,683

(22) PCT Filed: Jul. 14, 2006

(86) PCT No.: PCT/US2006/027691
§ 371 (c)(1),
(2), (4) Date: May 29, 2008

(87) PCT Pub. No.: WO2007/009120
PCT Pub. Date: Jan. 18, 2007

(65) Prior Publication Data
US 2009/0075996 A1    Mar. 19, 2009

Related U.S. Application Data

(60) Provisional application No. 60/699,481, filed on Jul. 14, 2005.

(51) Int. Cl.
*A61K 31/404* (2006.01)
*C07D 487/02* (2006.01)

(52) U.S. Cl. ............ 514/382; 548/252; 548/266.4; 548/421; 514/383; 514/410

(58) Field of Classification Search ............ 514/382, 514/383, 410; 548/252, 266.4, 421
See application file for complete search history.

(56) References Cited

U.S. PATENT DOCUMENTS

| 4,830,944 | A | 5/1989 | Umehara |
| 6,040,331 | A | 3/2000 | Yamamoto |
| 6,288,099 | B1 | 9/2001 | Antane |

FOREIGN PATENT DOCUMENTS

| EP | 404536 | 12/1990 |
| JP | 62056471 | 3/1987 |
| JP | 63148267 | 6/1988 |
| JP | 6228554 | 8/1994 |
| JP | 11322756 | 11/1999 |
| WO | WO9015799 | 12/1990 |
| WO | WO0034285 | 6/2000 |
| WO | WO0042040 | 7/2000 |
| WO | WO0139773 | 6/2001 |
| WO | WO2004054515 | 7/2004 |

OTHER PUBLICATIONS

Buu-Hui et al, Carcinogenic Nitrogen Compounds. Part XXXIV. J. Chem. Soc. (1962), pp. 2630-2632.*
Buu-Hui et al, Carcinogenic Nitrogen Compounds. Part XXXVI. J. Chem. Soc. (1963), pp. 2274-2279.*
Butera, JA et al., Synthesis and Potassium Channel Opening Activity of Substituted 10H-Benzo[4,5]furo[3,2-b]indole- and 5,10-Dihydro-indeno[1,2-b]indole-1-carboxylic Acids, Bioorganic & Medicinal Chemistry Letters, 2001, 2093-2097, 11.
Tidwell, R.R. and Geratz, J.D., Diarylamidine Derivatives with One or Both of the Aryl Moieties Consisting of an Indole or Indole-like Ring, Inhibitors of Arginine-Specific Esteroproteases, Journal of Medicinal Chemistry, 1978, 613-623, 21 (7).
De Clercq E. and Dann, O., Diaryl Amidine Derivatives as Oncornaviral DNA Polymerase Inhibitors, Journal of Medicinal Chemistry, 1980, 787-795, 23.
Buu-Hoi N.P. et al, Carcinogenic Nitrogen Compounds. Part XXXIV. J. Chem. Soc. (1962), pp. 2630-2632.
Buu-Hoi N.P. et al, Carcinogenic Nitrogen Compounds. Part XXXVI. J. Chem. Soc. (1963), pp. 2274-2279.

* cited by examiner

*Primary Examiner* — Kamal Saeed
*Assistant Examiner* — Janet L Coppins
(74) *Attorney, Agent, or Firm* — Daniel E. Raymond; Genomics Institute of the Novartis Research Foundation

(57) ABSTRACT

The invention provides a novel class of compounds, pharmaceutical compositions comprising such compounds and methods of using such compounds to treat or prevent diseases or disorders associated with abnormal or deregulated TPO activity, particularly diseases or disorders that involve thrombocytopenia.

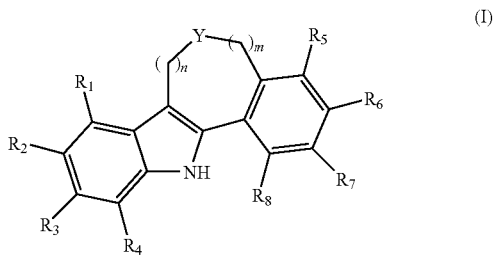

10 Claims, No Drawings

HETEROTETRACYCLIC COMPOUNDS AS TPO MIMETICS

CROSS-REFERENCE TO RELATED APPLICATIONS

This application claims the benefit of priority to U.S. Provisional Application No. 60/699,481, filed 14 Jul. 2005. The full disclosure of this application in incorporated herein by reference in its entirety and for all purposes.

BACKGROUND OF THE INVENTION

1. Field of the Invention

The invention provides a novel class of compounds, pharmaceutical compositions comprising such compounds and methods of using such compounds to treat or prevent diseases or disorders associated with abnormal or deregulated TPO activity, particularly diseases or disorders that involve thrombocytopenia.

2. Background

Megakaryocytes are bone marrow-derived cells, which are responsible for producing circulating blood platelets. Thrombopoietin (TPO), a hematopoietic cytokine, supports the process of cellular proliferation and differentiation of hematopoietic stem cells and is necessary for the regulation of megakaryocytes.

The novel compounds of this invention, as TPO mimetics, are useful in treating diseases or conditions that anticipate and/or result in a decrease in blood or blood platelets including, but not limited to, radiation therapy, chemotherapy, immune therapy, cancers, viral infections, and transplants such as bone marrow and stem cell transplants.

SUMMARY OF THE INVENTION

In one aspect, the present invention provides compounds of Formula I:

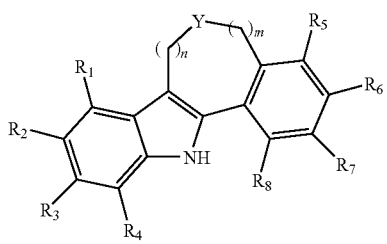

in which:

n is selected from 0, 1, 2 and 3;

m is selected from 0 and 1;

Y is selected from $CR_9R_{10}$, $NR_9$, O and $S(O)_2$; wherein $R_9$ and $R_{10}$ are independently selected from hydrogen and $C_{1-6}$alkyl;

$R_1$ is selected from hydrogen, halo, cyano, nitro, $NR_9R_{10}$, $C_{1-6}$alkyl, $C_{1-6}$alkoxy, halo-substituted-$C_{1-6}$alkoxy, halo-substituted-$C_{1-6}$alkyl, $C_{3-12}$cycloalkyl and $C_{3-8}$heterocycloalkyl; wherein $R_9$ and $R_{10}$ are independently selected from hydrogen and $C_{1-6}$alkyl;

$R_2$ and $R_3$ are independently selected from halo, cyano, $C_{1-6}$alkyl, $C_{2-6}$alkenyl, $C_{2-6}$alkynyl, halo-substituted-$C_{1-6}$alkyl, $C_{6-10}$aryl, $C_{1-10}$heteroaryl, $C_{3-8}$heterocycloalkyl and $C_{3-12}$cycloalkyl; wherein any alkyl, alkenyl, alkynyl, aryl, heteroaryl, cycloalkyl or heterocycloalkyl of $R_2$ or $R_3$ is optionally substituted by 1 to 3 radicals independently selected from halo, $C_{1-6}$alkyl, $C_{1-6}$alkoxy, cyano-$C_{1-6}$alkyl, hydroxy-$C_{1-6}$alkyl, halo-substituted-$C_{1-6}$alkyl, halo-substituted-$C_{1-6}$alkoxy, $-NR_{12}R_{13}$, $-XOR_{13}$, $-S(O)_2R_{13}$, $C_{3-12}$cycloalkyl, $C_{3-8}$heterocycloalkyl, $C_{6-10}$aryl and $C_{1-10}$heteroaryl; wherein X is a bond or $C_{1-6}$alkylene and $R_{12}$ and $R_{13}$ are independently selected from $C_{1-6}$alkyl, cyano-$C_{1-6}$alkyl, hydroxy-$C_{1-6}$alkyl, halo-substituted-$C_{1-6}$alkyl and halo-substituted-$C_{1-6}$alkoxy; wherein any aryl, heteroaryl, cycloalkyl and heterocycloalkyl substituents of $R_2$ and $R_3$ are optionally further substituted with 1 to 3 radicals independently selected from halo, $C_{1-6}$alkyl, $C_{1-6}$alkoxy, cyano-$C_{1-6}$alkyl, hydroxy-$C_{1-6}$alkyl, halo-substituted-$C_{1-6}$alkyl and halo-substituted-$C_{1-6}$alkoxy;

$R_4$ is selected from hydrogen, halo, cyano, nitro, $XNR_9R_{10}$, $OXNR_9R_{10}$, $C_{1-6}$alkyl, $C_{1-6}$alkoxy, halo-substituted-$C_{1-6}$alkoxy, halo-substituted-$C_{1-6}$alkyl, $C_{3-12}$cycloalkyl, $C_{3-8}$heterocycloalkyl, $C_{6-10}$aryl and $C_{1-10}$heteroaryl; wherein X is a bond or $C_{1-6}$alkylene and $R_9$ and $R_{10}$ are independently selected from hydrogen and $C_{1-6}$alkyl;

$R_5$, $R_6$ and $R_7$ are independently selected from hydrogen, $C_{1-6}$alkyl, $C_{3-8}$heterocycloalkyl, $C_{1-10}$heteroaryl, $C_{6-10}$aryl, $OS(O)_2R_{11}$, $NR_{11}S(O)_2R_{14}$, $NR_{11}C(O)R_{14}$, $NR_{11}C(O)NR_{11}R_{14}$, $NR_{11}C(O)C(O)OR_{14}$, $NR_{11}C(O)OR_{14}$, $OC(O)NR_{11}R_{14}$, $C(O)OR_{11}$, $C(O)R_{15}$, $NR_{11}R_{14}$, $NR_{11}R_{15}$ and $C(O)NR_{11}R_{14}$; wherein $R_{11}$ and $R_{14}$ are independently selected from hydrogen, $C_{1-6}$alkyl, halo-substituted-$C_{1-6}$alkyl, $C_{1-6}$alkoxy, cyano-$C_{1-6}$alkyl, hydroxy-$C_{1-6}$alkyl and $C_{1-6}$alkyl substituted with $NR_9R_{10}$; $R_{15}$ is $C_{3-8}$heterocycloalkyl optionally substituted with 1 to 3 $C_{1-6}$alkyl radicals; wherein any aryl, heterocycloalkyl or heteroaryl of $R_5$, $R_6$ and $R_7$ can be optionally further substituted with 1 to 3 radicals independently selected from halo, $C_{1-6}$alkyl, $C_{1-6}$alkoxy, cyano-$C_{1-6}$alkyl, hydroxy-$C_{1-6}$alkyl, halo-substituted-$C_{1-6}$alkyl, halo-substituted-$C_{1-6}$alkoxy, $OS(O)_2R_{11}$, $NR_{11}S(O)_2R_{14}$, $NR_{11}C(O)R_{14}$, $NR_{11}C(O)NR_{11}R_{14}$, $NR_{11}C(O)C(O)OR_{14}$, $NR_{11}C(O)OR_{14}$, $OC(O)NR_{11}R_{14}$, $C(O)OR_{11}$, $C(O)R_{15}$, $NR_{11}R_{14}$, $NR_{11}R_{15}$ and $C(O)NR_{11}R_{14}$; wherein $R_{11}$, $R_{14}$ and $R_{15}$ are as defined above;

$R_8$ is selected from hydrogen, halo, cyano, $C_{1-6}$alkoxy, halo-substituted-$C_{1-6}$alkyl, halo-substituted-$C_{1-6}$alkoxy and $C_{1-6}$alkyl; and the N-oxide derivatives, prodrug derivatives, protected derivatives, individual isomers and mixture of isomers thereof, and the pharmaceutically acceptable salts and solvates (e.g. hydrates) of such compounds.

In a second aspect, the present invention provides a pharmaceutical composition which contains a compound of Formula I or a N-oxide derivative, individual isomers and mixture of isomers thereof; or a pharmaceutically acceptable salt thereof, in admixture with one or more suitable excipients.

In a third aspect, the present invention provides a method of treating a disease or condition in an animal in which increased blood platelet levels, can inhibit or ameliorate the pathology and/or symptomology of the disease or condition, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides the use of a compound of Formula I in the manufacture of a medicament for treating a disease or condition in an animal in which decreased blood platelet levels, contributes to the pathology and/or symptomology of the disease or condition.

In a fifth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

DETAILED DESCRIPTION OF THE INVENTION

Definitions

"Alkyl" as a group and as a structural element of other groups, for example halo-substituted-alkyl and alkoxy, can be either straight-chained or branched. $C_{1-4}$-alkoxy includes, methoxy, ethoxy, and the like. Halo-substituted alkyl includes trifluoromethyl, pentafluoroethyl, and the like.

"Aryl" means a monocyclic or fused bicyclic aromatic ring assembly containing six to ten ring carbon atoms. For example, aryl may be phenyl or naphthyl, preferably phenyl. "Arylene" means a divalent radical derived from an aryl group.

"Heteroaryl" is as defined for aryl above where one or more of the ring members is a heteroatom. For example $C_{1-10}$heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc.

"Heterocycloalkyl" means cycloalkyl, as defined in this application, provided that one or more of the ring carbons indicated, are replaced by a moiety selected from —O—, —N=, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes morpholino, pyrrolidinyl, pyrrolidinyl-2-one, piperazinyl, piperidinyl, piperidinylone, 1,4-dioxa-8-aza-spiro[4.5]dec-8-yl, etc.

"Halogen" (or halo) preferably represents chloro or fluoro, but may also be bromo or iodo.

"Thrombopoietin (TPO)" is also known in the art as c-Mpl ligand, mpl ligand, megapoietin, and megakaryocyte growth and development factor.

"Treat", "treating" and "treatment" refer to a method of alleviating or abating a disease and/or its attendant symptoms.

DESCRIPTION OF THE PREFERRED EMBODIMENTS

The present invention provides compounds, compositions and methods for the treatment of thrombocytopenia. Thrombocytopenia can be broadly interpreted as any decrease in the number of blood platelets below what is considered normal or desired for a healthy individual.

In one embodiment, with reference to compounds of Formula I, n is selected from 0, 1 and 2;

Y is selected from $CR_9R_{10}$, O and $S(O)_2$; wherein $R_9$ and $R_{10}$ are independently selected from hydrogen and $C_{1-6}$alkyl;

$R_1$ is selected from hydrogen, $C_{1-6}$alkyl and halo-substituted-$C_{1-6}$alkyl;

$R_2$ is selected from halo, $C_{6-10}$aryl, $C_{1-6}$alkyl and $C_{2-6}$alkenyl; wherein any aryl of $R_2$ is optionally substituted by 1 to 3 radicals independently selected from halo, $C_{1-6}$alkyl and $C_{1-6}$alkoxy;

$R_3$ is selected from halo, hydroxy, cyano, $C_{1-6}$alkyl, $C_{2-6}$alkenyl, halo-substituted-$C_{1-6}$alkyl, $C_{6-10}$aryl and $C_{1-10}$heteroaryl; wherein any aryl or heteroaryl of $R_3$ is optionally substituted by 1 to 3 radicals independently selected from halo, $C_{1-6}$alkyl, $C_{1-6}$alkoxy, cyano-$C_{1-6}$alkyl, halo-substituted-$C_{1-6}$alkyl, halo-substituted-$C_{1-6}$alkoxy, —$NR_{12}R_{13}$, —$XOR_{13}$, —$S(O)_2R_{13}$ and $C_{3-8}$heterocycloalkyl; wherein X is a bond or $C_{1-6}$alkylene and $R_{12}$ and $R_{13}$ are independently selected from hydrogen and $C_{1-6}$alkyl;

$R_4$ is selected from hydrogen and halo;

$R_5$ is selected from hydrogen and $C_{1-6}$alkyl;

$R_6$ is selected from $C_{1-10}$heteroaryl, $OS(O)_2R_{11}$, $NR_{11}$, $S(O)_2R_{14}$, $NR_{11}C(O)R_{14}$, $NR_{11}C(O)OR_{14}$, $C(O)OR_{11}$, $R_{15}$, $NR_{11}R_{14}$ and $C(O)NR_{11}R_{14}$; wherein $R_{11}$, and $R_{14}$ are independently selected from hydrogen, $C_{1-6}$alkyl, hydroxy-$C_{1-6}$alkyl and halo-substituted-$C_{1-6}$alkyl; $R_{15}$ is $C_{3-8}$heterocycloalkyl optionally substituted with 1 to 3 $C_{1-6}$alkyl radicals;

$R_7$ is selected from hydrogen, hydroxyl, $NR_{11}S(O)_2R_{14}$ and $NR_{11}R_{14}$; wherein $R_{11}$ and $R_{14}$ are as defined above; and $R_8$ is selected from hydrogen and $C_{1-6}$alkyl.

In another embodiment, n is selected from 0 and 1; and Y is selected from $CR_9R_{10}$, O and $S(O)_2$; wherein $R_9$ and $R_{10}$ are independently selected from hydrogen and methyl.

In another embodiment, $R_1$ is selected from hydrogen and trifluoromethyl; and $R_2$ is selected from hydrogen, bromo, chloro, iodo, allyl, trifluoromethyl, and phenyl optionally substituted with 1 to 3 radicals independently selected from methyl and ethyl.

In another embodiment, $R_3$ is selected from hydrogen, bromo, chloro, cyano, trifluoromethyl, allyl, pyrimidinyl, pyridinyl, piperidinyl, benzoxazolyl, thiazolyl and phenyl; wherein said pyrimidinyl, thiazolyl and phenyl are optionally substituted by 1 to 3 radicals independently selected from chloro, fluoro, methyl, ethyl, propyl, butyl, iso-butyl, t-butyl, isopropoxy, propoxy, methoxy, dimethyl-amino, methoxymethyl, hydroxy, cyclohexyl, pyridinyl, methylsulfonyl, ethylsulfonyl, morpholino, diethylamino, pyrazinyl, piperidinyl, phenyl, trifluoromethyl, hexanyl and cyano-methyl.

In another embodiment, $R_4$ is selected from hydrogen, fluoro and bromo.

In another embodiment, $R_5$ and $R_8$ are both hydrogen.

In another embodiment, $R_6$ is selected from amino, ureido, hydroxy-acetyl-amino, carboxyl, methoxycarbonyl, methoxycarbonyl-amino, 4H-[1,2,4]oxadiazol-5-one, tetrazolyl, methyl-aminocarbonyl, dimethyl-aminocarbonyl, methyl-carbonyl-amino, morpholino-carbonyl, methyl-piperazinyl-carbonyl, cyano, tetrazolyl, amino-carbonyl, methyl-sulfonyl-amino, methyl-sulfonyl-amino-carbonyl, t-butoxy-carbonyl-amino, hydroxy-carbonyl-methyl-amino, hydroxy-methyl-carbonyl-amino, oxalyl-amino and trifluoromethyl-sulfonyloxy.

In another embodiment, $R_7$ is selected from hydrogen, hydroxyl, methyl-carbonyl-amino, amino and amino-carbonyl.

In another embodiment are compounds detailed in the Examples and Tables, infra.

Pharmacology and Utility

Thrombocytopenia can be broadly interpreted as any decrease in the number of blood platelets below what is considered normal or desired for a healthy individual. Thrombocytopenia is known to have many causative factors, including but not limited to, radiation therapy, chemotherapy, immune therapy, immune thrombocytopenic purpura, myelodysplastic syndrome (MDS), aplastic anemia, AML, CML, viral infections (including, but not limited to; HIV, hepatitis C, parvovirus) liver disease, myeloablation, bone marrow transplant, stem cell transplant, peripheral blood stem cell transplant, progenitor cell defect, polymorphisms in stem cells and progenitor cells, defects in TPO, neutropenia, dendritic cell mobilization, proliferation, activation or differentiation.

TPO has significant therapeutic value in the treatment of patients with reduced platelet count. In particular patients with many types of cancer suffer thrombocytopenias because of myelosuppressive chemotherapy or radiation therapy which can cause an increase in the risk of bleeding and often limits the dose of chemotherapeutic agents that may be given to receiving intensive chemotherapy or bone marrow transplantation.

The compounds of this invention are useful in treating thrombocytopenia regardless of the factor or factors causing the condition. The compounds of this invention are also useful in treating thrombocytopenia when the causative factor or factors of the condition are unknown or have yet to be identified. The compounds of this invention are useful whenever a decrease in blood or blood platelets is anticipated including, but not limited to, transplant surgery, surgery, anesthesia prior to child birth and gut protection.

Because platelets (thrombocytes) are necessary for blood clotting and when their numbers are very low a patient is at risk of death from catastrophic hemorrhage, TPO mimetics of the invention have a useful application in the treatment of various hematological disorders, for example, diseases primarily due to platelet defects.

In accordance with the foregoing, the present invention further provides a method for preventing or treating any of the diseases or disorders described above in a subject in need of such treatment, which method comprises administering to said subject a therapeutically effective amount (See, "Administration and Pharmaceutical Compositions", infra) of a compound of Formula I or a pharmaceutically acceptable salt thereof. For any of the above uses, the required dosage will vary depending on the mode of administration, the particular condition to be treated and the effect desired.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with one or more therapeutic agents (pharmaceutical combinations). The TPO mimetic compounds of the current invention are also useful in acting on cells for survival or proliferation in conjunction with other agents known to act on cells for survival or proliferation. Such other agents include but are not limited to: G-CSF, GM-CSF, TPO, M-CSF, EPO, Gro-beta, IL-11, SCF, FLT3 ligand, LIF, IL-3, IL-6, IL-1, Progenipoietin, NESP, SD-01, or IL-5 or a biologically active derivative of any of the aforementioned agents.

Human dendritic cells have been shown to express the TPO receptor and TPO is a potent mobilizer of dendritic cells. The TPO mimetic compounds of the current invention are also useful as a vaccine adjuvant in that they increase the activity and mobility of dendritic cells. The pharmaceutically active compounds of this invention are useful as an immunological adjuvant, given in combination with an orally, transdermally or subcutaneously delivered vaccine and/or immunomodulator, by increasing the activity and mobility of dendritic cells.

TPO is known to have various effects including anti-apoptotic/survival effects on megakaryocytes, platelets and stem cells, and proliferative effects on stem cells and megakaryocytic cells. Therefore TPO and/or TPO mimetics of the invention, effectively increase the number of stem and progenitor cells so that there is synergistic effects when TPO is used in conjunction with other cytokines that induce differentiation.

Where the compounds of the invention are administered in conjunction with other therapies, dosages of the co-administered compounds will of course vary depending on the type of co-drug employed, on the specific drug employed, on the condition being treated and so forth.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I can be prepared by proceeding as in the following Reaction Scheme I:

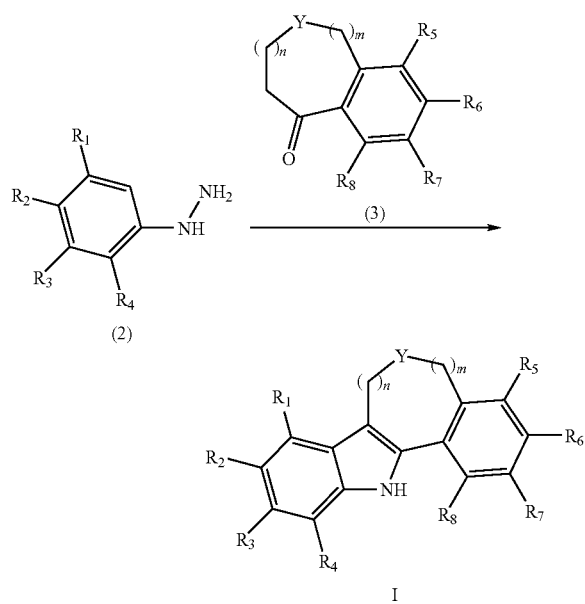

in which n, m, Y and $R_1$ to $R_8$ are as defined in the Summary of the Invention. A compound of Formula I can be synthesized by reacting a compound of formula 2 with a compound of formula 3 in the presence of a suitable Lewis acid (for example, Zinc chloride, and the like) or protic acid (for example, HCl, and the like) and a suitable solvent (for example, acetic acid, ethanol, and the like). The reaction proceeds in a temperature range of about 80° C. to about 120° C. and can take up to about 24 hours to complete.

Detailed examples of the synthesis of a compound of Formula I can be found in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3$^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diasteromeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) that of reaction scheme I; and
(b) optionally converting a compound of the invention into a pharmaceutically acceptable salt;
(c) optionally converting a salt form of a compound of the invention to a non-salt form;
(d) optionally converting an unoxidized form of a compound of the invention into a pharmaceutically acceptable N-oxide;
(e) optionally converting an N-oxide form of a compound of the invention to its unoxidized form;
(f) optionally resolving an individual isomer of a compound of the invention from a mixture of isomers;
(g) optionally converting a non-derivatized compound of the invention into a pharmaceutically acceptable prodrug derivative; and
(h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following examples that illustrate the preparation of compounds of Formula I according to the invention.

Example 1

8-Bromo-10-fluoro-2-hydroxy-9-trifluoromethyl-5,11-dihydro-6H-benzo[a]carbazole-3-carboxylic acid methyl ester

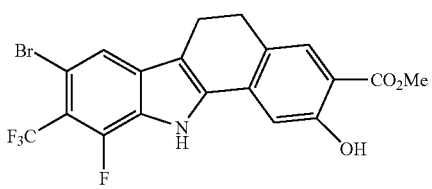

Step 1: 3-hydroxy-5-oxo-4a,5,6,7,8,8a-hexahydro-naphthalene-2-carboxylic acid methyl ester:

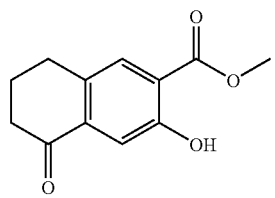

To a solution of 3,5-dihydroxy-2-naphthoic acid (30 g, 147 mmol) in MeOH (400 mL) in a Parr Bomb, is added Pd(OH)$_2$ (20% wt on carbon, 1.5 g) dispersed in MeOH (30 mL). The mixture was pressurized with H$_2$ to 1000 psi, and stirred at 50° C. overnight. Then the system is depressurized, and the mixture is filtered through a short silica gel padusing methanol. The filtrate is concentrated and re-dissolved in diethyl ether (250 mL) and MeOH (50 mL). Then trimethylsilyl diazomethane (2M in diethyl ether, 70 mL) is added. After stirring for 10 min, the mixture is concentrated and purified through silica gel flash column chromatography (eluent: 20–25% ethyl acetate in hexanes) to afford 11.5 g of an off-white solid of 3,5-dihydroxy-4a,5,6,7,8,8a-hexahydro-naphthalene-2-carboxylic acid methyl ester.

To a solution of 3,5-Dihydroxy-4a,5,6,7,8,8a-hexahydro-naphthalene-2-carboxylic acid methyl ester (3 g, 13.5 mmol) in DCM (100 mL) is added PDC (5.33 g, 14.2 mmol). The suspension is stirred at room temperature overnight. Upon completion of the reaction, the mixture is filtered through a short silica gel pad rinsing with DCM. After evaporation of the solvent, the crude product is obtained as light yellow solid. Recrystallization with DCM and hexanes affords 2.4 g of 3-hydroxy-5-oxo-4a,5,6,7,8,8a-hexahydro-naphthalene-2-carboxylic acid methyl ester as white crystalline solid; LC/MS calculated for [M+H]$^+$ C$_{12}$H$_{12}$O$_4$: 221.1, found: 221.1.

Step 2: (4-Bromo-2-fluoro-3-trifluoromethyl-phenyl)-hydrazine:

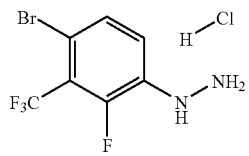

A sample of 4-bromo-2-fluoro-3-trifluoromethyl-phenyl aniline (4 g, 15.5 mmol) is suspended in concentrated HCl (36 mL) and cooled in an ice/salt bath. The reaction is then treated dropwise with a solution of NaNO$_2$ (1.12 g, 16.3 mmol) in water (36 mL). The reaction is allowed to stir for 30 minutes and then treated with a solution of SnCl$_2$ dihydrate (17.5 g, 77.5 mmol) in concentrated HCl (36 mL). The reaction is then stirred for 1 hour in an ice/water bath followed by an hour at room temperature. The reaction is then filtered and the solid is treated with aqueous 50% NaOH solution (30 mL) and ether (50 mL). The aqueous phase is extracted once more with ether and the combined organics are dried over MgSO$_4$ and filtered. The resulting solution is treated with 5 mL of 4 M HCl in dioxane while stirring and the resulting solid is collected and dried under high vacuum to afford 2.44 g of (4-Bromo-2-fluoro-3-trifluoromethyl-phenyl)-hydrazine hydrochloride; LC/MS calculated for [M+H]$^+$ C$_7$H$_5$BrF$_4$N$_2$: 273.0, found: 272.9.

Step 3: A sample of (4-Bromo-2-fluoro-3-trifluoromethyl-phenyl)-hydrazine hydrochloride (199 mg, 642 µmol) and 3-hydroxy-5-oxo-4a,5,6,7,8,8a-hexahydro-naphthalene-2-carboxylic acid methyl ester (141 mg, 642 µmol) are treated with anhydrous ZnCl$_2$ (219 mg, 1.60 mmol) and acetic acid (8 mL). The reaction is heated to 105° C. overnight. After cooling to room temperature, the solvent is removed by rotary evaporation. The reaction is then treated with ethyl acetate and extracted with 1 M HCl twice. The organics are then dried over MgSO$_4$ and filtered. The residue is then crystallized from methanol to afford 194 mg of the title compound as a white solid; $^1$H NMR (400 MHz, DMSO-d$_6$) δ 12.58 (s, 1H), 10.56 (s, 1H), 7.93 (s, 1H), 7.73 (s, 1H), 7.54 (s, 1H), 3.92 (s, 3H), 3.00-2.88 (m, 4H); ESIMS m/z for (M$^+$+H$^+$) calculated 458.0, found 458.0.

Example 2

8-Bromo-10-fluoro-2-hydroxy-9-trifluoromethyl-5,11-dihydro-6H-benzo[a]carbazole-3-carboxylic acid

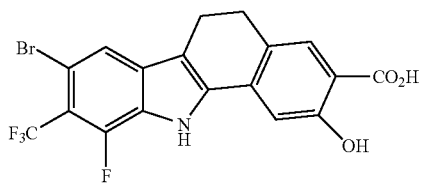

A sample of 8-Bromo-10-fluoro-2-hydroxy-9-trifluoromethyl-5,11-dihydro-6H-benzo[a]carbazole-3-carboxylic acid methyl ester (28.9 mg, 63.4 µmol) is treated with ethanol (0.3 mL) and water (0.5 mL) followed by LiOH (4 mg, 190 µmol). The reaction is then stirred at 50° C. overnight. The reaction is then diluted with ethyl acetate and extracted with 1 M HCl. The organics are then dried over MgSO$_4$, filtered and the solvent is removed. The resulting residue is purified using a UV triggered HPLC to afford 22 mg of the title compound as a white solid; $^1$H NMR (400 MHz, MeOD) δ 7.78 (s, 1H), 7.76 (s, 1H), 7.32 (s, 1H), 3.00 (m, 2H), 2.95 (2, H); LC/MS calculated for [M+H]$^+$ C$_{18}$H$_{11}$F$_4$NO$_3$: 445.1, found: 445.9.

By repeating the procedures described in the above examples, using appropriate starting materials, the following compounds of Formula I, as identified in Table 1, are obtained.

TABLE 1

| Compound # | Structure | NMR and/or ESMS |
|---|---|---|
| 3 | 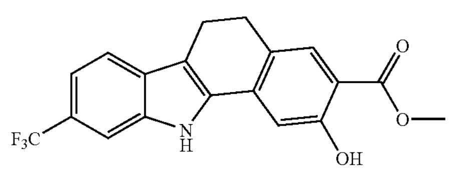 | $^1$H NMR (400 MHz, d6-DMSO) δ 12.04 (s, 1H), 10.61 (s, 1H), 7.75 (m, 2H), 7.69 (s, 1H), 7.32 (m, 2H), 3.92 (s, 3H), 2.97 (m, 4H); LC/MS calcd. for [M + H]$^+$ C$_{19}$H$_{15}$FNO$_3$: 362.3, found: 362.1. |
| 4 | 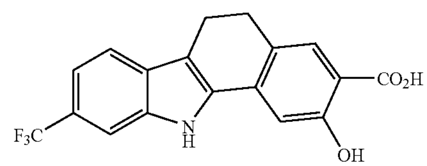 | LC/MS calcd. for [M + H]$^+$ C$_{18}$H$_{12}$F$_3$NO$_3$: 348.1, found: 348.0. |
| 5 | 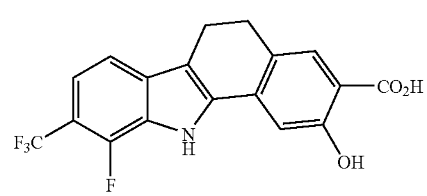 | LC/MS calcd. for [M + H]$^+$ C$_{18}$H$_{11}$F$_4$NO$_3$: 366.1, found: 366.0. |

The staffing hydrazine is prepared from commercially available 2-fluoro-3-trifluoromethyl aniline as described in example 1, step 2.

TABLE 1-continued

| Compound # | Structure | NMR and/or ESMS |
|---|---|---|
| 6 | 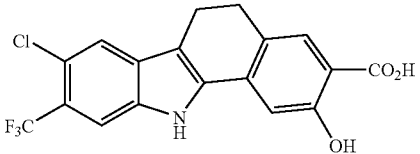 The starting hydrazine is prepared from commercially available 4-chloro-3-trifluoromethyl aniline as described in example 1, step 2. | LC/MS calcd. for [M + H]$^+$ C$_{18}$H$_{11}$ClF$_3$NO$_3$: 382.0, found: 382.0. Obtained as a regioisomeric mixture. |
| 7 | 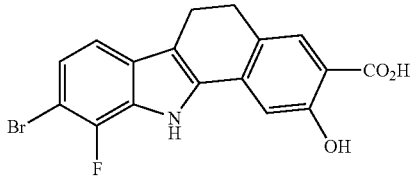 | (DMSO-d6) d 12.02 (bs, 1H), 7.61 (s, 1H), 7.39 (s, 1H), 7.28 (d, 1H), 7.13 (dd, 1H), 2.96-2.85 (m, 4H); LC/MS calcd. for [M + H]$^+$ C$_{17}$H$_{11}$BrFNO$_3$: 376.0, found: 376. |
| 8 | 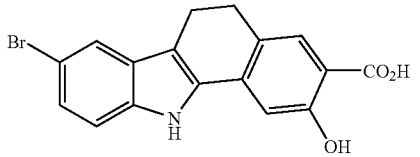 | LC/MS calcd. for [M + H]$^+$ C$_{17}$H$_{12}$BrNO$_3$: 358.0, found: 358.0. |
| 9 | 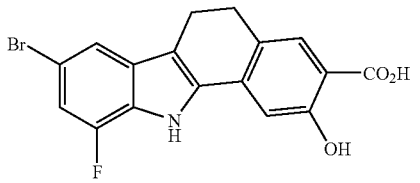 The starting hydrazine is prepared from commercially available 4-bromo-2-fluoro aniline as described in example 1, step 2. | LC/MS calcd. for [M + H]$^+$ C$_{17}$H$_{11}$BrFNO$_3$: 376.0, found: 376.0. |
| 10 | 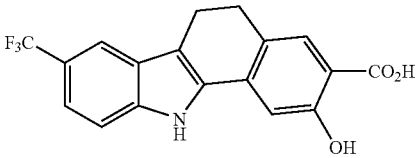 | (CD$_3$OD) δ 7.82 (s, 1H), 7.77 (s, 1H), 7.52 (d, 1H), 7.37 (d, 1H), 7.12 (s, 1H), 3.00-2.92 (m, 4H); LC/MS calcd. for [M + H]$^+$ C$_{18}$H$_{12}$BF$_3$NO$_3$: 348, found: 348. |
| 11 | 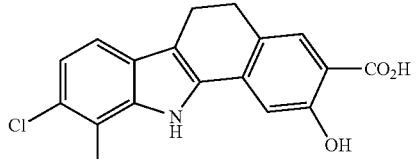 | LC/MS calcd. for [M + H]$^+$ C$_{17}$H$_{11}$ClFNO$_3$: 332.0, found: 332.0. |
| 12 | 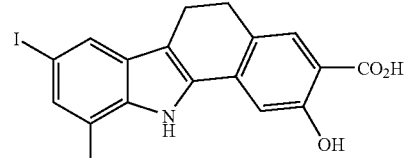 The starting hydrazine is prepared from commercially available 4-iodo-2-fluoro aniline as described in example 1, step 2. | LC/MS calcd. for [M + H]$^+$ C$_{17}$H$_{11}$FINO$_3$: 424.0, found: 423.9. |

TABLE 1-continued

| Compound # | Structure | NMR and/or ESMS |
|---|---|---|
| 13 | 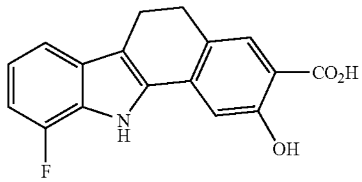 | LC/MS calcd. for [M + H]⁺ $C_{17}H_{12}FNO_3$: 298.1, found: 298.1. |
| 14 | 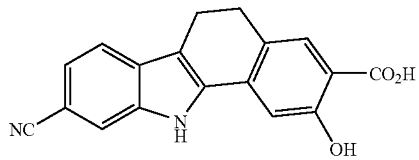 | LC/MS calculated for [M + H]⁺ $C_{18}H_{12}FN_2O_3$: 305.1, found: 305.1. |
| 15 | 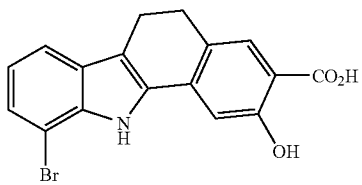 | LC/MS calculated for [M + H]⁺ $C_{17}H_{12}BrNO_3$: 358.0, found: 358.0. |
| 16 | 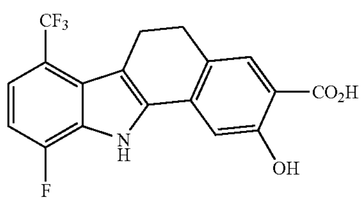 | (DMSO-d6) d 12.49 (s, 1H), 7.72 (s, 1H), 7.58 (s, 1H), 7.48-7.41 (m, 1H), 7.16 (dd, 1H), 2.98-2.91 (m, 4H); LC/MS calcd. for [M + H]⁺ $C_{18}H_{11}F_4NO_3$: 366.1, found: 366.0. |
| 17 | 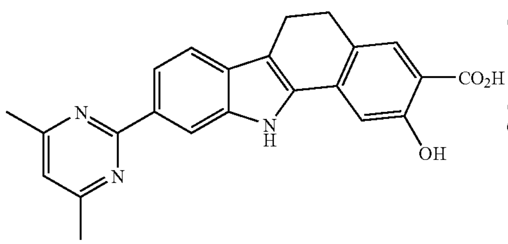 | (DMSO-d6) δ 11.66 (s, 1H), 11.31 (bs, 1H), 8.52 (s, 1H), 8.17 (d, 1H), 7.72 (s, 1H), 7.62 (d, 1H), 7.23 (s, 1H), 7.12 (s, 1H), 3.01-2.91 (m, 4H), 2.55-2.45 (m, 6H); LC/MS calcd. for [M + H]⁺ $C_{23}H_{19}N_3O_3$: 386.1, found: 386.1. |
| 18 | 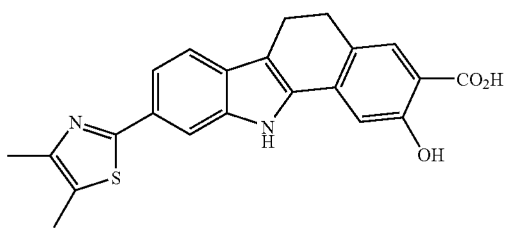 | (CD3OD) δ 7.93 (s, 1H), 7.78 (s, 1H), 7.69 (d, 1H), 7.52 (d, 1H), 7.16 (s, 1H), 2.99-2.92 (m, 4H), 2.48 (s, 3H), 2.42 (s, 3H); LC/MS calcd. for [M + H]⁺ $C_{22}H_{18}N_2O_3S$: 391.1, found: 391.0. |

For Compound 17: Preparation of 3-(4,6-Dimethyl-pyrimidin-2-yl)-phenylamine

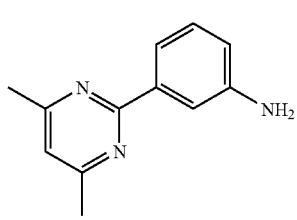

A mixture of 2-Chloro-4,6-dimethyl-pyrimidine (92 mg, 0.645 mmol, 1 eq.), 3-aminobenzene boronic acid (100 mg, 0.645 mmol, 1 eq.), $Na_2CO_3$ (137 mg, 1.29 mmol, 2 eq.), and $Pd(PPh_3)_2Cl_2$ (23 mg, 0.032 mmol. 5 mol %) in a 1:1 v/v mixture of $CH_3CN/H_2O$ (2.6 mL) is purged with $N_2$ for 5 minutes and then heated in a microwave at 150° C. for 5 minutes. After cooling to room temperature, the reaction is diluted with EtOAc and sequentially washed with saturated aqueous $NaHCO_3$ and saturated aqueous NaCl. The organic solution is dried over $Na_2SO_4$. After concentration, the residue is purified by silica gel chromatography (1:1 hexanes/EtOAc) to give 3-(4,6-Dimethyl-pyrimidin-2-yl)-phenylamine as a yellow semisolid. [MS: (ES⁺) 200.1 (M+1)⁺].

This material is then converted to the hydrazine in the same manner as described in example 1, step 2.

For Compound 18: Preparation of 3-(4,5-Dimethyl-thiazol-2-yl)-phenylamine

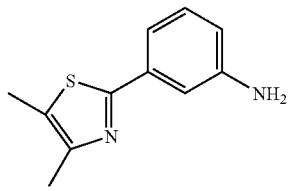

To a solution of 3-amino-thiobenzamide (200 mg, 1.31 mmol, 1 eq.) in EtOH (4 mL) is added 3-chloro-2-butanone (140 mg, 1.31 mmol, 1 eq.). The mixture is heated at 100° C. for 72 h. After cooling to room temperature, the reaction is diluted with EtOAc and sequentially washed with saturated aqueous NaHCO₃, H₂O and saturated aqueous NaCl. The organic solution is dried over Na₂SO₄. After concentration, the residue is purified by silica gel chromatography (2:1 hexanes/EtOAc) to give 3-(4,5-Dimethyl-thiazol-2-yl)-phenylamine as a yellow oil. [MS: (ES⁺) 205.1 (M+1)⁺].

This material is then converted to the hydrazine in the same manner as described in example 1, step 2.

Example 19

2-Hydroxy-8-phenyl-5,11-dihydro-6H-benzo[a]carbazole-3-carboxylic acid

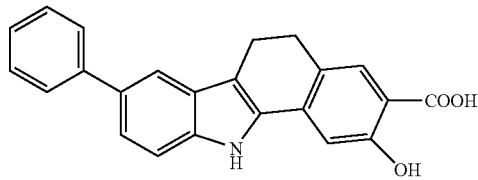

Step 1: 8-Bromo-2-hydroxy-5,11-dihydro-6H-benzo[a]carbazole-3-carboxylic acid methyl ester

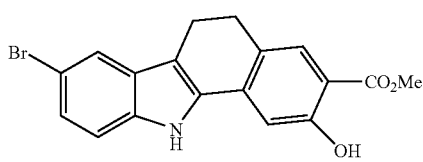

To a mixture of 4-bromo hydrazine (225 mg, 1 mmol), 3-hydroxy-5-oxo-5,6,7,8-tetrahydro-naphthalene-2-carboxylic acid methyl ester (220 mg, 1 mmol) and ZnCl₂ (272 mg, 2 mmol) in a sealed tube is added acetic acid (2 mL). The mixture is purged with nitrogen, and heated at 105° C. overnight. The reaction was cooled down and diluted with water, NaHCO₃ sat. solution is added to neutralize the acetic acid. The mixture is extracted with EtOAc (3×20 mL). The combined organic phases are washed with NaHCO₃ (sat.) solution and brine, and dried over NaSO₄. The crude product, obtained as yellow solid after evaporation of solvent, and is used as it is for next step.

Steps 2 and 3: To a mixture of the crude product (20 mg, 0.054 mmol) from previous step, phenylboronic acid (13 mg, 0.11 mmol), cesium fluoride (32 mg, 0.22 mmol) in dioxane (2 mL), is added palladium bis(tri-tert-butylphosphine) (3 mg, 10% mmol) in a microwave tube. The tube is sealed. The mixture is purged with N₂ for 3 min, and then heated at 120° C. for 10 min under microwave irradiation. The mixture is cooled, filtered and concentrated. The residue is transferred to a microwave tube and treated with ethanol/H₂O (1 mL/0.1 mL) followed by LiOH (12 mg, 0.54 mmol). The mixture is then heated at 120° C. for 6 min under microwave irradiation. The crude is filtered and applied to mass-trigger preparative HPLC for purification. The title compound is obtained as a yellow solid over 3 steps: ¹H NMR (400 MHz, DMSO-d₆) δ 11.59 (s, 1H), 11.3 (br, 1H), 7.82-7.80 (m, 1H), 7.72-7.69 (m, 3H), 7.48-7.42 (m, 4H), 7.33-7.29 (m, 1H), 7.26 (s, 1H), 2.97 (s, 4H); ESMS m/z 356.2 (M+H⁺).

Example 20

8-Allyl-10-fluoro-2-hydroxy-5,11-dihydro-6H-benzo[a]carbazole-3-carboxylic acid

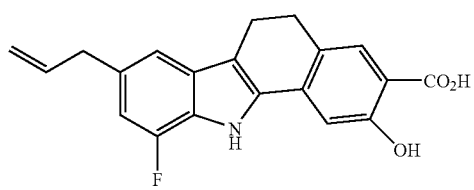

To a mixture 8-bromo-10-fluoro-2-hydroxy-5,11-dihydro-6H-benzo[a]carbazole-3-carboxylic acid methyl ester (50 mg, 0.13 mmol) (example 19, step 1), allyltributyl tin (56 mg, 0.15 mmol), cesium fluoride (38 mg, 0.25 mmol) dioxane (2 mL, anhydrous), is added palladium bis(tri-tert-butylphosphine) (4 mg, 5% mmol) in a microwave reaction tube. The tube is sealed and the mixture is purged with N₂ for 3 min and heated at 100° C. for 3 h. Then the mixture is cooled to room temperature and filtered. The filtrate is concentrated and re-dissolved in EtOH/H₂O (1 mL/0.1 mL). To the mixture is added lithium hydroxide (30 mg, 1.3 mmol). The mixture is heated at 120° C. for 6 min under microwave irradiation. Then the crude mixture is filtered and applied to mass-trigger preparative HPLC for purification. The title compound is obtained as a yellow solid; ESMS m/z 338.1 (M+H⁺).

Example 21

10-Fluoro-2-hydroxy-8-propyl-5,11-dihydro-6H-benzo[a]carbazole-3-carboxylic acid

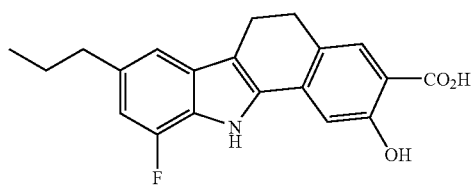

The procedure from Example 20 is followed except that after the Stille reaction is complete, the filtrate is concentrated and redissolved in ethanol/EtOAc (5 mL/3 mL). To the solution is added Pd/C (10%). The reaction mixture is degassed and purged with $H_2$ for several times and stirred under atmospheric hydrogen overnight. The mixture is filtered through celite and hydrolyzed and purified as in example 20 to afford the title compound: $^1$H NMR (400 MHz, DMSO-$d_6$) δ 11.72 (s, 1H), 11.29 (br, 1H), 7.67 (s, 1H), 7.41 (s, 1H), 7.16 (s, 1H), 6.85 (d, 1H, J=12.4 Hz), 2.94-2.87 (m, 4H), 2.62 (t, 2H, J=7.6 Hz), 1.63 (qt, 2H, J=7.6, 7.2 Hz), 0.91 (t, 3H, J=7.6 Hz), ESMS m/z 339.1 (M+H$^+$).

By repeating the procedures described in examples 19-21, using appropriate starting materials, the following compounds identified in Table 2, are obtained.

TABLE 2

| Compound # | Structure | NMR and/or ESMS |
|---|---|---|
| 22 | 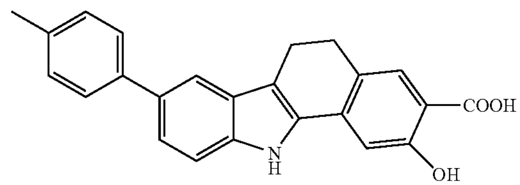 | ESMS m/z 370.2 (M + H$^+$). |
| 23 | 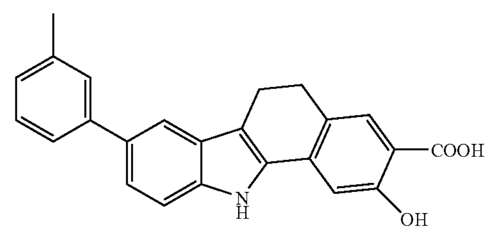 | ESMS m/z 370.2 (M + H$^+$). |
| 24 | 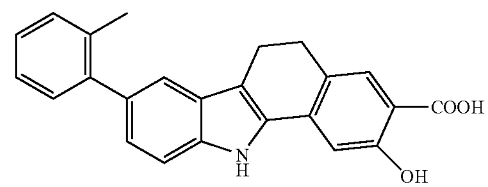 | ESMS m/z 370.2 (M + H$^+$). |
| 25 | 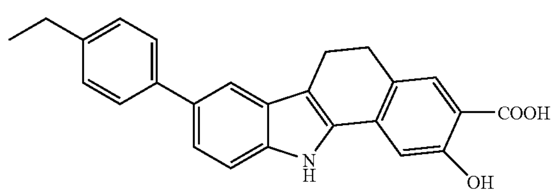 | ESMS m/z 384.2.2 (M + H$^+$). |
| 26 | 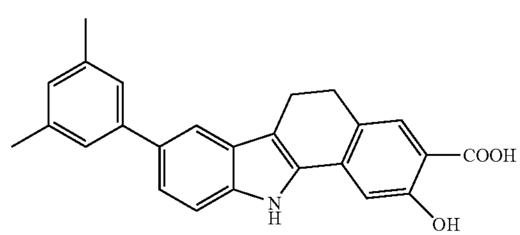 | ESMS m/z 384.2.2 (M + H$^+$). |
| 27 | 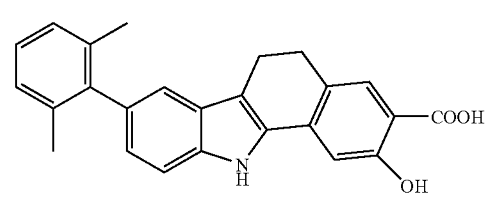 | ESMS m/z 384.2.2 (M + H$^+$). |

TABLE 2-continued

| Compound # | Structure | NMR and/or ESMS |
|---|---|---|
| 28 | 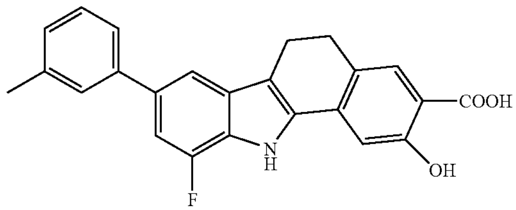 | ESMS m/z 388.2 (M + H+). |
| 29 | 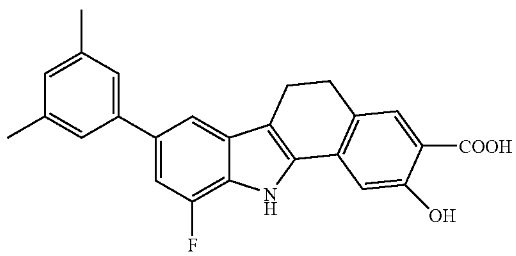 | ESMS m/z 402.2 (M + H+). |

Example 30

9-(phenyl)-2-hydroxy-5,11-dihydro-6H-benzo[a]carbazole-3-carboxylic acid

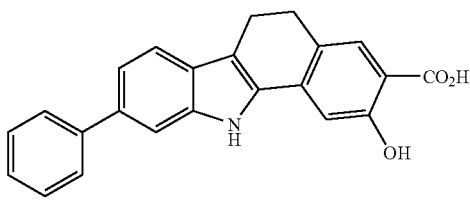

Step 1: 9-Bromo-2-hydroxy-5,11-dihydro-6H-benzo[a]carbazole-3-carboxylic acid methyl ester

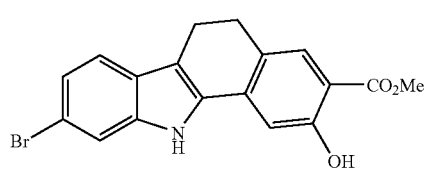

To a mixture of 3-bromo-phenyl hydrazine (225 mg, 1 mmol), 3-hydroxy-5-oxo-5,6,7,8-tetrahydro-naphthalene-2-carboxylic acid methyl ester (220 mg, 1 mmol) and $ZnCl_2$ (272 mg, 2 mmol) in a sealed tube, is added acetic acid (2 mL). The mixture is purged with nitrogen, and heated at 105° C. overnight. The reaction is cooled down and diluted with water. $NaHCO_3$ sat. solution is added to neutralize the acetic acid. The mixture was extracted with EtOAc (3×20 mL). The combined organic phases are washed with $NaHCO_3$ (sat.) solution and brine, and dried over $NaSO_4$. After concentration, the crude product is obtained as 1:1 ratio of 7- and 9-bromo-2-hydroxy-5,11-dihydro-6H-benzo[a]carbazole-3-carboxylic acid methyl ester and used as is for the next step.

Step 2: To a mixture of the crude product (50 mg, 0.13 mmol) from the previous step, phenylboronic acid (32 mg, 0.26 mmol) and cesium fluoride (78 mg, 0.52 mmol) in dioxane (3 mL, anhydrous) is added palladium bis(tri-tert-butylphosphine) (6 mg, 10% mmol). The tube is sealed. The mixture is purged with $N_2$ for 3 min, and then heated at 120° C. for 10 min under microwave irradiation. The mixture is cooled, filtered and concentrated. The residue is transferred to a microwave tube with ethanol/$H_2O$ (1 mL/0.1 mL). LiOH (12 mg, 0.54 mmol) is added. The mixture is heated at 120° C. for 6 min under microwave irradiation. The crude mixture is filtered and applied to a mass-triggered preparative HPLC for purification. The title compound is obtained as a yellow solid: $^1H$ NMR (400 MHz, DMSO-$d_6$) δ 11.59 (s, 1H), 11.3 (br, 1H), 7.82-7.80 (m, 1H), 7.72-7.69 (m, 3H), 7.48-7.42 (m, 4H), 7.33-7.29 (m, 1H), 7.26 (s, 1H), 2.97 (s, 4H); ESMS m/z 356.2 (M+H+).

By repeating the procedures described in example 30, using appropriate starting materials, the following compounds identified in Table 3, are obtained.

TABLE 3

| Compound # | Structure | NMR and/or ESMS |
|---|---|---|
| 31 | 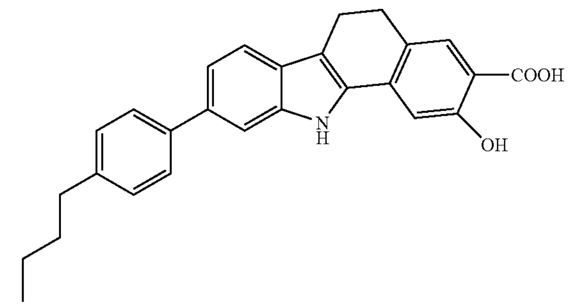 | $^1$H NMR (400 MHz, DMSO-$d_6$) δ 11.58 (s, 1 H), 7.67 (s, 1 H), 7.61-7.58 (m, 4 H), 7.33 (d, 1 H, J = 8.4 Hz) 7.29-7.26 (m, 3 H), 2.94 (dt, 4 H, J = 4, 7.6 Hz), 2.63 (t, 2 H, J = 7.6 Hz), 1.60 (tt, 2 H, J = 7.6, 7.6 Hz), 1.34 (qt, 2 H, J = 7.2, 7.2 Hz), 0.92 (t, 3 H, J = 7.2 Hz); ESMS m/z 412.2 (M + H$^+$). |
| 32 | 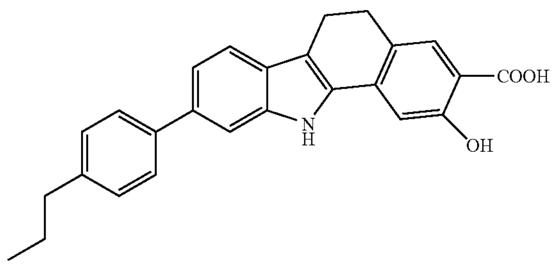 | ESMS m/z 398.2 (M + H$^+$). |
| 33 | 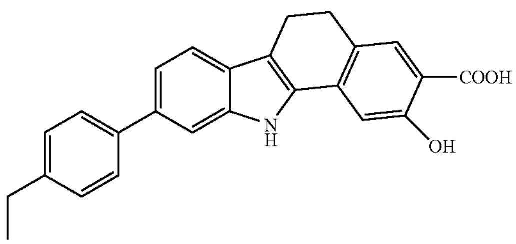 | ESMS m/z 384.2 (M + H$^+$). |
| 34 | 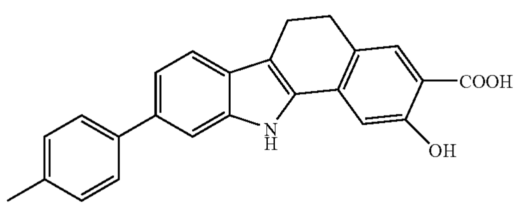 | ESMS m/z 370.2 (M + H$^+$). |
| 35 | 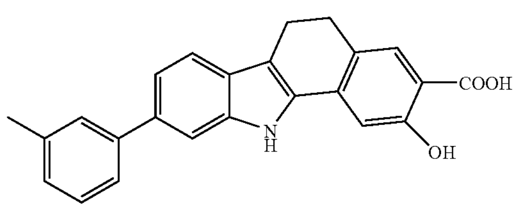 | ESMS m/z 370.2 (M + H$^+$). |
| 36 | 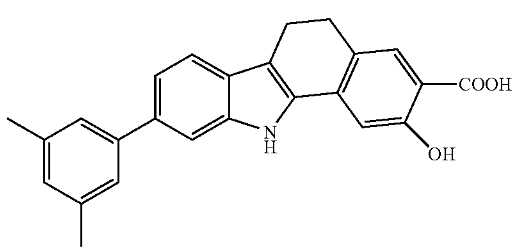 | ESMS m/z 384.2 (M + H$^+$). |

TABLE 3-continued

| Compound # | Structure | NMR and/or ESMS |
|---|---|---|
| 37 | 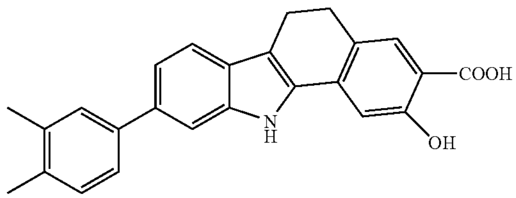 | ESMS m/z 384.2 (M + H$^+$). |
| 38 | 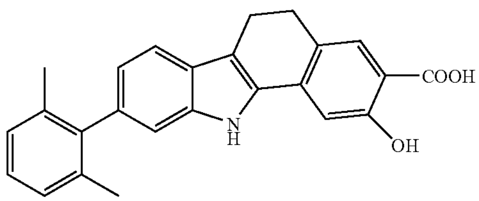 | ESMS m/z 384.2 (M + H$^+$). |
| 39 | 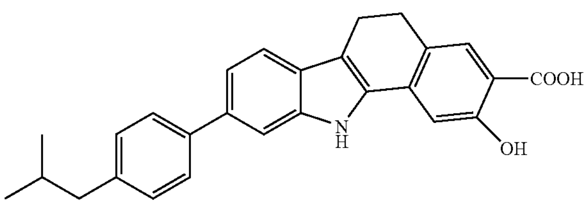 | ESMS m/z 412.2 (M + H$^+$). |
| 40 | 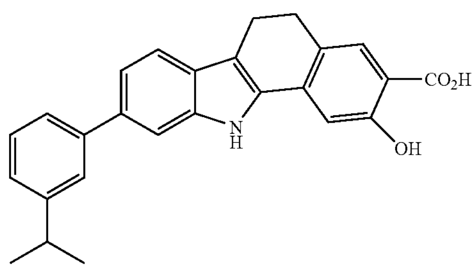 | (CD$_3$OD) δ 7.65 (s, 1 H), 7.59-7.33 (m, 4 H), 7.28-7.20 (m, 2 H), 7.11 (d, 1 H), 7.02 (s, 1 H), 2.93-2.85 (m, 5 H), 1.22 (d, 6 H); ESMS m/z 398 (M + H$^+$). |
| 41 | 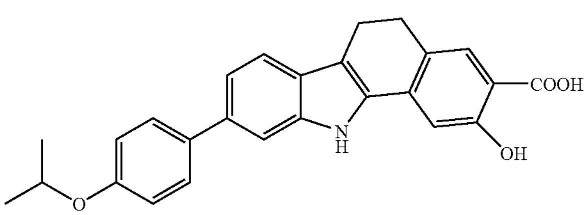 | ESMS m/z 414.2 (M + H$^+$). |
| 42 | 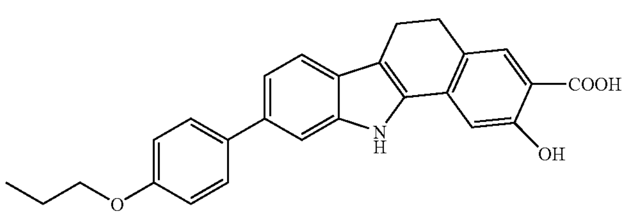 | ESMS m/z 414.2 (M + H$^+$). |

TABLE 3-continued

| Compound # | Structure | NMR and/or ESMS |
|---|---|---|
| 43 | 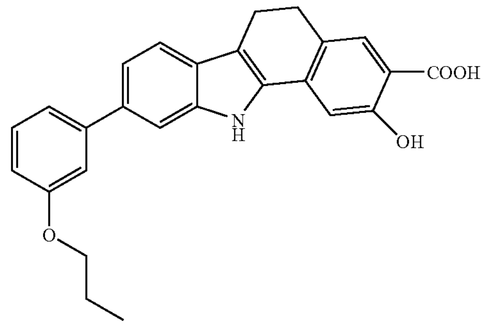 | ESMS m/z 414.2 (M + H$^+$). |
| 44 | 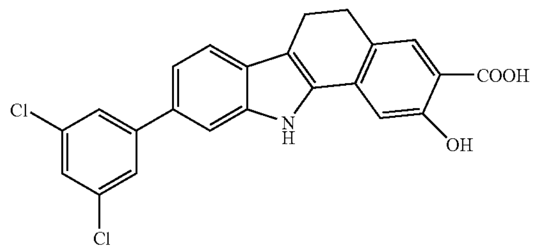 | ESMS m/z 424.0 (M + H$^+$). |
| 45 | 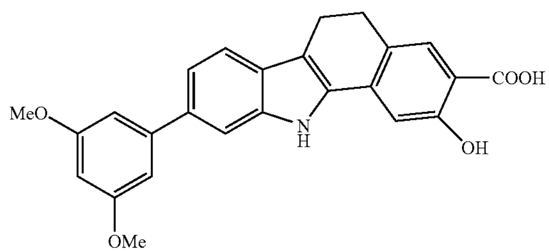 | ESMS m/z 416.1 (M + H$^+$). |
| 46 | 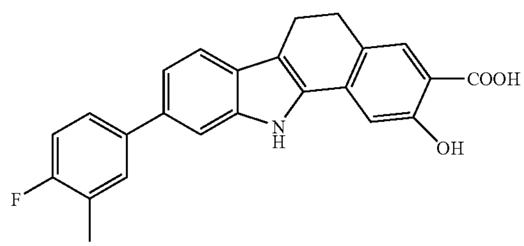 | ESMS m/z 388.1 (M + H$^+$). |
| 47 | 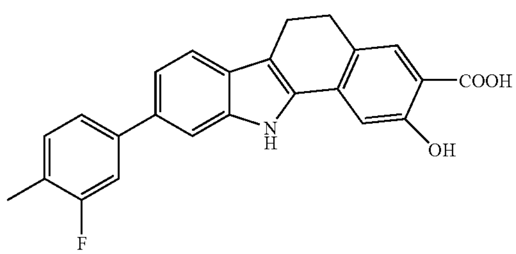 | ESMS m/z 388.1 (M + H$^+$). |
| 48 | 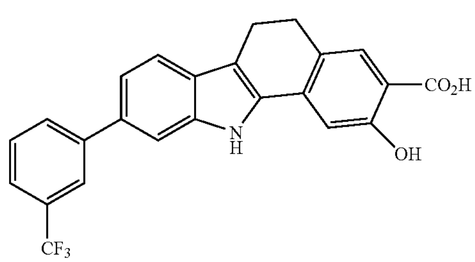 | ESMS m/z 468 (M + H$^+$). |

TABLE 3-continued

| Compound # | Structure | NMR and/or ESMS |
|---|---|---|
| 49 | (structure: 2-trifluoromethylphenyl-substituted carbazole with CO₂H and OH) | (CD$_3$OD) δ 7.78 (d, 1 H), 7.72 (s, 1 H), 7.62 (dd, 1 H), 7.54-7.47 (m, 2 H), 7.42 (d, 1 H), 7.32 (s, 1 H), 7.11 (s, 1 H), 6.98 (d, 1 H), 3.01-2.96 (m, 4 H); ESMS m/z 468 (M + H$^+$). |
| 50 | (structure: 4-(dimethylamino)phenyl-substituted carbazole with COOH and OH) | ESMS m/z 399.1 (M + H$^+$). |
| 51 | (structure: 4-(methoxymethyl)phenyl-substituted carbazole with COOH and OH) | ESMS m/z 400.1 (M + H$^+$). |
| 52 | (structure: 3,5-dimethyl-4-hydroxyphenyl-substituted carbazole with COOH and OH) | ESMS m/z 400.1 (M + H$^+$). |
| 53 | (structure: cyclohexyl-substituted carbazole with COOH and OH) The cyclohexyl zinc reagent is used instead of the boronic acid. | ESMS m/z 362.2 (M + H$^+$). |
| 54 | (structure: 3-pyridyl-substituted carbazole with CO₂H and OH) 3-(Tributylstannyl)pyridine is used as the coupling partner. | ESMS m/z 357 (M + H$^+$). |

TABLE 3-continued

| Compound # | Structure | NMR and/or ESMS |
|---|---|---|
| 55 | 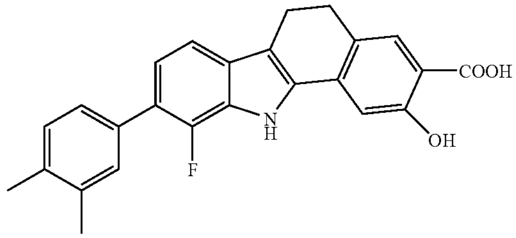 | ESMS m/z 402.1 (M + H+). |
| 56 | 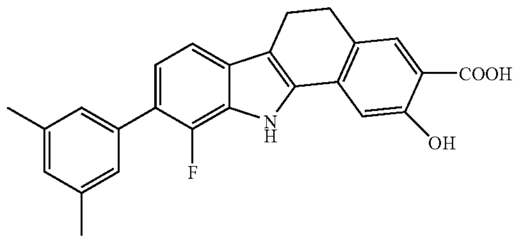 | $^1$H NMR (400 MHz, DMSO-d$_6$) δ 11.90 (s, 1 H), 11.30 (br, 1 H), 7.69 (s, 1 H), 7.48 (s, 1 H), 7.41 (d, 1 H, J = 8 Hz), 7.20 (m, 2 H), 7.11-7.08 (m, 1 H), 7.01 (s, 1 H), 2.98-2.91 (m, 4), 2.35 (s, 3 H), 2.35 (d, 3 H, J = 3.6 Hz), ESMS m/z 402.1 (M + H+). |

Example 57

9-Chloro-10-fluoro-5,11-dihydro-6H-benzo[a]carbazole-3-carboxylic acid

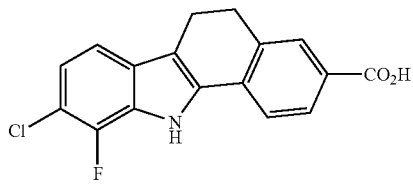

Step 1: 5-Oxo-5,6,7,8-tetrahydro-naphthalene-2-carboxylic acid methyl ester

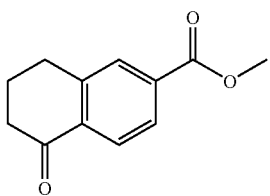

A sample of commercially available 5-Oxo-5,6,7,8-tetrahydro-naphthalene-2-carboxylic acid (200 mg, 1.05 mmol) is dissolved in a mixture of dichloromethane and methanol (5:1, 10 mL). The solution is then treated with a solution of trimethylsilyl diazomethane in tetrahydrofuran (2M) until the yellow color persists. The reaction is then treated with a small amount of acetic acid to destroy excess reagent and the solvent is removed. The residue is purified on silica gel to afford the title material as a yellow solid. ESMS m/z 204.1 (M+H+).

Steps 2-3: Samples of 5-Oxo-5,6,7,8-tetrahydro-naphthalene-2-carboxylic acid methyl ester and 2-fluoro-3-chlorophenylhydrazine hydrochloride are used to make the Fischer product followed by saponification as in example 1, step 3 and example 2 to afford the title material: $^1$H NMR (400 MHz, d$_6$-DMSO) δ 12.12 (s, 1H), 7.88 (m, 3H), 7.39 (m, 1H), 7.11 (dd, J=6.5, 1.9 Hz, 1H), 3.08 (m, 2H), 2.94 (m, 2H); LC/MS calculated for [M+H]+ C$_{17}$H$_{12}$FClNO$_2$: 316.7, found: 316.1.

Example 58

9-(3,5-Dimethyl-4-propoxy-phenyl)-10-fluoro-5,11-dihydro-6H-benzo[a]carbazole-3-carboxylic acid methyl ester Step 1: 2-(3,5-Dimethyl-4-propoxy-phenyl)-4,4,5,5-tetramethyl-[1,3,2]dioxaborolane

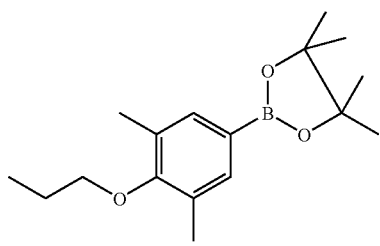

A mixture 2,6-Dimethyl-4-(4,4,5,5-tetramethyl-[1,3,2]dioxaborolan-2-yl)-phenol (500 mg, 2.02 mmol, 1 eq.), 1-bromopropane (793 mg, 6.45 mmol, 3.2 eq.), and $K_2CO_3$ (334 mg, 2.42 mmol, 1.2 eq.) in acetone (20 mL) is heated at 65° C. for 4 days. After cooling to room temperature, the reaction is concentrated, diluted with EtOAc and sequentially washed with $H_2O$ and saturated aqueous NaCl. The organic solution is dried over $Na_2SO_4$ and concentrated to give 2-(3,5-Dimethyl-4-propoxy-phenyl)-4,4,5,5-tetramethyl-[1,3,2]dioxaborolane as a clear oil.

Step 2: A sample of crude 9-Chloro-10-fluoro-5,11-dihydro-6H-benzo[a]carbazole-3-carboxylic acid methyl ester (prepared as in example 57, step 2) and 2-(3,5-Dimethyl-4-propoxy-phenyl)-4,4,5,5-tetramethyl-[1,3,2]dioxaborolane are coupled as in example 19, step 2 to afford the title material: ESMS m/z/z 458 (M+H⁺).

Example 59
9-(3,5-Dimethyl-4-propoxy-phenyl)-10-fluoro-5,11-dihydro-6H-benzo[a]carbazole-3-carboxylic acid

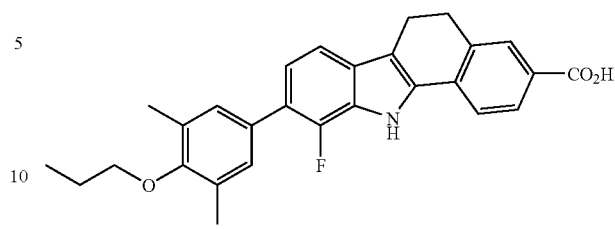

A sample of 9-(3,5-Dimethyl-4-propoxy-phenyl)-10-fluoro-5,11-dihydro-6H-benzo[a]carbazole-3-carboxylic acid methyl ester is saponified as in example 1, step 2 to afford the title material; (Acetone-d6) δ 11.07 (bs, 1H), 7.99 (s, 1H), 7.97 (d, 1H), 7.86 (d, 1H), 7.42 (d, 1H), 7.24 (s, 2H), 7.12 (dd, 1H), 3.82 (t, 2H), 3.17 (t, 2H), 3.08 (t, 2H), 2.31 (s, 6H), 1.94-1.84 (m, 2H), 1.10 (t, 3H); ESMS m/z 444 (M+H⁺).

By repeating the procedures described examples 57-59, using appropriate starting materials, the following compounds identified in Table 4, are obtained.

TABLE 4

| Compound # | Structure | NMR and/or ESMS |
|---|---|---|
| 60 | 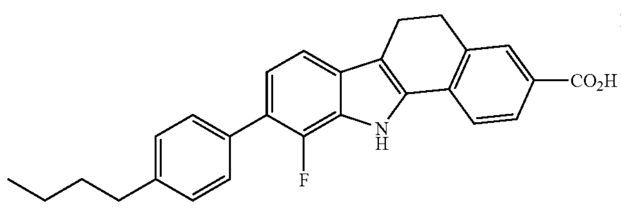 | ESMS m/z 414.2 (M + H⁺). |
| 61 | 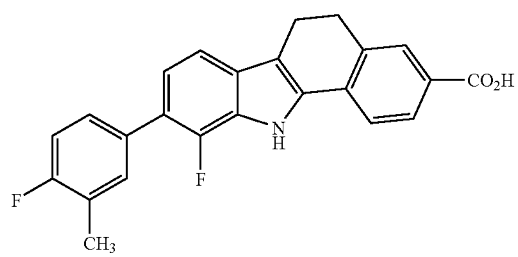 | ¹H NMR (400 MHz, d₆-DMSO) δ 12.02 (s, 1 H), 7.94 (m, 1 H), 7.88 (m, 2 H), 7.52 (m, 1 H), 7.43 (m, 2 H), 7.25 (dd, J = 9.3, 8.8 Hz, 1 H), 7.11 (dd, J = 7.6, 7.4 Hz, 1 H), 3.09 (dd, J = 7.5, 7.4 Hz, 2 H), 2.96 (dd, J = 7.8, 7.5 Hz, 2 H), 2.33 (s, 3 H); LC/MS calcd. for [M + H]⁺ C₂₄H₁₈F₂NO₂: 390.4, found: 390.0 |
| 62 | 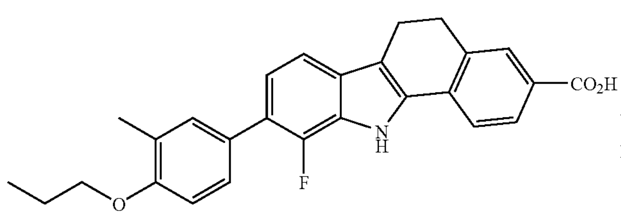 | ¹H NMR (Acetone-d6) d 10.96 (bs, 1 H), 7.94 (s, 1 H), 7.93 (d, 1 H), 7.82 (d, 1 H), 7.38-7.33 (m, 3 H), 7.12 (dd, 1 H), 6.98 (d, 1 H), 3.99 (t, 2 H), 3.12 (t, 2 H), 3.04 (t, 2 H), 2.19 (s, 3 H), 1.88-1.75 (m, 2 H), 1.06 (t, 3 H); ESMS m/z 430 (M + H⁺). |
| 63 | 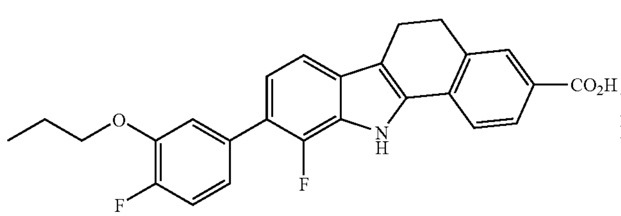 | (Acetone-d6) d 11.09 (bs, 1 H), 7.99 (s, 1 H), 7.98 (d, 1 H), 7.91 (d, 1 H), 7.49 (d, 1 H), 7.34 (d, 1 H), 7.26-7.13 (m, 3 H), 4.12 (t, 2 H), 3.18 (t, 2 H), 3.08 (t, 2 H), 1.91-1.81 (m, 2 H), 1.06 (t, 3 H); ESMS m/z 434 (M + H⁺). |

TABLE 4-continued

| Compound # | Structure | NMR and/or ESMS |
| --- | --- | --- |
| 64 | 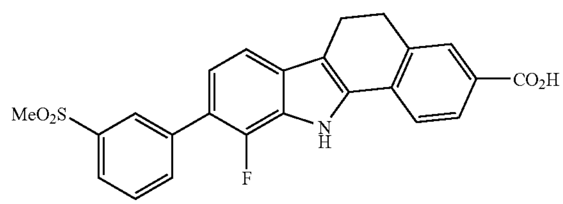 | ESMS m/z 436 (M + H+). |
| 65 | 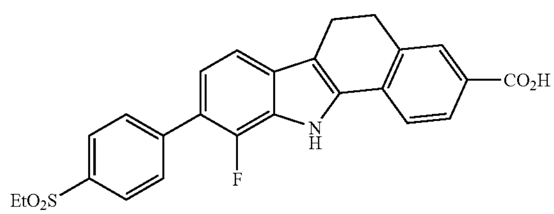 | ESMS m/z 450 (M + H+). |
| 66 | 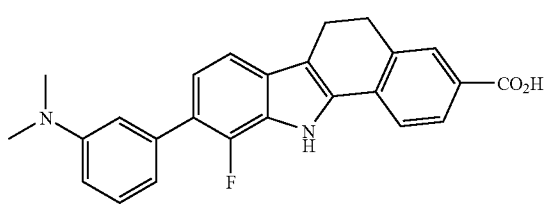 | (Acetone-d6) d 10.92 (bs, 1 H), 7.88 (s, 1 H), 7.86 (d, 1 H), 7.78 (d, 1 H), 7.32 (d, 1 H), 7.22 (dd, 1 H), 7.09 (dd, 1 H), 7.01 (s, 1 H), 6.93 (d, 1 H), 6.75 (d, 1 H), 3.08 (t, 2 H), 2.98-2.90 (m, 8 H); ESMS m/z 401 (M + H+). |
| 67 | 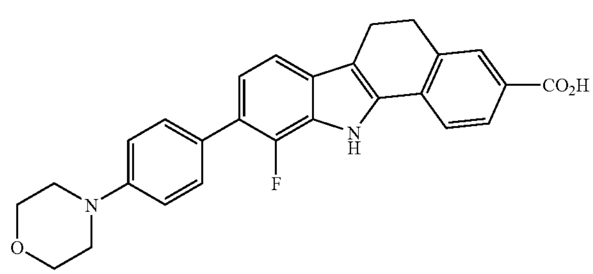 | (DMSO-d6) d 12.80 (bs, 1 H), 11.90 (bs, 1 H), 7.91-7.82 (m, 3 H), 7.48 (d, 2 H), 7.36 (d, 1 H), 7.10-6.98 (m, 3 H), 3.78-3.71 (m, 2 H), 3.20-3.15 (m, 2 H), 3.13-3.04 (m, 2 H), 3.00-2.92 (m, 2 H); ESMS m/z 443 (M + H+). |
| 68 | 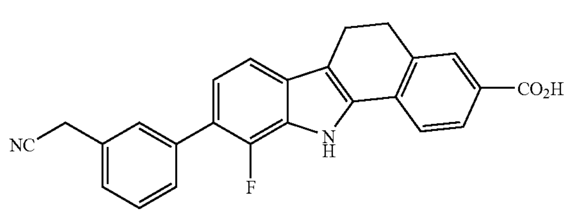 | ESMS m/z 397 (M + H+). |
| 69 | 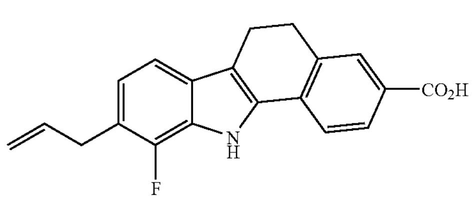 | (DMSO-d6) δ 12.88 (s, 1 H), 11.83 (s, 1 H), 7.86 (m, 3 H), 7.30 (d, J = 8.0 Hz, 1 H), 6.87 (m, 1 H), 6.04 (m, 1 H), 5.09 (m, 2 H), 3.49 (d, J = 6.2 Hz, 2 H), 3.06 (m, 2 H), 2.92 (m, 2 H); LC/MS calcd. for [M + H]+ $C_{20}H_{18}FNO_2$: 322.1, found 322.1. |

For Compound 63: The boronic acid was prepared as follows:

2-(4-Fluoro-3-propoxy-phenyl)-4,4,5,5-tetramethyl-[1,3,2]dioxaborolane

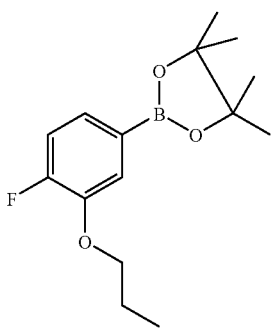

A mixture 5-Bromo-2-fluoro-phenol (prepared by the method of Elliott, M. et al. GB2187731) (500 mg, 2.62 mmol, 1 eq.), 1-bromopropane (322 mg, 2.62 mmol, 1 eq.), and K$_2$CO$_3$ (434 mg, 3.14 mmol, 1.2 eq.) in acetone (20 mL) is heated at 65° C. for 24 h. After cooling to room temperature, the reaction is concentrated, diluted with EtOAc and sequentially washed with 1 N aqueous NaOH and saturated aqueous NaCl. The organic solution is dried over Na$_2$SO$_4$. After concentration, the residue is purified by silica gel chromatography (3:1 hexanes/EtOAc) to give 4-Bromo-1-fluoro-2-propoxy-benzene as a yellow oil.

A mixture of 4-Bromo-1-fluoro-2-propoxy-benzene (224 mg, 0.961 mmol, 1 eq.), bis(pinacolato)diboron (268 mg, 1.057 mmol, 1 eq.), KOAc (283 mg, 2.88 mmol, 3 eq.), and Pd(dppf)$_2$Cl$_2$ (7 mg, 0.01 mmol. 1 mol %) in DMF (anhydrous, 1 mL) is purged with N$_2$ for 10 minutes and then heated in a sealed tube at 80° C. for 12 h. After cooling to room temperature, the reaction is diluted with EtOAc and washed with H$_2$O. The organic solution is dried over Na$_2$SO$_4$. After concentration, the residue is purified by silica gel chromatography (1:2 hexanes/CH$_2$Cl$_2$) to give 2-(4-Fluoro-3-propoxy-phenyl)-4,4,5,5-tetramethyl-[1,3,2]dioxaborolane as a clear oil: [MS: (ES$^+$) 281.2 (M+1)$^+$].

For compound 69: Allyltributyltin is used in place of a boronic acid.

Example 70

9-(4-Butyl-phenyl)-5,11-dihydro-6H-benzo[a]carbazole-3-carboxylic acid

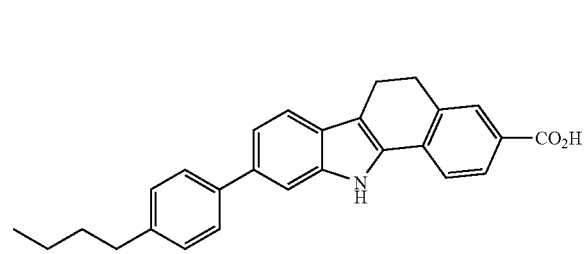

Step 1: 4'-Butyl-biphenyl-3-ylamine

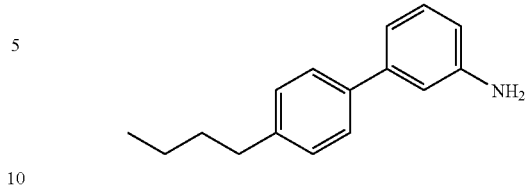

A sample of 3-bromoaniline (2.00 g, 11.6 mmol), 4-butylphenylboronic acid (3.1 g, 17.4 mmol) and cesium fluoride (5.3 g, 35 mmol) are charged to a microwave reaction vial and treated with anhydrous dioxane (12 mL) and bis(tri-tert-butylphospine) (600 mg, 1.16 mmol). The vial is sealed and purged with nitrogen for 5 minutes. The reaction is then heated to 120° C. for 5 minutes and filtered over celite washing with ethyl acetate. The solvent was removed and the crude material was purified by UV triggered reverse phase HPLC to afford the title compound: ESMS m/z 226.2 (M+H$^+$).

Step 2: (4'-Butyl-biphenyl-3-yl)-hydrazine hydrochloride

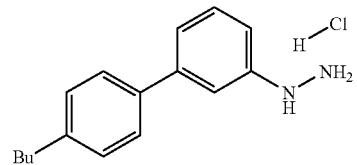

This material is prepared as in example 1, step 2.

Step 3: A sample of commercially available 5-Oxo-5,6,7,8-tetrahydro-naphthalene-2-carboxylic acid (75 mg, 0.39 mmol) and (4'-Butyl-biphenyl-3-yl)-hydrazine hydrochloride (115 mg, 0.41 mmol) are treated with zinc chloride (134 mg, 0.99 mmol) and acetic acid (5 mL). The reaction is then heated to 105° C. overnight and cooled to room temperature. The reaction is filtered and the filtrate is washed with methanol and dried on the high vacuum line to afford the title material as a single regioisomer. $^1$H NMR (400 MHz, DMSO-d$_6$) δ 11.63 (s, 1H), 7.90-7.84 (m, 2H), 7.75-7.71 (m, 1H), 7.62-7.57 (m, 4H), 7.35-7.31 (m, 1H), 7.28 (d, J=8.0 Hz, 2H), 3.11-3.05 (m, 2H), 2.99-2.92 (m, 2H), 2.62 (dd, J=7.6, 7.6 Hz, 2H), 1.65-1.55 (m, 2H), 1.40-1.29 (m, 2H), 0.92 (dd, J=7.3, 7.3 Hz, 3H); ESIMS m/z for (M$^+$+H$^+$) calculated 396.2, found 396.2.

Example 71

9-(4-Butyl-phenyl)-5,11-dihydro-6H-benzo[a]carbazole-3-carboxylic acid methylamide

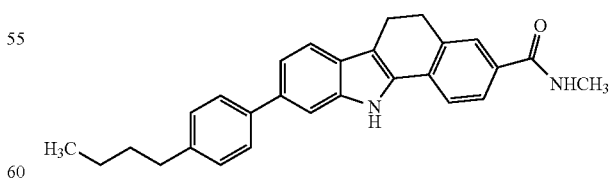

A sample of 9-(4-Butyl-phenyl)-5,11-dihydro-6H-benzo[a]carbazole-3-carboxylic acid (116.2 mg, 41 μmol) is dissolved in DMF (1 mL) and treated with HATU (16.3 mg, 41 μmol) and a solution of methylamine (2M) in tetrahydrofuran (0.1 mL, 100 μmol). After stirring overnight, the reaction is diluted with ethyl acetate and extracted with water twice. The organics are dried over MgSO₄ and the solvent is removed. The resulting residue is purified by mass triggered HPLC to afford the title material as a white solid after lyophilisation. LC/MS calculated for [M+H]⁺ C₂₈H₂₉N₂O: 409.5, found: 409.1

By repeating the procedure described in example 71, using appropriate starting materials, the following compounds identified in Table 5, are obtained.

Step 1: 1-oxo-indan-5-carbonitrile

TABLE 5

| Compound # | Structure | NMR and/or ESMS |
|---|---|---|
| 72 | 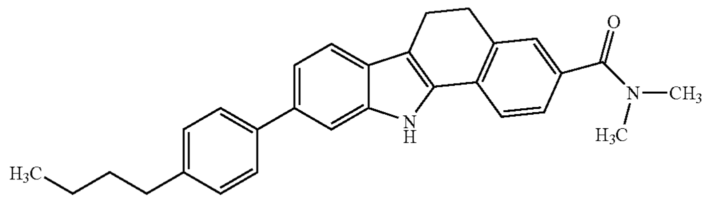 | ¹H NMR (400 MHz, d₆-DMSO) δ 11.58 (s, 1 H), 7.69 (m, 2 H), 7.58 (m, 4 H), 7.32 (m, 4 H), 7.28 (m, 2 H), 3.16 (d, J = 2.6 Hz, 3 H), 3.04 (m, 2 H), 2.93 (m, 2 H), 2.62 (m, 2 H), 2.08 (d, J = 4.2 Hz, 3 H), 1.59 (m, 2 H), 1.34 (m, 2 H), 0.92 (t, J = 7.3 Hz, 3 H); LC/MS calcd. for [M + H]⁺ C₂₉H₃₁N₂O: 423.6, found 432.2.. |
| 73 | A sample of example 61 is used as the acid | ¹H NMR (400 MHz, d₄-MeOD) δ 7.97 (s, 1 H), 7.71 (d, J = 8.4 Hz, 1 H), 7.44 (d, J = 7.5 Hz, 1 H), 7.38 (m, 1 H), 7.33 (s, 1 H), 7.30 (m, 3 H), 7.05 (m, 2 H), 3.06 (m, 2 H), 2.94 (m, 2 H), 2.32 (s, 3 H); LC/MS calcd. for [M + H]⁺ C₂₈H₂₅F₂N₂O₂: 459.5, found: 459.1. |
| 74 | A sample of example 61 is used as the acid | ¹H NMR (400 MHz, d₄-MeOD) δ 7.97 (m, 2 H), 7.73 (d, J = 7.8 Hz, 1 H), 7.47 (m, 1 H), 7.41 (m, 1 H), 7.34 (m, 2 H), 7.09 (m, 2 H), 3.53-3.81 (m, 4 H), 3.11 (m, 2 H), 2.99 (m, 5 H), 2.46 (m, 4 H), 2.34 (s, 3 H); LC/MS calcd. for [M + H]⁺ C₂₈H₂₈F₂N₃O: 472.5, found: 472.1. |

Example 75

7-(4-Butyl-phenyl)-6-fluoro-5,10-dihydro-indeno[1,2-b]indole-2-carboxylic acid

To a mixture 5-bromo-indan-1-one (1 g, 4.7 mmol), zinc cyanide (1.11 g, 9.4 mmol) in NMP/THF (2 mL/4 mL) in a sealed tube, is added palladium bis(tri-t-butyl-phosphine) (120 mg, 5% mmol). The mixture is purged with N₂ and heated at 120° C. for 3 h. Then the reaction mixture is cooled to rt, diluted with H₂O, and extracted with EtOAc (3×20 mL). The combined organic phases are washed with saturated ammonium chloride aqueous solution and brine and dried over Na₂SO₄. The crude product obtained after concentration is purified by silica gel column chromatography with mixed solvent hexanes/EtOAc (5/1-3/1) to afford 1-oxo-indan-5-carbonitrile as a light yellow solid: ESMS m/z 158.0 (M+H⁺).

Step 2: 1-oxo-indan-5-carboxylic acid methyl ester

To a suspension of 1-oxo-indan-5-carbonitrile (100 mg, 0.64 mmol) in KOH (25%, 0.21 mL) at 0° C., is added $H_2O_2$ (0.32 mL). The mixture is stirred at rt for 30 min, then at 50° C. for 1 h. After cooling to room temperature, the mixture is extracted with EtOAc (3×10 mL). The combined organic phases are washed with brine and dried over $Na_2SO_4$. Evaporation of the solvent affords 1-oxo-indan-5-carboxylic acid amide as a white solid. Aqueous HCl (4N, 3 mL) is added to the solid. The mixture is heated to 90° C. for 2 h. Then the reaction mixture is extracted with EtOAc (3×10 mL). The combined organic phasea are washed with brine. MeOH (5 mL) is added to the solution, followed by trimethylsilyldiazomethane (2M in ether) dropwise until all the carboxylic acid was consumed. Evaporation of solvent affords crude product, 1-oxo-indan-5-carboxylic acid methyl ester, which is pure enough for the next step. ESMS m/z 191.1 (M+H$^+$).

Steps 2-4: Samples of 1-oxo-indan-5-carboxylic acid methyl ester and 2-fluoro-3-chlorophenylhydrazine hydrochloride are used to make the Fischer product followed by Suzuki reaction with 4-butylphenylboronic acid and saponification as in example 30, steps 1 and 2 to afford the title material: $^1$H NMR (400 MHz, Acetone-d$_6$) δ 11.32 (s, 1H), 8.22 (s, 1H), 8.09 (d, 1H, J=7.6 Hz), 7.79 (d, 1H, J=8 Hz), 7.58-7.53 (m, 3H), 7.34 (s, 1H), 7.32 (s, 1H), 7.24-7.20 (m, 1H), 3.88 (s, 2H), 2.68 (t, 2H, J=7.6 Hz), 1.66 (tt, 2H, J=7.6, 7.6 Hz), 1.40 (qt, 2H, J=7.6, 7.6 Hz), 0.95 (t, 3H, J=7.60 Hz), ESMS m/z 400.1 (M+H$^+$).

Example 76

6-Fluoro-7-(4-fluoro-3-methyl-phenyl)-5,10-dihydro-indeno[1,2-b]indole-2-carboxylic acid

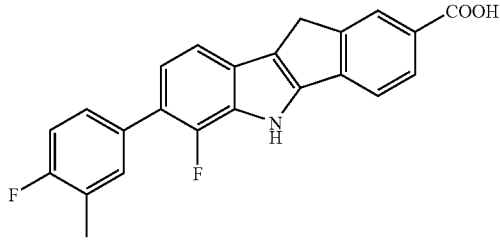

By following the same procedure as example 75 except using 3-methyl-4-fluorophenylboronic acid as the coupling partner in step 3, the title compound is obtained in a similar yield. ESMS m/z 376.1 (M+H$^+$).

Example 77

7-(4-Butyl-phenyl)-5,10-dihydro-indeno[1,2-b]indole-2-carboxylic acid

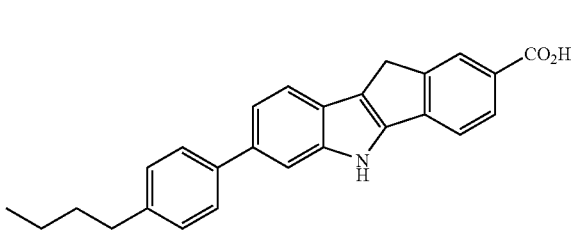

By reacting (4'-Butyl-biphenyl-3-yl)-hydrazine hydrochloride (example 70, step 1) and 1-oxo-indan-5-carboxylic acid methyl ester as described in example 1 followed by hydrolysis as described in example 2 the title material is obtained in similar yield. ESMS m/z 382.1 (M+H$^+$).

Example 78

7-(4-Butyl-phenyl)-6-fluoro-5,10-dihydro-indeno[1,2-b]indole-2-carbonitrile

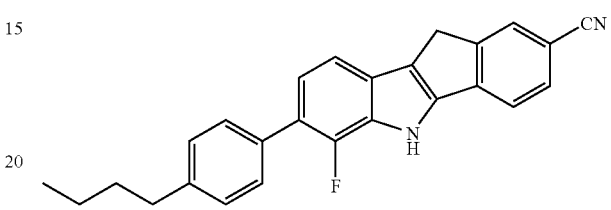

Step 1: (4'-Butyl-2-fluoro-biphenyl-3-yl)-hydrazine hydrochloride

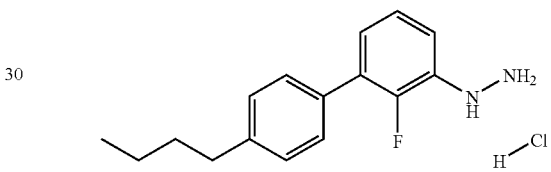

This material is prepared in an analogous manner to example 70, step 1 except that 2-fluoro-3-chloroaniline is used as the halide input. LC/MS calculated for [M+H]$^+$ $C_{16}H_{19}FN_2$: 259.2, found: 259.2.

Step 2: A sample of 1-oxo-indan-5-carbonitrile (133.5 mg, 0.85 mmol) (Example 74, step 1) and (4'-Butyl-2-fluoro-biphenyl-3-yl)-hydrazine hydrochloride (250.4, 0.85 mmol) are reacted together as in example 1, step 3 followed by purification by UV triggered reverse phase HPLC to afford the title compound as a white solid. LC/MS calculated for [M+H]$^+$ $C_{26}H_{21}FN_2$: 381.2, found: 381.2.

Example 79

9-(4-Butyl-phenyl-5,11-dihydro-6H-benzo[a]carbazole-3-carbonitrile

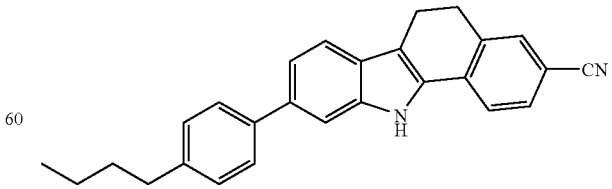

This material is prepared from commercially available 6-cyanotetralone and (4'-Butyl-biphenyl-3-yl)-hydrazine hydrochloride (example 70, step 1) in the same manner and similar yield as example 1, step 3. LC/MS calculated for [M+H]+ C27H25N2: 377.2, found: 377.1.

Example 80

9-(4-Butyl-phenyl)-3-(1H-tetrazol-5-yl)-5,11-dihydro-6H-benzo[a]carbazole

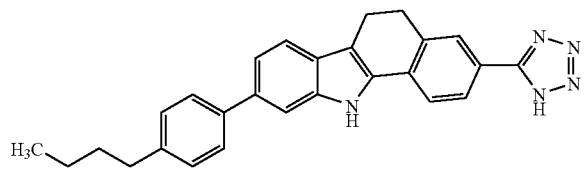

Step 1: 6-(1H-Tetrazol-5-yl)-3,4-dihydro-2H-naphthalen-1-one

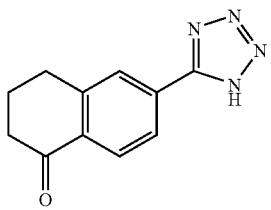

A sample of 6-cyanotetralone (102 mg, 0.60 mmol) is dissolved in DMF (1 mL) and treated with sodium azide (96.8 mg, 1.5 mmol), ammonium chloride (31.9 mg, 0.60 mmol) and lithium chloride (25.3 mg, 0.60 mmol) and heated to 120° C. overnight. The reaction is diluted with ethyl acetate and extracted with water twice. The residue is purified by UV triggered reverse phase HPLC to afford the title compound as a white solid.

Step 2: The 6-(1H-Tetrazol-5-yl)-3,4-dihydro-2H-naphthalen-1-one and (4'-Butyl-biphenyl-3-yl)-hydrazine hydrochloride (example 70, step 1) are reacted in the same manner and similar yield as example 1, step 3 except that the solid was washed with acetic acid rather than methanol. $^1$H NMR (400 MHz, $d_6$-DMSO) δ 11.66 (s, 1H), 7.97 (m, 2H), 7.84 (d, J=8.9 Hz, 11H), 7.63 (m, 4H), 7.34 (d, J=8.2 Hz, 2H), 7.29 (d, J=8.1 Hz, 2H), 3.13 (t, J=7.5 Hz, 2H), 2.99 (t, J=7.6 Hz, 2H), 2.63 (m, 2H), 1.60 (m, 2H), 1.35 (m, 2H), 0.93 (t, J=7.3 Hz, 3H); LC/MS calculated for [M+H]+ C27H26N5: 420.5, found: 420.1.

Example 81

9-(4-Butyl-phenyl)-5,11-dihydro-6H-benzo[a]carbazole-3-carboxylic acid amide

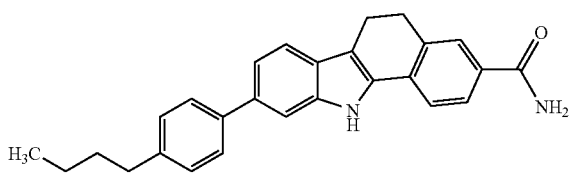

Step 1: 5-Oxo-5,6,7,8-tetrahydro-naphthalene-2-carboxylic acid amide

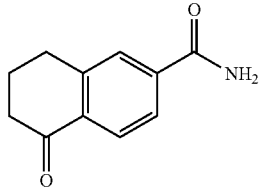

A sample of commercially available 6-cyanotetralone is hydrolyzed to the amide as in example 75, step 2. LC/MS calculated for [M+H]+ C11H11NO2: 189.1, found: 189.2.

Step 2: The 5-Oxo-5,6,7,8-tetrahydro-naphthalene-2-carboxylic acid amide and (4'-Butyl-biphenyl-3-yl)-hydrazine hydrochloride (example 70, step 1) are reacted in the same manner and similar yield as example 1, step 3. 11H NMR (400 MHz, $d_6$-DMSO) δ 11.60 (s, 1H), 7.83 (m, 2H), 7.70 (d, J=8.3 Hz, 1H), 7.59 (m, 3H), 7.27-7.35 (m, 4H), 3.05 (m, 2H), 2.96 (m, 2H), 2.62 (m, 2H), 1.60 (m, 2H), 1.35 (m, 2H), 0.92 (m, 3H); LC/MS calculated for [M+H]+ C27H27N2O: 395.5, found: 395.1.

Example 82

6-Fluoro-7-(4-fluoro-3-methyl-phenyl)-10,10-dimethyl-5,10-dihydro-indeno[1,2-b]indole-2-carboxylic acid amide

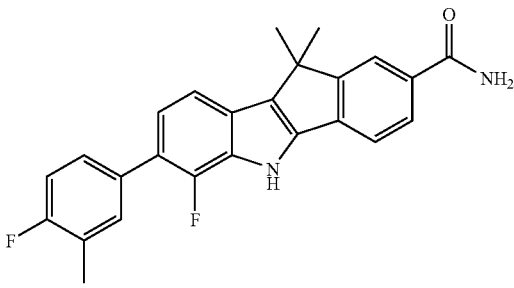

Step 1: 6-methoxy-1,1-dimethyl-indan

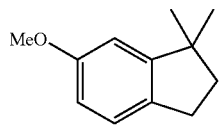

A stirred, cooled (−40° C.) solution of titanium tetrachloride in anhydrous dichloromethane (1M, 20 mL) under N2, is treated with a solution of dimethyl zinc (2M, 30 mL) in toluene. After 30 min, a solution of 6-methoxy-indan-1-one (1.62 g, 10 mmol) in dichloromethane (anhydrous, 10 mL) is added via syringe. After addition, the reaction is warmed to rt and stirring is continued for 3 h. The reaction mixture is then cooled to −40° C. and cautiously quenched with methanol (1 mL). The mixture is diluted with DCM and saturated aqueous ammonium chloride solution. The phases are separated and the aqueous phase is extracted with dichloromethane (2×20 mL). The combined organic phases are dried over Na2SO4, filtered and evaporated in vacuo to afford 6-methoxy-1,1-dimethyl-indan as an oil: $^1$H NMR (400 MHz, CDCl$_3$) δ 7.19-7.20 (m, 1H), 7.10-7.12 (m, 1H), 6.69-6.68 (m, 1H), 3.82 (s, 3H), 2.82 (t, 2H, J=7.2 Hz), 1.92 (t, 2H, J=7.2 Hz), 1.24 (s, 6H).

Step 2: 5-methoxy-3,3-dimethyl-indan-1-one

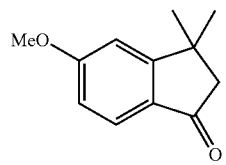

A solution of 6-methoxy-1,1-dimethyl-indan (1 g, 5.67 mmol) in acetic acid (5 mL) is cooled to 0° C. and treated with a solution of chromium trioxide (1.3 g, 13 mmol) in acetic acid/H$_2$O (5 mL/4 mL). Then the reaction mixture is allowed to warm to ambient temperature and stirred for 3 h. The reaction mixture is diluted and extracted with ethyl acetate (3×20 mL). The combined organic phases are washed with saturated aqueous NaHCO$_3$ and brine and dried over Na$_2$SO$_4$. Evaporation of solvent affords 5-methoxy-3,3-dimethyl-indan-1-one as a yellow oil: ESMS m/z 191.1 (M+H$^+$).

Step 3: 5-hydroxy-3,3-dimethyl-indan-1-one

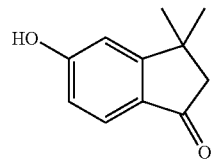

In a microwave reaction tube, a mixture of 5-methoxy-3,3-dimethyl-indan-1-one (880 mg, 4.63 mmol), benzenethiol (510 mg, 4.63 mmol), and potassium carbonate (64 mg, 0.46 mmol) in NMP (5 mL) is purged with N$_2$. The reaction mixture is heated at 220° C. for 30 min under microwave irradiation. The reaction mixture made to alkaline with 1N aqueous NaOH (10 mL) and extracted with Et$_2$O (3×20 mL). The aqueous part is acidified in an ice bath with 6N HCl and extracted with Et$_2$O (3×20 mL). The combined organic phases are washed with brine and dried over Na$_2$SO$_4$. After concentration, the crude product is purified with silica gel column chromatography (30% ethyl acetate in hexanes) to afford 5-hydroxy-3,3-dimethyl-indan-1-one as a yellow solid: $^1$H NMR (400 MHz, CDCl$_3$) δ 7.63 (d, 1H, J=8 Hz), 6.88 (d, 1H, J=2 Hz), 6.84 (dd, 1H, J=2, 8 Hz), 6.14 (s, 1H), 2.59 (s, 2H), 1.40 (s, 6H), ESMS m/z 177.1 (M+H$^+$).

Step 4: trifluoro-methanesulfonic acid 3,3-dimethyl-1-oxo-indan-5-yl ester

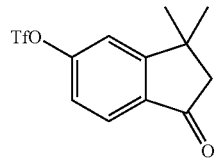

To a suspension of 5-hydroxy-3,3-dimethyl-indan-1-one (480 mg, 2.72 mmol) in DCM (anhydrous, 10 mL) is added triethylamine (1.2 mL, 8.16 mmol). The suspension becomes clear. The solution is cooled to −78° C., and treated with N-phenyltrifluoromethanesulfonimide (1.07 g, 3.0 mmol) in DCM (anhydrous, 3 mL). The reaction mixture is gradually warmed to ambient temperature and stirred overnight. The reaction mixture is diluted with DCM and washed with saturated aqueous ammonium chloride solution (2×50 mL) and brine and dried over Na$_2$SO$_4$. After evaporation in vacuo, the crude product is purified using silica gel column chromatography (10~15% ethyl acetate in hexanes) to afford the desired product, trifluoro-methanesulfonic acid 3,3-dimethyl-1-oxo-indan-5-yl ester, as an oil: ESMS m/z 309.10 (M+H$^+$).

Step 5: 3,3-dimethyl-1-oxo-indan-5-carbonitrile

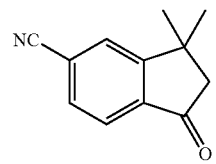

By following the same procedure as in Example 74, step 1,3,3-dimethyl-1-oxo-indan-5-carbonitrile is obtained as a white solid: $^1$H NMR (400 MHz, CDCl$_3$) δ 7.82 (s, 1H), 7.78 (d, 1H, J=8 Hz), 7.65 (dd, 1H, J=1.2, 7.6 Hz), 2.66 (s, 1H), 1.46 (s, 6H), ESMS m/z 186.1 (M+H$^+$).

Steps 6 and 7: A sample of 3,3-dimethyl-1-oxo-indan-5-carbonitrile and (4'-Fluoro-3'-methyl-biphenyl-3-yl)-hydrazine hydrochloride (prepared as in example 70, steps 1 and 2 except using 3-methyl-4-fluorophenylboronic acid and 3-chloro-2-fluoroaniline as the coupling partners) are reacted together as in example 1, step 3. The crude product is then subjected to hydrolysis as in example 19, step 3 to afford 6-fluoro-7-(4-fluoro-3-methyl-phenyl)-10,10-dimethyl-5,10-dihydro-indeno[1,2-b]indole-2-carboxylic acid amide as a light yellow solid: $^1$H NMR (400 MHz, acetone-d$_6$) δ 11.18 (s, 1H), 8.14 (s, 1H), 7.95 (dd, 1H, J=1.2, 7.6 Hz), 7.68 (d, 1H, J=8 Hz), 7.57 (d, 1H, J=8.4 Hz), 7.54 (dd, 1H, J=0.8, 7.6 Hz), 7.46-7.45 (m, 2H), 7.20-7.25 (m, 2H), 6.65-6.50 (br, 2H), 225 (d, 3H, J=1.6 Hz), 1.66 (s, 6H), ESMS 77/z 403.2 (M+H$^+$).

By repeating the procedures in example 81, using appropriate starting materials, the following compounds identified in Table 6, are obtained.

TABLE 6

| Compound # | Structure | NMR and/or ESMS |
|---|---|---|
| 83 | [structure]<br>A sample of 1-oxo-indan-5-carbonitrile (example 75, step 1) is used in steps 6. | ESMS m/z 375.1 (M + H$^+$). |
| 84 | [structure]<br>A sample of (4'-Butyl-2-fluoro-biphenyl-3-yl)-hydrazine hydrochloride (prepared as in example 78, step 1) is used in step 6 | ESMS m/z 427.2 (M + H$^+$). |
| 85 | [structure]<br>A sample of commercially available 6-cyanotetralone is used in step 6. | $^1$H NMR (400 MHz, d$_6$-DMSO) δ 11.95 (s, 1 H), 7.93 (m, 1 H), 7.89 (m, 1 H), 7.82 (m, 2 H), 7.52 (m, 1 H), 7.43 (m, 2 H), 7.32 (m, 1 H), 7.25 (m, 1 H), 7.10 (m, 1 H), 3.06 (m, 2 H), 2.96 (m, 2 H), 2.32 (s, 3 H); LC/MS calcd. for [M + H]$^+$ C$_{24}$H$_{19}$F$_2$N$_2$O: 389.4, found: 389.1. |
| 86 | [structure]<br>A sample of (4'-Butyl-biphenyl-3-yl)-hydrazine hydrochloride (example 70, step 1) and 6-cyanoindanone are used in step 6. | ESMS m/z 381.2 (M + H$^+$). |

Example 87

Trifluoro-methanesulfonic acid 9-(4-butyl-phenyl)-5,11-dihydro-6H-benzo[a]carbazol-3-yl ester

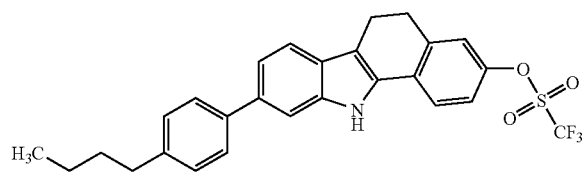

Step 1: Trifluoro-methanesulfonic acid 5-oxo-5,6,7,8-tetrahydro-naphthalen-2-yl ester

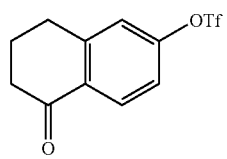

This known material is prepared according to a reported procedure (*Tetrahedron Lett.* 1992, 33(38), 5499).

Step 2: The title material is prepared by reacting Trifluoro-methanesulfonic acid 5-oxo-5,6,7,8-tetrahydro-naphthalen-2-yl ester and (4'-Butyl-biphenyl-3-yl)-hydrazine hydrochloride (example 70, step 2) in an analogous manner and similar yield to example 1, step 3 except that purification is accomplished by reverse phase UV triggered HPLC. $^1$H NMR (400 MHz, d$_6$-DMSO) d 11.63 (s, 1H), 7.78 (m, 2H), 7.58 (m, 4H), 7.46 (s, 1H), 7.33 (d, J=6.7 Hz, 1H), 7.28 (m, 2H), 3.09 (m, 2H), 2.95 (m, 2H), 2.64 (m, 2H), 1.60 (m, 2H), 1.35 (m, 2H), 0.94 (m, 3H); LC/MS calculated for [M+H]$^+$ C$_{27}$H$_{25}$F$_3$NO$_3$S: 500.5, found: 500.0.

Example 88

N-{3-[10-Fluoro-9-(4-fluoro-3-methyl-phenyl)-5,11-dihydro-6H-benzo[a]carbazol-3-yl]-phenyl}-methanesulfonamide

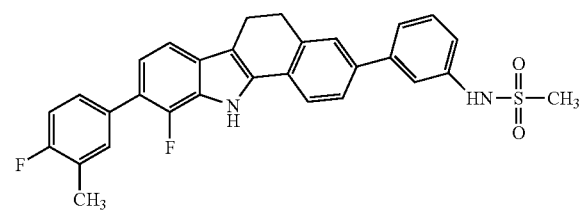

Step 1: N-[3-(5-Oxo-5,6,78-tetrahydro-naphthalen-2-yl)-phenyl]-methanesulfonamide

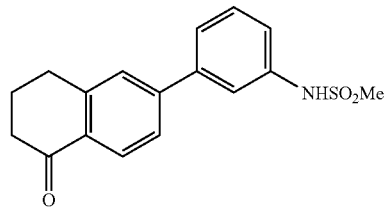

A sample of the known (*Tetrahedron Lett.* 1992, 33(38), 5499) Trifluoro-methanesulfonic acid 5-oxo-5,6,7,8-tetrahydro-naphthalen-2-yl ester (77.6 mg, 0.26 mmol) prepared according to known methods and 3-Methanesulfonylaminobenzeneboronic acid (85.1 mg, 0.40 mmol) are charged to a microwave reaction vessel and treated with anhydrous dioxane (1 mL) and cesium fluoride (94 mg, 0.62 mmol) followed by bis(tri-t-butyl-phosphine) palladium (13.5 mg, 0.026 mmol). The reaction is purged with nitrogen for minutes and then heated to 120° C. for 15 minutes under microwave irradiation. The reaction is diluted with ethyl acetate and extracted with water. The organics are then dried over MgSO$_4$ and the solvent is removed. The residue is purified by mass triggered reverse phase HPLC: LC/MS calculated for [M+H]$^+$ C$_{17}$H$_{17}$NO$_3$S: 316.1, found: 316.1.

Step 2: The title material is prepared by reacting N-[3-(5-Oxo-5,6,7,8-tetrahydro-naphthalen-2-yl)-phenyl]-methanesulfonamide and (4'-Fluoro-3'-methyl-biphenyl-3-yl)-hydrazine hydrochloride (prepared as in example 70, steps 1 and 2 except using 3-methyl-4-fluorophenylboronic acid and 3-chloro-2-fluoroaniline as the coupling partners) in an analogous manner to example 1, step 3 except that purification is accomplished by reverse phase UV triggered HPLC: $^1$H NMR (400 MHz, d$_6$-DMSO) δ 12.66 (s, 1H), 9.88 (s, 1H), 8.82 (d, J=8.7 Hz, 1H), 8.31 (m, 1H), 8.29 (d, J=8.6 Hz, 1H), 8.08 (d, J=8.2 Hz, 1H), 7.94 (m, 1H), 7.80 (d, J=8.6 Hz, 1H), 7.66 (m, 1H), 7.61 (m, 2H), 7.48 (m, 1H), 7.30 (m, 2H), 3.09 (m, 2H), 3.04 (s, 3H), 2.97 (m, 2H), 2.08 (s, 3H); LC/MS calculated for [M+H]$^+$ C$_{30}$H$_{25}$F$_2$N$_2$O$_2$S: 515.6, found: 515.0.

Example 89

[10-Fluoro-9-(4-fluoro-3-methyl-phenyl)-5,11-dihydro-6H-benzo[a]carbazol-3-yl]-carbamic acid tert-butyl ester

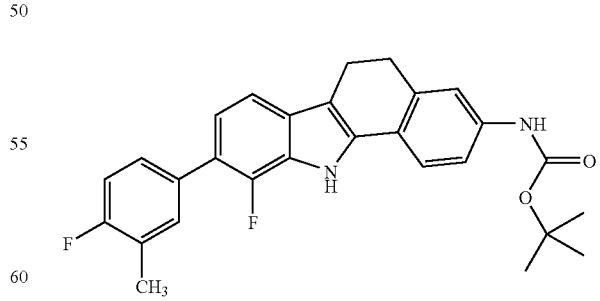

A sample of example 61 (441.5 mg, 1.13 mmol) is treated with tert-butyl alcohol (10 mL), diphenylphosphoryl azide (343 mg, 1.25 mmol) and triethylamine (126 mg, 1.25 mmol). The reaction is then refluxed overnight, concentrated and purified by UV triggered reverse phase HPLC to afford the title compound. LC/MS calculated for [M+H]+ $C_{28}H_{27}F_2N_2O_2$: 461.5, found: 461.2.

Example 90

10-Fluoro-9-(4-fluoro-3-methyl-phenyl)-5,11-dihydro-6H-benzo[a]carbazol-3-ylamine

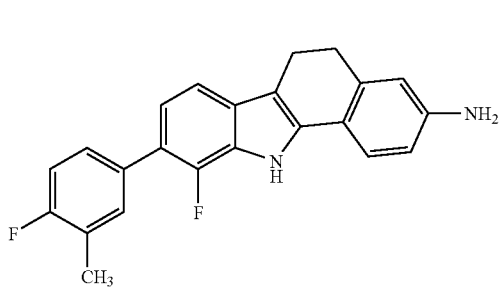

A sample of [10-Fluoro-9-(4-fluoro-3-methyl-phenyl)-5,11-dihydro-6H-benzo[a]carbazol-3-yl]-carbamic acid tert-butyl ester (example 89) (33 mg, 0.072 mmol) is treated with dichloromethane (1 mL) and trifluoroacetic acid (1 mL) and stirred for 2 hours at room temperature. The reaction is then concentrated and purified by reverse phase mass triggered HPLC to afford the TFA salt of the title compound. LC/MS calculated for [M+H]+ $C_{23}H_{19}F_2N_2$: 361.4, found: 361.2.

Example 91

N-[10-Fluoro-9-(4-fluoro-3-methyl-phenyl)-5,11-dihydro-6H-benzo[a]carbazol-3-yl]-methanesulfonamide

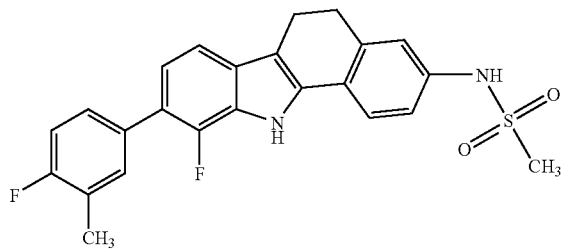

A sample of 10-Fluoro-9-(4-fluoro-3-methyl-phenyl)-5,11-dihydro-6H-benzo[a]carbazol-3-ylamine trifluoroacetate (example 90) (17.8 mg, 0.038 mmol) is treated with dichloromethane (1 mL) and pyridine (0.5 mL). The reaction is then treated with methanesulfonyl chloride (8.6 mg, 7.5 mmol) and the reaction is stirred overnight at room temperature. The reaction is then concentrated and purified by reverse phase mass triggered HPLC to afford the title compound as a white solid after lyophilization: $^1$H NMR (400 MHz, d$_6$-DMSO) δ 11.82 (s, 1H), 11.21 (s, 1H), 7.79 (d, J=8.2 Hz, 1H), 7.55 (m, 2H), 7.45 (m, 1M), 7.38 (m, 1H), 7.32 (d, J=8.1 Hz, 1H), 7.20 (m, 1H), 7.02 (dd, J=8.0, 7.0 Hz, 1H), 2.95 (m, 2H), 2.87 (m, 2H), 2.26 (s, 3H), 1.29 (s, 3H); LC/MS calculated for [M+H$_3$O]+ $C_{24}H_{23}F_2N_2O_3S$: 457.1, found: 457.0.

Example 92

N-[6-Fluoro-7-(4-fluoro-3-methyl-phenyl)-5,10-dihydro-indeno[1,2-b]indol-2-yl]-methanesulfonamide

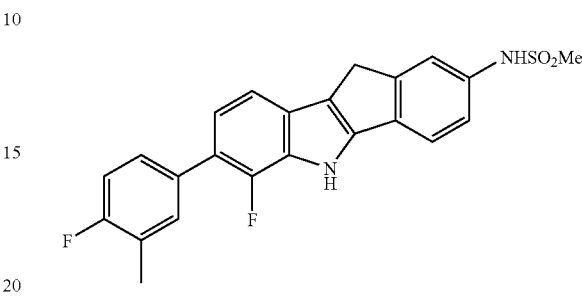

Step 1: N-(1-Oxo-indan-5-yl)-methanesulfonamide

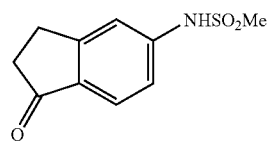

A sample of 5-Amino-indan-1-one (100 mg, 0.68 mmol) is treated with a solution pyridine (59 mg, 0.75 mmol) in a mixture of dichloromethane (1.5 mL) and tetrahydrofuran (1.5 mL). The reaction is then cooled in an ice bath. A solution of methanesulfonyl chloride (86 mg, 0.75 mmol) in tetrahydrofuran (1.5 mL) is added dropwise and the reaction is allowed to stir for 2 hours at ice bath temperature and overnight at room temperature. The reaction is diluted with ethyl acetate and extracted twice with 1 M HCl. The organics are dried over MgSO4 and the solvent is removed to afford the title material (64 mg, 42% yield) which is not purified but carried on as is: LC/MS calculated for [M+H]+ $C_{10}H_{11}NO_3S$: 226.0, found: 226.0.

Step 2: The title material is prepared in 29% yield by reacting N-(1-Oxo-indan-5-yl)-methanesulfonamide and (4'-Fluoro-3'-methyl-biphenyl-3-yl)-hydrazine hydrochloride (prepared as in example 70, steps 1 and 2 except using 3-methyl-4-fluorophenylboronic acid and 3-chloro-2-fluoroaniline as the coupling partners) in an analogous manner to example 1, step 3 except that purification is accomplished by reverse phase UV triggered HPLC: $^1$H NMR (400 MHz, d$_6$-DMSO) δ 12.08 (s, 1H), 9.75 (s, 1H), 7.61 (d, J=8.1 Hz, 1H), 7.55-7.50 (m, 1H), 7.48-7.40 (m, 3H), 7.28-7.22 (m, 2H), 7.14-7.09 (m, 1H), 3.74 (s, 2H), 3.01 (s, 3H), 2.34-2.31 (m, 3H); LC/MS calculated for [M+H]+ $C_{23}H_{18}F_2N_2O_2S$: 425.1, found: 425.1.

Example 93

N-[6-Fluoro-7-(4-fluoro-3-methyl-phenyl)-5,10-dihydro-indeno[1,2-b]indol-2-yl]-methanesulfonamide

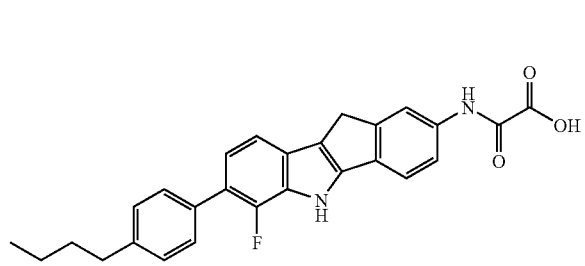

This material is prepared in a similar manner to example 92 except that in step 1, the acylation agent is oxalyl chloride and in step 2, the hydrazine is (4'-Butyl-2-fluoro-biphenyl-3-yl)-hydrazine hydrochloride (example 78, step 1); LC/MS calcd. for [M]$^+$ C$_{27}$H$_{23}$FN$_2$O$_3$: 442.2, found: 442.1.

Example 94

N-[10-Fluoro-9-(4-fluoro-3-methyl-phenyl-5,11-dihydro-6H-benzo[a]carbazol-3-yl]-acetamide

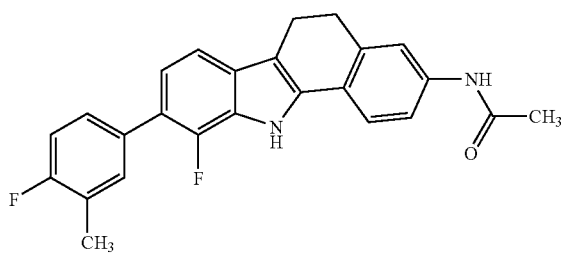

A sample of 10-Fluoro-9-(4-fluoro-3-methyl-phenyl)-5,11-dihydro-6H-benzo[a]carbazol-3-ylamine trifluoroacetate (example 88) (16.5 mg, 0.035 mmol) is treated with dioxane (1 mL) and acetic anhydride (43 mg, 0.42 mmol) and warmed to 50° C. overnight. The reaction is cooled to room temperature and concentrated and purified by reverse phase mass triggered HPLC to afford the title compound as a white solid after lyophilization: $^1$H NMR (400 MHz, d$_6$-DMSO) δ 12.49 (s, 1H), 10.21 (s, 1H), 8.63 (d, J=8.7 Hz, 1H), 8.37 (s, 1H), 8.18 (d, J=8.7 Hz, 1H), 8.02 (d, J=8.1 Hz, 1H), 7.75 (d, J=8.2 Hz, 1H), 7.59 (m, 1H), 7.53 (s, 1H), 7.30 (m, 1H), 2.97 (m, 2H), 2.91 (m, 2H), 2.35 (s, 3H), 2.13 (s, 3H); LC/MS calculated for [M+H]$^+$ C$_{25}$H$_{21}$F$_2$N$_2$O: 403.4, found: 403.1.

Example 95

N-[7-(4-Butyl-phenyl)-6-fluoro-5,10-dihydro-indeno[1,2-b]indol-2-yl]-hydroxy-acetamide

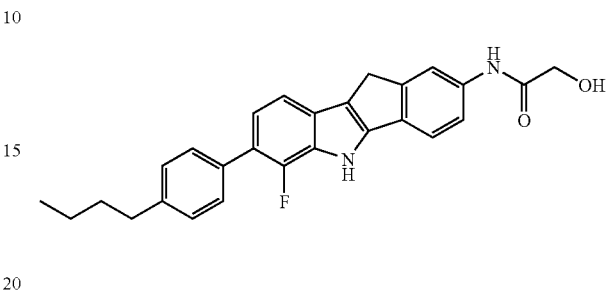

Step 1: Acetic acid (1-oxo-indan-5-ylcarbamoyl)-methyl ester

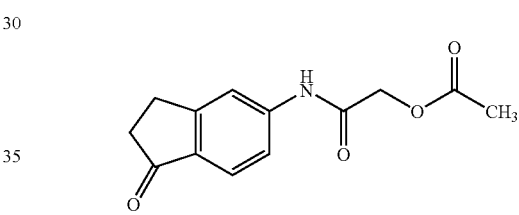

To a solution of 5-Amino-indan-1-one (commercially available, 100 mg, 0.679 mmol, 1 eq.) in DCM (5 mL) is added pyridine (0.066 mL, 0.815 mmol, 1.2 eq.). The resulting solution is cooled to 0° C. followed by the addition of acetoxy acetyl chloride (0.073 mL, 0.679 mmol, 1 eq.). After stirring at 0° C. for 15 min., the reaction is warmed to 25° C. and stirred for 12 h. The reaction is diluted with DCM and sequentially washed with 1 N HCl (aq) and saturated aqueous NaHCO$_3$. The resulting organic solution is dried over Na$_2$SO$_4$. After concentration, the residue is purified by silica gel chromatography (1:6 hexanes/EtOAc) to give Acetic acid (1-oxo-indan-5-ylcarbamoyl)-methyl ester as an off-white solid (136 mg, 81% yield). [MS: (ES$^+$) 248.1 (M+1)$^+$].

Steps 2 and 3: The title material is prepared by reacting (1-Oxo-indan-5-yl)-carbamic acid methyl ester and (4'-Butyl-2-fluoro-biphenyl-3-yl)-hydrazine hydrochloride (example 78, step 1) in an analogous manner to example 1, step 3 followed by hydrolysis as in example 2 and purification by reverse phase mass triggered HPLC: $^1$H NMR (DMSO-d6) δ 12.01 (s, 1H), 9.70 (s, 1H), 8.00 (s, 1H), 7.68 (d, 1H), 7.63-7.54 (m, 3H), 7.41 (d, 1H), 7.29 (d, 2H), 7.11 (dd, 1H), 5.70 (bs, 1H), 4.03 (s, 2H), 3.75 (s, 2H), 2.64 (t, 2H), 1.68-1.60 (m, 2H), 1.41-1.32 (m, 2H), 0.94 (t, 3H); LC/MS calculated for [M+H]$^+$ C$_{27}$H$_{25}$FN$_2$O$_2$: 429.2, found: 429.2.

Example 96

7-(4-Butyl-phenyl-6-fluoro-5,10-dihydro-indeno[1,2-b]indol-2-yl]-carbamic acid methyl ester

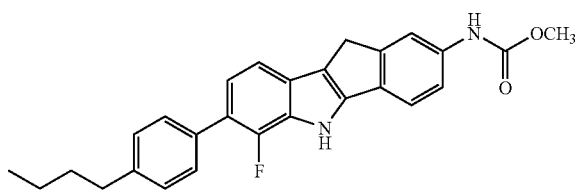

Step 1: (1-Oxo-indan-5-yl)-carbamic acid methyl ester

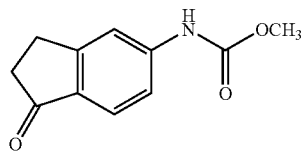

To a suspension of 5-Amino-indan-1-one (commercially available, 100 mg, 0.679 mmol, 1 eq.) in a 2:1 v/v mixture of EtOAc/H$_2$O (6 mL) is added NaHCO$_3$ (114 mg, 1.36 mmol, 2 eq.). The resulting mixture is cooled to 0° C. followed by the addition of methyl chloroformate (0.052 mL, 0.679 mmol, 1 eq.). After stirring at 0° C. for 15 min., the reaction is warmed to 25° C. and stirred for 12 h. The reaction is diluted with EtOAc and sequentially washed with 1 N HCl (aq) and saturated aqueous NaCl. The resulting organic solution is dried over Na$_2$SO$_4$ and concentrated to give (1-Oxo-indan-5-yl)-carbamic acid methyl ester as a tan solid (124 mg, 89% yield). [MS: (ES$^+$) 206.1 (M+1)$^+$].

Step 2: The title material is prepared by reacting (1-Oxo-indan-5-yl)-carbamic acid methyl ester and (4'-Butyl-2-fluoro-biphenyl-3-yl)-hydrazine hydrochloride (example 78, step) in an analogous manner to example 1, step 3 except that purification is accomplished by reverse phase mass triggered HPLC: $^1$H NMR (Acetone-d6) δ 11.09 (s, 1H), 8.76 (s, 1H), 7.90 (s, 1H), 7.67-7.54 (m, 4H), 7.47 (d, 1H), 7.32 (d, 2H), 7.18 (dd, 1H), 3.79 (s, 2H), 3.75 (s, 3H), 2.72 (t, 2H), 1.72-1.64 (m, 2H), 1.49-1.38 (m, 2H), 0.96 (t, 3H); LC/MS calculated for [M+H]$^+$ C$_{27}$H$_{25}$FN$_2$O$_2$: 429.2, found: 429.2.

Example 97

[10-Fluoro-9-(4-fluoro-3-methyl-phenyl)-5,11-dihydro-6H-benzo[a]carbazol-3-yl]-urea

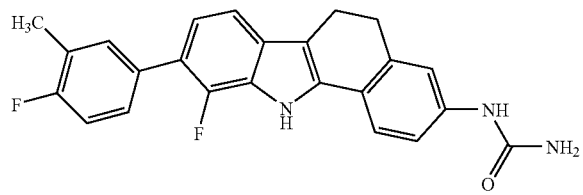

A sample 6-Fluoro-7-(4-fluoro-3-methyl-phenyl)-5,10-dihydro-indeno[1,2-b]indole-2-carboxylic acid (example 61) (30 mg, 0.075 mmol) is treated with toluene (1 mL), diphenylphosphoryl azide (22.2 mg, 0.081 mmol) and triethylamine (8.2 mg, 8.1 mmol) and heated to reflux with stirring for 2 hours. The reaction is then treated with concentrated ammonia and heated under reflux overnight. The reaction is then concentrated by rotary evaporation and purified using a UV triggered HPLC to afford 8.4 mg (27% yield) of [10-Fluoro-9-(4-fluoro-3-methyl-phenyl)-5,11-dihydro-6H-benzo[a]carbazol-3-yl]-urea; LC/MS calcd. for [M+H]$^+$ C$_{24}$H$_{20}$F$_2$N$_3$O: 404.2, found: 404.0.

Example 98

[7-(4-Butyl-phenyl)-6-fluoro-5,10-dihydro-indeno[1,2-b]indol-2-yl]-urea

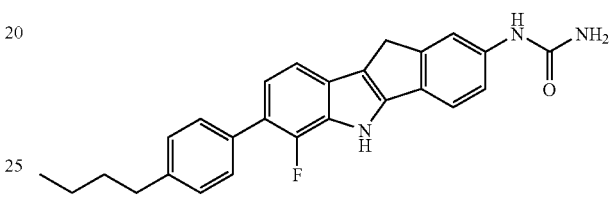

Step 1: 7-(4-Butyl-phenyl)-6-fluoro-5,10-dihydro-indeno[1,2-b]indol-2-ylamine

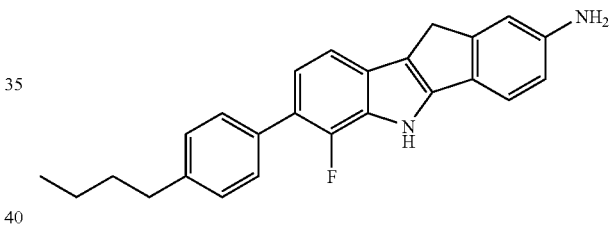

The title material is prepared in 17% yield by reacting 5-Amino-indan-1-one (commercially available) and (4'-Butyl-2-fluoro-biphenyl-3-yl)-hydrazine hydrochloride (Example 78, step) in an analogous manner to example 1, step 3; LC/MS calculated for [M+H]$^+$ C$_{25}$H$_{23}$FN$_2$: 371.2, found: 371.2.

Step 2: To a suspension of 7-(4-Butyl-phenyl)-6-fluoro-5,10-dihydro-indeno[1,2-b]indol-2-ylamine (25 mg, 0.068 mmol, 1 eq.) in a 1:1 v/v mixture of AcOH/H$_2$O (1 mL) is added a solution of NaOCN (4.4 mg, 0.068 mmol, 1 eq.) in H$_2$O (1 mL). The resulting mixture is stirred at 25° C. for 2 h, at which point an additional NaOCN (4.4 mg, 0.068 mmol, 1 eq.) is added to the reaction. The resulting mixture is stirred at 25° C. for an additional 12 h. The reaction is diluted with EtOAc and sequentially washed with H$_2$O, saturated aqueous NaHCO$_3$, and saturated aqueous NaCl. The resulting organic solution is dried over Na$_2$SO$_4$. After concentration, the crude product is purified by preparative RP LC-MS to give [7-(4-Butyl-phenyl)-6-fluoro-5,10-dihydro-indeno[1,2-b]indol-2-yl]-urea (10 mg, 36% yield): $^1$H NMR (Acetone-d6) δ 11.09 (s, 1H), 8.26 (s, 1H), 7.89 (s, 1H), 7.59 (d, 2H), 7.58 (s, 1H), 7.48 (d, 1H), 7.42 (d, 1H), 7.33 (d, 2H), 7.18 (dd, 1H), 5.53 (bs), 3.72 (s, 2H), 2.72 (t, 2H), 1.72-1.64 (m, 2H), 1.49-1.36 (m, 2H), 0.96 (t, 3H); LC/MS calculated for [M+H]$^+$ C$_{26}$H$_{24}$FN$_3$O: 414.2, found: 414.2.

Example 99

N-[9-(4-Butyl-phenyl)-10-fluoro-5,11-dihydro-6H-benzo[a]carbazole-3-carbonyl]-methanesulfonamide

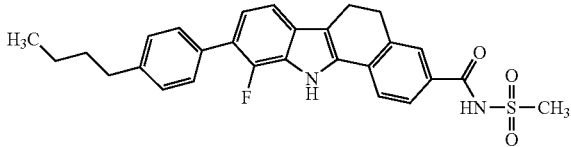

Step 1: N-(5-Oxo-5,6,7,8-tetrahydro-naphthalene-2-carbonyl)-methanesulfonamide

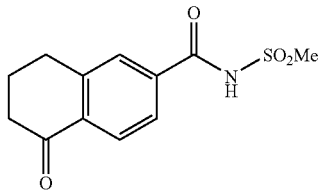

A sample of 5-Oxo-5,6,7,8-tetrahydro-naphthalene-2-carboxylic acid amide (Example 81, Step 1) (29.4 mg, 0.16 mmol) in tetrahydrofuran (71 μL) is treated with $K_2CO_3$ (36.5 mg, 0.26 mmol), powdered KOH (32.9 mg, 0.82 mmol) and tetrabutylammonium hydrogen sulfate (2.6 mg, 0.008 mmol) in that order. The reaction is warmed to 55° C. and vigorously stirred for 20 minutes. Then a solution of methanesulfonyl chloride (23.2 mg, 0.20 mmol) in tetrahydrofuran (140 μL) is added over 20 minutes and the reaction was stirred at 55° C. overnight. The reaction is then cooled to room temperature, diluted with ethyl acetate and extracted with water twice. The organic phase is then dried over $MgSO_4$, filtered and the solvent is removed. The crude sulfonamide (35.5 mg 86% yield) is taken on without purification; LC/MS calculated for $[M+H]^+$ $C_{12}H_{13}NO_4S$: 268.1, found: 268.1.

Step 2: The title material is prepared in 45% yield by reacting 5-Amino-indan-1-one (commercially available) and (4'-Butyl-2-fluoro-biphenyl-3-yl)-hydrazine hydrochloride (Example 78, step 1) in an analogous manner to example 1, step 3; LC/MS calcd. for $[M+H]^+$ $C_{28}H_{28}FN_2O_3S$: 491.6, found: 491.1.

Example 100

3-Acetylamino-7-(4-butyl-phenyl)-6-fluoro-5,10-dihydro-indeno[1,2-b]indole-2-carboxylic acid

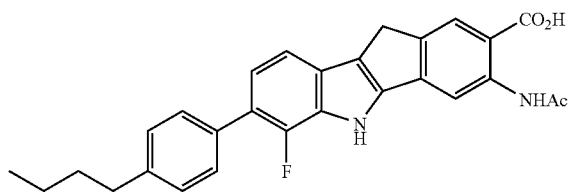

Step 1: 6-Nitro-5-vinyl-indan-1-one

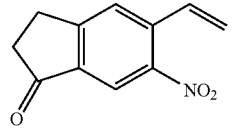

A solution of 5-bromo-6-nitro-indan-1-one (58 mg, 0.23 mmol), (*J. Med. Chem.*, 2003, 46, 399-408), vinylboronic acid dibutyl ester (74 μL, 0.34 mmol), $Pd(PPh_3)_2Cl_2$ (7.8 mg, 0.0011 mmol), and $Na_2CO_3$ (167 mg, 1.57 mmol) in 4:1 $THF/H_2O$ (1.4 mL/360 μL) was heated to 80° C. overnight. The crude reaction was filtered over Celite and extracted with EtOAC. The organic phase was dried ($MgSO_4$), filtered, and concentrated. The crude material was chromatographed ($SiO_2$) to afford 36 mg (79%) of 6-Nitro-5-vinyl-indan-1-one; LC/MS calculated for $[M+H]^+$ $C_{11}H_9NO_2$: 204.1, found: 204.1.

Step 2: 6-Nitro-1-oxo-indan-5-carboxylic acid

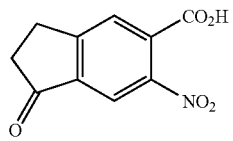

A solution of 6-nitro-5-vinyl-indan-1-one (36 mg, 0.18 mmol), $RuCl_3 \cdot H_2O$ (1.8 mg, 8.9 μmol), and $NaIO_4$ (152 mg, 0.713 mmol) in a mixture of $CCl_4$ (300 μL), $H_2O$ (445 μL), and acetonitrile (300 μL) was heated to 50° C. for 2 hours and then cooled to RT and filtered over Celite and concentrated in vacuo. The crude carboxylic acid was purified by mass-triggered HPLC to afford 26 mg (66%) of 6-Nitro-1-oxo-indan-5-carboxylic acid; LC/MS calculated for $[M+H]^+$ $C_{10}H_7NO_5$: 222.0, found: 222.0.

Step 3: 7-(4-Butyl-phenyl)-6-fluoro-3-nitro-5,10-dihydro-indeno[1,2-b]indole-2-carboxylic acid

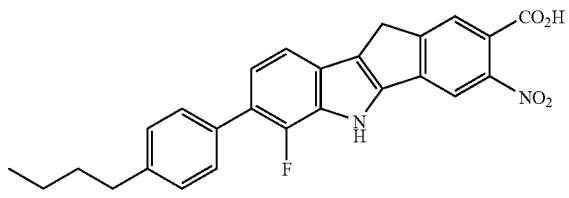

A sealable reaction vial was charged with 6-nitro-1-oxo-indan-5-carboxylic acid (26 mg, 0.12 mmol), (4'-Butyl-2-fluoro-biphenyl-3-yl)-hydrazine hydrochloride (example 78, step 1) (25 mg, 0.12 mmol), zinc (II) chloride (24 mg, 0.18 mmol), and acetic acid (1.5 mL), sealed, and heated to 105° C. overnight. Reaction was then cooled to RT, concentrated in vacuo, and purified by UV-triggered HPLC to afford 22 mg (41%) of 7-(4-Butyl-phenyl)-6-fluoro-3-nitro-5,10-dihydro-indeno[1,2-b]indole-2-carboxylic acid; LC/MS calculated for $[M+H]^+$ $C_{26}H_{21}FN_2O_4$: 445.1, found: 445.1.

Steps 4 and 5: A solution of 7-(4-butyl-phenyl)-6-fluoro-3-nitro-5,10-dihydro-indeno[1,2-b]indole-2-carboxylic acid (20 mg, 0.055 mmol) in ethanol (2 mL) and THF (1 mL) was treated with 10% Pd/C-DeGussa type (5 mg) and subjected to $H_2$ (g) bubble for 15 min. The reaction was maintained under an atmosphere of $H_2$ (g) overnight and then filtered over Celite and concentrated. LC/MS calculated for $[M+H]^+$ $C_{26}H_{23}FN_2O_2$: 415.2, found: 415.2. The crude amino-compound was diluted in THF (1 mL), cooled to 0° C., and treated with $Et_3N$ (16 mL, 0.12 mmol) followed by acetic anhydride (11 mL, 0.12 mmol). The reaction warmed to RT, stirred overnight, and was concentrated and purified by UV-triggered HPLC to afford 4.4 mg (17%) of the desired titled compound; $^1H$ NMR (400 MHz, $d_6$-DMSO) δ 12.43 (s, 1H), 11.45 (s, 1H), 8.92 (s, 1H), 8.14 (s, 1H), 7.54 (m, 2H), 7.50 (d, J=8.2 Hz, 1H), 7.31 (d, J=8.1 Hz, 2H), 7.17 (dd, J=8.0, 7.3 Hz, 1H), 3.77 (s, 2H), 2.64 (t, J=7.6 Hz, 2H), 2.20 (s, 3H), 1.61 (m, 2H), 1.35 (m, 2H), 0.93 (t, J=7.3 Hz, 3H); LC/MS calcd. for $[M+H]^+$ $C_{28}H_{28}FN_2O_3S$: 491.2, found: 491.1.

Example 101

10-(4-Butyl-phenyl)-11-fluoro-5,6,7,12-tetrahydro-benzo[6,7]cyclohepta[1,2-b]indole-3-carboxylic acid

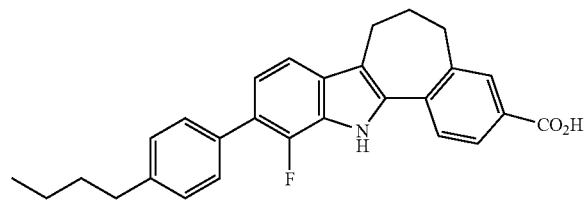

The title material is prepared in 34% yield by reacting 5-Oxo-6,7,8,9-tetrahydro-5H-benzocycloheptene-2-carboxylic acid (*J. Org. Chem.* 1962, 27(1), p 70-76) and (4'-Butyl-2-fluoro-biphenyl-3-yl)-hydrazine hydrochloride (prepared as in example 69, steps 1 and 2 except using 4-n-butylphenylboronic acid as the coupling partner) in an analogous manner to example 1, step 3 except that purification is accomplished by reverse phase mass triggered HPLC: $^1H$ NMR (Acetone-d6) δ 10.72 (bs, 1H), 8.09 (d, 1H), 7.99 (d, 1H), 7.92 (s, 1H), 7.58 (d, 2H), 7.45 (d, 1H), 7.31 (d, 2H), 7.17 (dd, 1H), 3.18 (t, 2H), 3.10-3.04 (m, 2H), 2.72 (t, 2H), 2.22-2.14 (m, 2H), 1.73-1.64 (m, 2H), 1.45-1.38 (m, 2H), 0.96 (t, 3H); LC/MS calculated for $[M+H]^+$ $C_{28}H_{26}FNO_2$: 428.2, found: 428.2.

Example 102

9-(4-Butyl-phenyl)-5,5-dioxo-6,11-dihydro-5H-5l6-thia-11-aza-benzo[a]fluorene-3-carboxylic acid

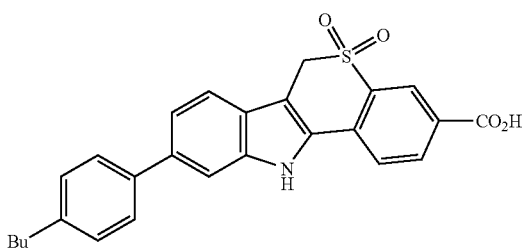

Step 1: 1,1,4-Trioxo-1,6-thiochroman-7-carboxylic acid methyl ester

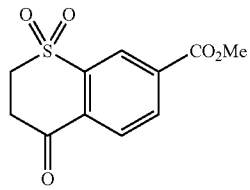

A sample of the known (US2003158413) 4-Oxo-thiochroman-7-carboxylic acid methyl ester (24.2 mg, 0.11 mmol) is treated with a solution of 30% aqueous hydrogen peroxide (30 mg, 0.26 mmol) in acetic acid (1 mL). The reaction is then heated to 100° C. for 1.5 hours and the solvent is removed to afford the title material which was not purified but carried on as is: LC/MS calculated for $[M+H]^+$ $C_{11}H_{10}O_5S$: 254.0, found: 254.1.

Step 2: The crude material from step 1 is treated with (4'-Butyl-biphenyl-3-yl)-hydrazine hydrochloride (example 70, step 2) (39 mg, 0.142 mmol) and zinc chloride (37 mg, 0.27 mmol) and acetic acid (1 mL) and heated to 105° C. overnight. After cooling, the reaction was treated with ethyl acetate and water. There are solids that did not dissolve but are suspended in the ethyl acetate. The organics are washed with water once more and then drained into a flask along with the solids. The solvent is removed and the crude mixture is dissolved in hot dioxane (5 mL) and treated with ethanol (3 mL), water (1 mL) and excess lithium hydroxide (~100 mg). The reaction is stirred at 70° C. for 2 hours, cooled to room temperature and acidified with 1 M HCl until acidic. The solvent is removed and the reaction is partitioned between ethyl acetate and water. The aqueous phase is discarded. The organics are extracted with water 3 times and discarded. The basic extracts are acidified with concentrated HCl and extracted with ethyl acetate twice. The combined organics are dried over MgSO4 and the solvent is removed. The residue is purified by UV triggered reverse phase HPLC to afford the title material as a white solid. The material is contaminated with ~15% of 7-(4-Butyl-phenyl)-5,5-dioxo-6,11-dihydro-5H-5l6-thia-11-aza-benzo[a]fluorene-3-carboxylic acid. NMR data are given for the title material only; $^1H$ NMR (400 MHz, DMSO-$d_6$) δ 12.30 (s, 1H), 8.39-8.31 (m, 2H), 8.15-8.10 (m, 1H), 7.82-7.77 (m, 1H), 7.68 (s, 1H), 7.64 (d, J=8.1 Hz, 1H), 7.47-7.44 (m, 1H), 7.36 (s, 1H), 7.31 (d, J=8.1 Hz, 1H), 5.12 (s, 2H), 2.64 (dd, J=7.6, 7.6 Hz, 2H), 1.64-1.56 (m, 2H), 1.39-1.29 (m, 2H), 0.93 (dd, J=7.3, 7.3 Hz, 3H); ESIMS m/z for $(M^++H^+)$ calculated 446.1, found 446.1.

Example 103

10-Fluoro-9-(4-fluoro-3-methyl-phenyl)-6,11-dihydro-5-oxa-11-aza-benzo[a]fluorene-3-carboxylic acid amide

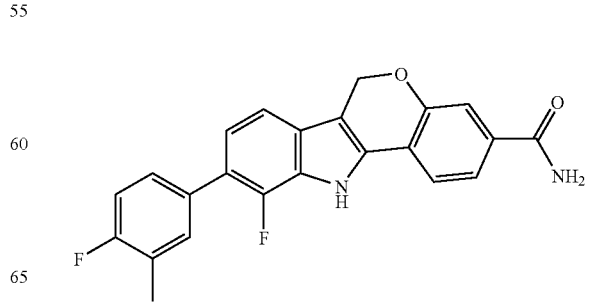

Step 1: 7-Hydroxy-chroman-4-one

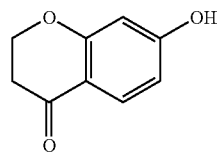

To a stirred mixture of resorcinol (5 g, 45.5 mmol) and 3-chloropropionic acid (5.2 g, 48 mmol), is added trifluoromethanesulfonic acid (25 g, 166 mmol) in one portion. The mixture is stirred at room temperature for 10 min, then heated at 80° C. for 30 min. The reaction is cooled to room temperature and the mixture is diluted with DCM (200 mL). The solution is slowly poured into ice water (200 mL). The bilayer is separated, and the aqueous phase is extracted with DCM (2×40 mL). The combined organic phase is washed with brine and dried over sodium sulfate. The crude 3-chloro-1-(2,4-dihydroxy-phenyl)-propan-1-one is obtained as orange solid (6.9 g) after evaporation of solvent and carried on as is.

The crude 3-chloro-1-(2,4-dihydroxy-phenyl)-propan-1-one (6.9 g) is dissolved in sodium hydroxide (2N, 100 mL) at 0° C. The solution is stirred for 2 h and acidified with HCl (5N) to pH=3. The mixture is extracted with ethyl acetate (3×50 mL). The combined organic phase is washed with brine and dried over sodium sulfate. After evaporation of solvent, 7-hydroxy-chroman-4-one is obtained as yellow solid: $^1$H NMR (400 MHz, MeOD) δ 7.70 (d, 1H, J=8.8 Hz), 6.47 (dd, 1H, J=2.4, 8.8 Hz), 6.30 (d, 1H, J=2.0 Hz), 4.47 (t, 2H, J=6.4 Hz), 2.70 (t, 2H, J=6.4 Hz).

Step 2: 4-Oxo-chroman-7-carbonitrile

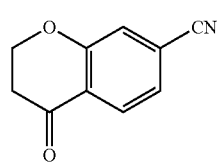

By following the same sequence of transformations as described in example 81, steps 4 and 5,4-oxo-chroman-7-carbonitrile is obtained as a white solid: $^1$H NMR (400 MHz, CDCl$_3$) δ 7.98 (d, 1H, J=8 Hz), 7.30 (s, 1H), 7.27 (d, 1H, J=8 Hz), 4.60 (t, 1H, J=6.4 Hz), 2.88 (t, 1H, J=6.4 Hz).

Step 3: A sample of 4-oxo-chroman-7-carbonitrile and (4'-Fluoro-3'-methyl-biphenyl-3-yl)-hydrazine hydrochloride (prepared as in example 70, steps 1 and 2 except using 3-methyl-4-fluorophenylboronic acid as the coupling partner) are reacted together as in example 1, step 3. The crude product is then subjected to hydrolysis as in example 19, step 3 to afford 10-Fluoro-9-(4-fluoro-3-methyl-phenyl)-6,11-dihydro-5-oxa-11-aza-benzo[a]fluorene-3-carboxylic acid amide as yellow solid: $^1$H NMR (400 MHz, MeOD) δ 7.68 (d, 1H, J=8 Hz), 7.51 (dd, 1H, J=2, 8 Hz), 7.48-7.39 (m, 2H), 7.29 (d, 1H, J=8 Hz), 7.14-7.08 (m, 2H), 5.64 (s, 2H), 2.33 (d, 3H, J=1.6 Hz). ESMS m/z 390.1 (M+H$^+$).

Example 104

N-[7-(4-Butyl-phenyl-6-fluoro-5,10-dihydro-indeno[1,2-b]indol-2-yl]-methanesulfonamide

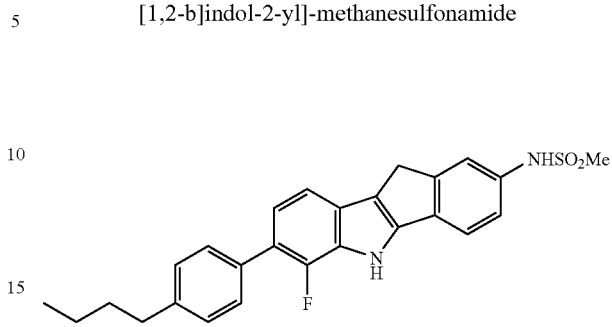

The title material is prepared in a similar manner to example 92 except that in step 2, the hydrazine is (4'-Butyl-2-fluoro-biphenyl-3-yl)-hydrazine hydrochloride (example 78, step 1): $^1$H NMR (400 MHz, Acetone-d6) δ 11.17 (bs, 1H), 8.59 (bs, 1H), 7.69 (d, 1H), 7.62 (s, 1H), 7.58 (d, 2H), 7.46 (d, 1H), 7.36 (d, 1H), 7.32 (d, 2H), 7.19 (dd, 1H), 3.82 (s, 2H), 3.05 (s, 3H), 2.69 (t, 2H), 1.71-1.62 (m, 2H), 1.50-1.40 (m, 2H), 0.98 (t, 3H); ESMS m/z 449.2 (M+H$^+$).

Example 105

N-[9-(4-Butyl-phenyl-10-fluoro-5,11-dihydro-6H-benzo[a]carbazol-3-yl]-2-hydroxy-acetamide

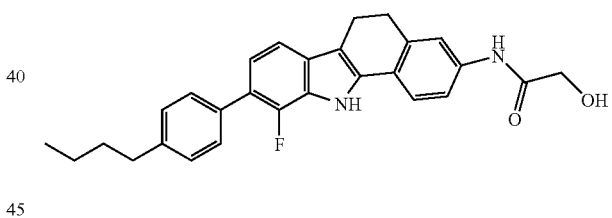

The title material is prepared in a similar manner to example 95 utilizing appropriate starting materials: ESMS m/z 443.2 (M+H$^+$).

Example 106

N-[9-(4-Butyl-phenyl)-10-fluoro-5,11-dihydro-6H-benzo[a]carbazol-3-yl]-methanesulfonamide

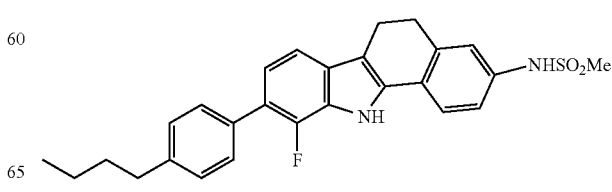

The title material is prepared in a similar manner to example 92 utilizing appropriate starting materials: ESMS m/z 463.2 (M+H⁺).

Example 107

N-[7-(4-Diethylamino-phenyl)-6-fluoro-5,10-dihydro-indeno[1,2-b]indol-2-yl]-acetamide

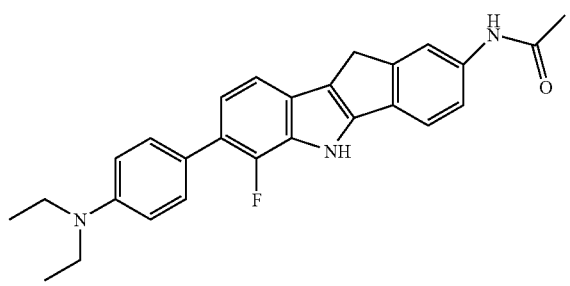

Step 1: Diethyl-[4-(4,4,5,5-tetramethyl-[1,3,2]dioxaborolan-2-yl)-phenyl]-amine

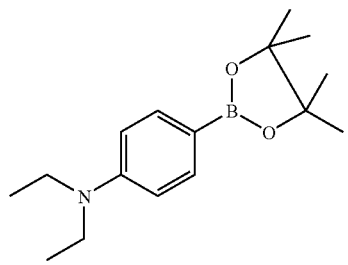

4-(4,4,5,5-Tetramethyl-[1,3,2]dioxaborolan-2-yl)-phenylamine (500 mg, 2.28 mmol, 1 eq.) is dissolved in anhyd. DMF (5 mL) and cooled to 0° C. NaH (60% dispersion, 201 mg, 5.02 mmol, 2.2 eq.) is added and the resulting mixture is stirred at 0° C. for 30 min after which iodoethane (0.38 mL, 2.1 eq) is added dropwise to the reaction mixture. Once this addition is complete, the reaction mixture is allowed to warm to room temperature and stir for 3 days. The reaction is diluted with EtOAc and sequentially washed with H₂O (5×) and saturated aqueous NaCl. The organic solution is dried over Na₂SO₄ and concentrated to give Diethyl-[4-(4,4,5,5-tetramethyl-[1,3,2]dioxaborolan-2-yl)-phenyl]-amine as a sticky tan solid: ESMS m/z 276.1 (M+H⁺).

Step 2: The product from step 1 (200 mg, 0.7268 mmol), 3-bromo-2-fluoro-phenylamine (165 mg, 0.7268 mmol, 1 eq.), Na₂CO₃ (616 mg, 5.814 mmol. 8 eq.) and Pd(PPh₃)₄ (84 mg, 0.1 eq.) are partially dissolved in a mixture of DMF (10 mL) and H₂O (2 mL). N₂ gas is bubbled through this reaction mixture for 5 minutes. The resulting mixture is heated to 150° C. in a sealed tube under microwave irradiation for 10 min. The reaction is diluted with EtOAc and sequentially washed with H₂O, 1 N NaOH (aq), and saturated aqueous NaCl. The organic solution is dried over Na₂SO₄ and concentrated. The resulting residue is purified on silica gel (2:1 hexanes/EtOAc) to afford the aniline product as a yellow oil. ESMS m/z 259.1 (M+H⁺).

Steps 3-4: The title material is prepared in a similar manner to example 1, steps 2 and 3 using the product from example 107, step 2 and commercially available N-(1-Oxo-indan-5-yl)-acetamide: ¹H NMR (400 MHz, CD3OD, TFA salt) δ 7.89 (d, 2H), 7.81 (s, 1H), 7.61 (d, 2H), 7.56-7.48 (m, 2H), 7.42 (d, 1H), 7.13 (dd, 1H), 3.78-3.65 (m, 6H), 2.12 (s, 3H), 1.18 (t, 6H); ESMS m/z 428.2 (M+H⁺).

Examples 108-124

By repeating the procedures described in examples 17, 30, 57, 75 and/or 107, using appropriate starting materials, the following compounds identified in Table 7, are obtained.

TABLE 7

| Compound # | Structure | NMR and/or ESMS |
|---|---|---|
| 108 | 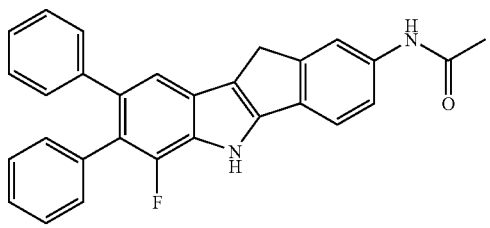 | ¹H NMR (400 MHz, DMSO-d6) δ 12.06 (bs, 1 H), 10.02 (bs, 1 H), 7.92 (s, 1 H), 7.64-7.54 (m, 2 H), 7.41 (s, 1 H), 7.31-7.12 (m, 10 H), 3.74 (s, 2 H), 2.08 (s, 3 H); ESMS m/z 415.1 (M + H⁺). |
| 109 | 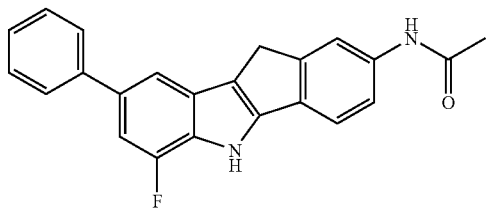 | ¹H NMR (400 MHz, Acetone-d6) δ 11.13 (bs, 1 H), 9.26 (bs, 1 H), 8.00 (s, 1 H), 7.78 (d, 2 H), 7.74 (s, 1 H), 7.62 (s, 2 H), 7.52-7.45 (m, 2 H), 7.38-7.27 (m, 1 H), 7.22 (d, 1 H), 3.78 (s, 2 H), 2.11 (s, 3 H); ESMS m/z 357.1 (M + H⁺). |

TABLE 7-continued

| Compound # | Structure | NMR and/or ESMS |
|---|---|---|
| 110 | 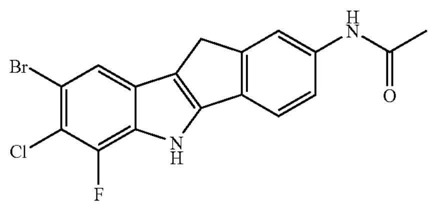 | ¹H NMR (400 MHz, DMSO-d6) δ 12.43 (bs, 1 H), 10.03 (bs, 1 H), 7.92 (s, 1 H), 7.81 (s, 1 H), 7.54 (s, 2 H), 3.71 (s, 2 H), 2.08 (s, 3 H); ESMS m/z 394.9 (M + H⁺). |
| 111 | 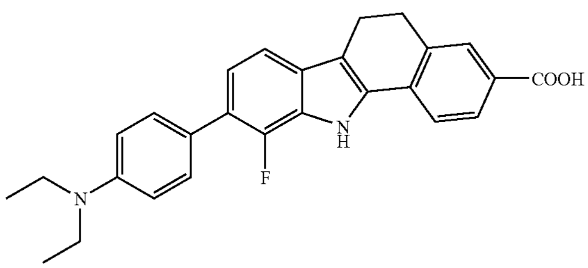 | ESMS m/z 429.2 (M + H⁺). |
| 112 | 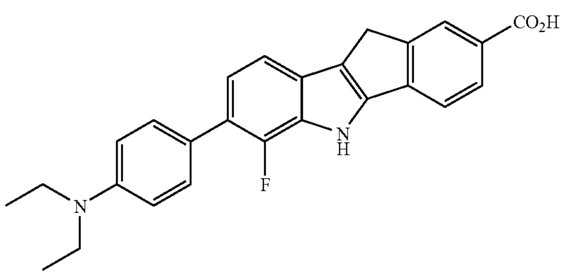 | ESMS m/z 415.2 (M + H⁺). |
| 113 | 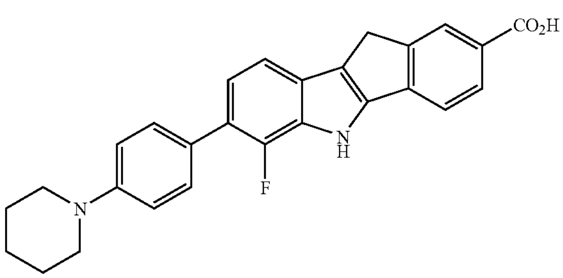 | ¹H NMR (400 MHz, DMSO-d6, TFA salt) δ 12.18 (s, 1 H), 8.10 (s, 1 H), 8.00 (d, 1 H), 7.72 (d, 1 H), 7.52-7.46 (m, 4 H), 7.16 (t, 1 H), 7.08-7.04 (m, 2 H), 3.82 (s, 2 H), 3.23 (br, 4 H), 1.66 (br, 4 H), 1.58 (br, 2 H); ESMS m/z 427.1 (M + H⁺). |
| 114 | 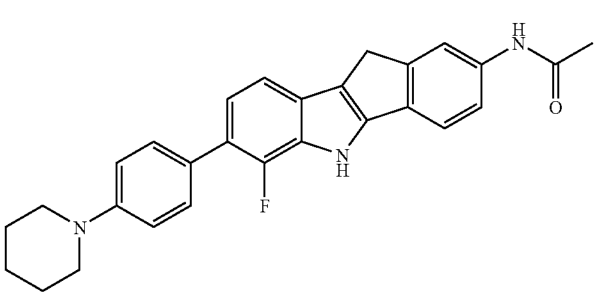 | ¹H NMR (400 MHz, CD₃OD, TFA salt) δ 7.89-7.81 (m, 3 H), 7.73 (d, 2 H), 7.60-7.50 (m, 2 H), 7.44 (d, 1 H), 7.12 (dd, 1 H), 3.75-3.65 (m, 6 H), 2.12 (s, 3 H), 2.10-2.01 (m, 4 H), 1.90-1.77 (m, 2 H); ESMS m/z 440.2 (M + H⁺). |
| 115 | 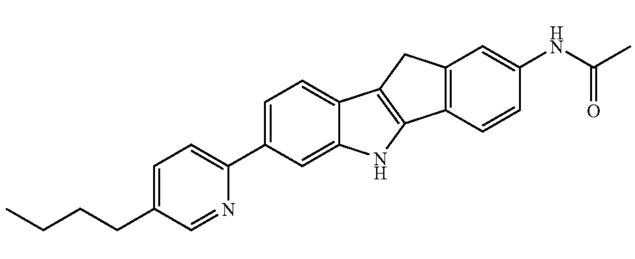 | ESMS m/z 396.3 (M + H⁺). |

TABLE 7-continued

| Compound # | Structure | NMR and/or ESMS |
|---|---|---|
| 116 | 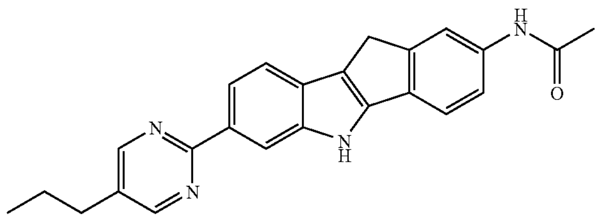 | $^1$H NMR (400 MHz, DMSO-d6) δ 11.72 (s, 1 H), 10.01 (s, 1 H), 8.87 (s, 1 H), 8.72 (s, 2 H), 8.47 (d, J = 0.9 Hz, 1 H), 8.13 (dd, J = 8.4, 1.5 Hz, 1 H), 7.89 (m, 1 H), 7.56 (m, 1 H), 4.01 (s, 2 H), 2.58 (m, 2 H), 2.08 (s, 3 H), 1.65 (m, 2 H), 0.96 (t, J = 7.2 Hz, 3 H); ESMS m/z 383.2 (M + H$^+$). |
| 117 | 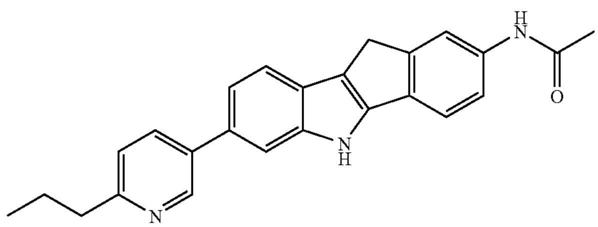 | $^1$H NMR (400 MHz, DMSO-d6) δ 11.85 (s, 1 H), 10.02 (s, 1 H), 7.89 (m, 2 H), 7.69 (d, J = 8.3 Hz, 1 H), 7.60-7.51 (m, 5 H), 7.23 (m, 1 H), 3.73 (s, 2 H), 2.95 (m, 2 H), 2.08 (s, 3 H), 1.65 (m, 2 H), 0.97 (m, 3 H); ESMS m/z 382.5 (M + H$^+$). |
| 118 | 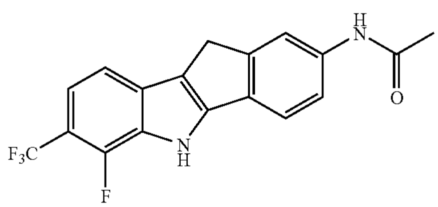 | ESMS m/z 349.1 (M + H$^+$). |
| 119 | 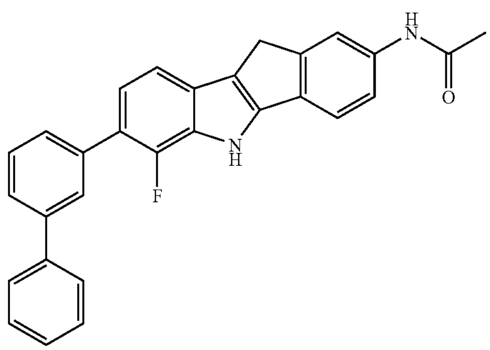 | ESMS m/z 433.5 (M + H$^+$). |
| 120 | 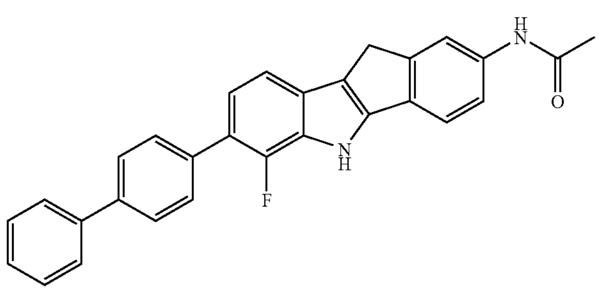 | $^1$H NMR (400 MHz, DMSO-d6) δ 12.09 (s, 1 H), 10.02 (s, 1 H), 9.92 (s, 1 H), 7.81-7.72 (m, 6 H), 7.56-7.40 (m, 6 H), 7.21 (dd, J = 7.8, 7.5 Hz, 1 H), 3.73 (s, 2 H), 2.08 (s, 3 H); ESMS m/z 433.3 (M + H$^+$). |
| 121 | 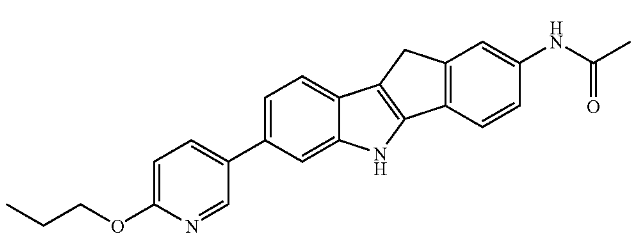 | ESMS m/z 398.2 (M + H$^+$). |

TABLE 7-continued

| Compound # | Structure | NMR and/or ESMS |
|---|---|---|
| 122 | 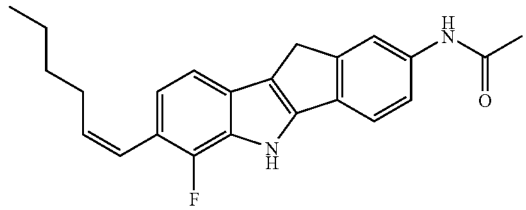 | ESMS m/z 363.1 (M + H⁺). |
| 123 | 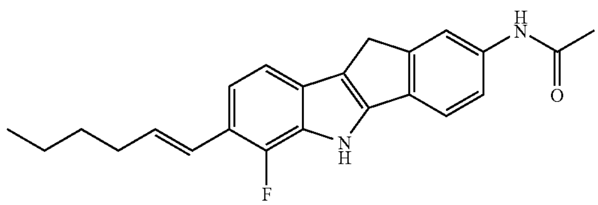 | ¹H NMR (400 MHz, DMSO-d6) δ 11.92 (s, 1 H), 9.99 (s, 1 H), 7.88 (s, 1 H), 7.51 (s, 2 H), 7.27 (m, 1 H), 7.20 (m, 1 H), 6.63 (d, J = 16.3 Hz, 1 H), 6.30 (m, 1 H), 3.67 (s, 2 H), 2.24 (m, 2 H), 2.06 (s, 3 H), 1.45 (m, 2 H), 1.36 (m, 2 H), 0.92 (t, J = 7.2 Hz, 3 H); ESMS m/z 363.4 (M + H⁺). |
| 124 | 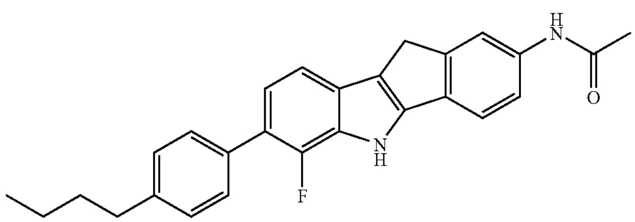 | ¹H NMR (400 MHz, DMSO-d6) δ 12.02 (s, 1 H), 10.01 (s, 1 H), 7.90 (s, 1 H), 7.54 (m, 4 H), 7.40 (d, J = 8.2 Hz, 1 H), 7.30 (d, J = 8.2 Hz, 2 H), 7.12 (dd, J = 7.9, 7.4 Hz, 1 H), 3.71 (s, 2 H), 2.63 (t, J = 7.6 Hz, 2 H), 2.07 (s, 3 H), 1.60 (m, 2 H), 1.37 (m, 2 H), 0.93 (t, J = 7.3 Hz, 3 H); ESMS m/z 413.2 (M + H⁺). |

Examples 125-136

By repeating the procedure described in example 97, quenching either with ammonia or methanol, using the appropriate carboxylic acids as starting materials (obtained by procedures described in examples 30, 57, 75, 107, and/or 143), the following compounds identified in Table 8, are obtained.

TABLE 8

| Compound # | Structure | NMR and/or ESMS |
|---|---|---|
| 125 | 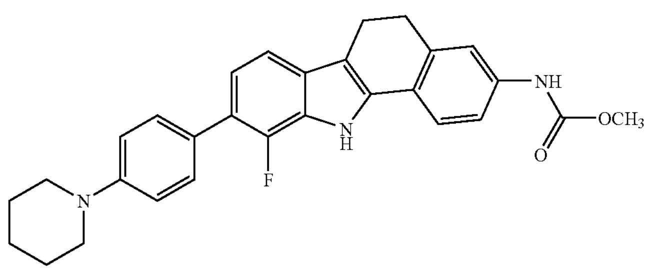 | ¹H NMR (400 MHz, DMSO-d6, HCl salt) δ 11.79 (s, 1 H), 9.94 (s, 1 H), 9.71 (s, 1 H0, 8.63 (d, 1 H), 8.17 (m, 1 H), 7.76-7.66 (m, 2 H), 7.55 (d, 1 H), 7.40-7.34 (m, 2 H), 7.13-7.11 (m, 1 H), 3.69 (s, 3 H), 3.40 (bs, 4 H), 2.98-2.87 (m, 4 H), 1.82 (bs, 4 H), 1.64 (bs, 2 H); ESMS m/z 470.1 (M + H⁺). |
| 126 | 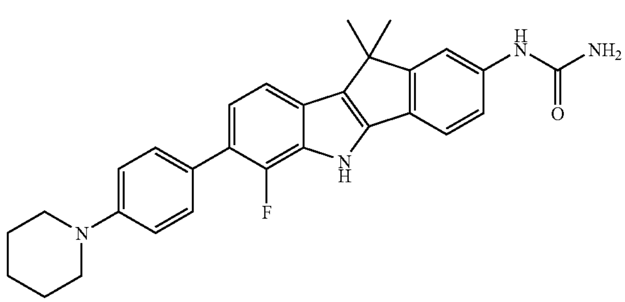 | ¹H NMR (400 MHz, DMSO-d6, HCl salt) δ 11.83 (s, 1 H), 8.62 (s, 1 H), 7.52 (bs, 2 H), 7.43-7.42 (m, 3 H), 7.29-7.28 (m, 1 H), 7.09-7.06 (m, 2 H), 5.85 (bs, 2 H), 3.30 (bs, 4 H), 1.72 (bs, 4 H), 1.60 (bs, 2 H), 1.50 (s, 6 H); ESMS m/z 469.2 (M + H⁺). |

TABLE 8-continued

| Compound # | Structure | NMR and/or ESMS |
|---|---|---|
| 127 | 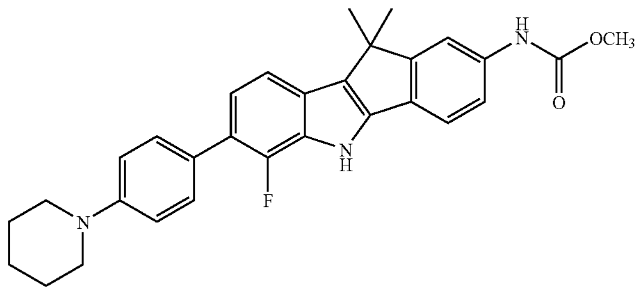 | ¹H NMR (400 MHz, Acetone-d6, TFA salt) δ 11.70 (s, 1 H), 8.73 (s, 1 H), 7.81-7.76 (m, 3 H), 7.71-7.69 (m, 2 H), 7.58-7.46 (m, 4 H), 7.20-7.16 (, 1 H), 3.73 (s, 3 H), 3.50-3.48 (m, 4 H), 1.74-1.72 (m, 4 H), 1.60 (s, 6 H), 1.62-1.59 (m, 2 H); ESMS m/z 484.2 (M + H⁺). |
| 128 | 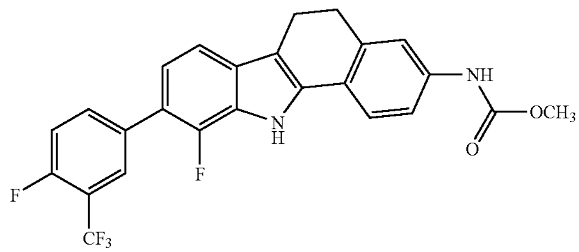 | ESMS m/z 473.1 (M + H⁺). |
| 129 | 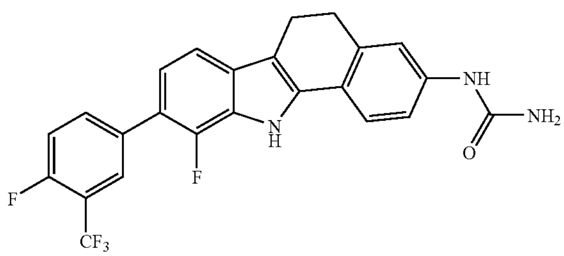 | ESMS m/z 458.1 (M + H⁺). |
| 130 | 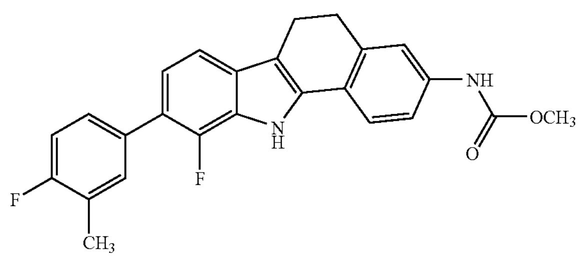 | ¹H NMR (400 MHz, DMSO-d6) δ 11.77 (s, 1 H), 9.70 (s, 1 H), 7.74 (d, 1 H), 7.51-7.49 (m, 1 H), 7.43-7.34 (m, 2 H), 7.33 (d, 1 H), 7.26-7.21 (m, 1 H), 7.07-7.04 (m, 1 H), 3.68 (s, 3 H), 2.96-2.89 (m, 4 H), 2.31 (d, 3 H); ESMS m/z 419.1 (M + H⁺). |
| 131 | 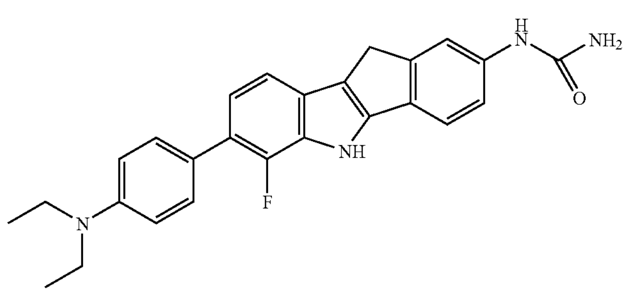 | ¹H NMR (400 MHz, DMSO-d6, HCl salt) δ 12.08 (s, 1 H), 9.76 (s, 1 H), 7.86 (bs, 2 H), 7.79 (s, 1 H), 7.53-7.50 (m, 1 H), 7.42-7.30 (m, 4 H), 7.19-7.17 (m, 2 H), 5.20 (bs, 1 H), 3.69 (s, 2 H), 3.51-3.46 (m, 4 H), 1.10 (t, 6 H); ESMS m/z 429.2 (M + H⁺). |
| 132 | 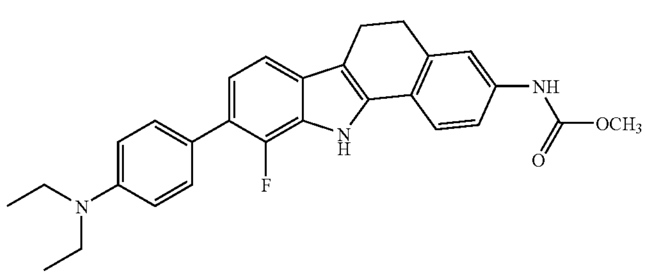 | ¹H NMR (400 MHz, DMSO-d6, HCl salt) δ 11.96 (br, 1 H), 9.72 (s, 1 H), 8.20 (s, 1 H), 8.18-7.76 (m, 4 H), 7.41-7.34 (m, 3 H0, 7.20-7.13 (m, 1 H), 3.71-3.65 (m, 2 H), 3.68 (s, 3 H), 3.51-3.44 (m, 2 H), 2.98-2.87 (m, 4 H), 1.10 (t, 6 H); ESMS m/z 458.2 (M + H⁺). |

TABLE 8-continued

| Compound # | Structure | NMR and/or ESMS |
|---|---|---|
| 133 | 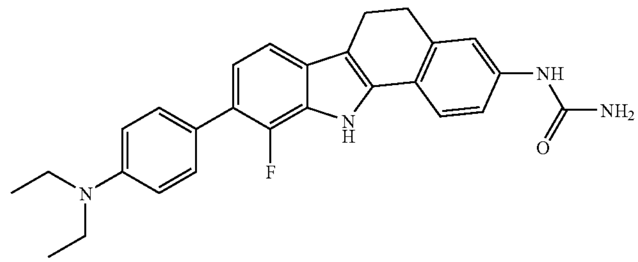 | ¹H NMR (400 MHz, DMSO-d6, HCl salt) δ 11.83 (br, 1 H), 8.71 (s, 1 H), 8.13 (s, 1 H), 7.86 (br, 1 H), 7.70 (d, 1 H), 7.36-7.32 (m, 4 H), 7.24-7.13 (m, 2 H), 5.98 (br, 2 H), 3.71-3.46 (m, 4 H), 2.90 (dd, 4 H), 1.10 (t, 6 H); ESMS m/z 443.2 (M + H⁺). |
| 134 | 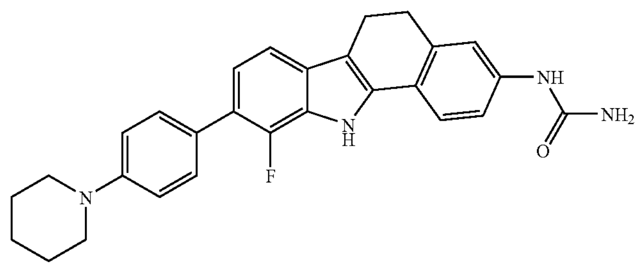 | ¹H NMR (400 MHz, DMSO-d6, HCl salt) δ 11.78 (s, 1 H), 8.67 (s, 1 H), 7.79-7.68 (m, 4 H), 7.36-7.32 (m, 4 H), 7.11-7.03 (m, 1 H), 5.95 (br, 2 H), 3.50 (br, 4 H), 2.95-2.88 (m, 4 H), 1.89 (br, 4 H), 1.66 (br, 2 H); ESMS m/z 455.2 (M + H⁺). |
| 135 | 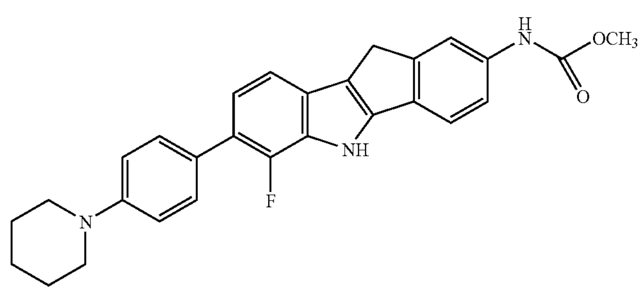 | ¹H NMR (400 MHz, Acetone-d6, TFA salt) δ 11.13 (s, 1 H), 8.73 (s, 1 H), 7.87 (s, 1 H), 7.69-7.67 (m, 2 H), 7.62-7.54 (m, 4 H), 7.45-7.43 (d, 1 H), 7.20-7.16 (m, 1 H), 4.74 (br, 2 H), 3.76 (s, 2 H), 3.73 (s, 3 H), 3.51 (br, 4 H), 1.93 (br, 4 H), 1.70 (br, 2 H); ESMS m/z 456.2 (M + H⁺). |
| 136 | 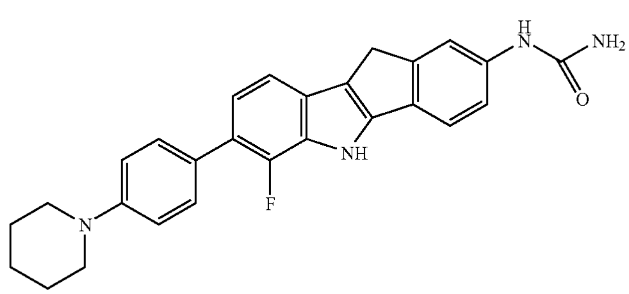 | ¹H NMR (400 MHz, DMSO-d6, HCl salt) δ 11.92 (br, 1 H), 8.60 (s, 1 H), 7.76 (s, 1 H), 7.56-7.46 (m, 3 H), 7.37-7.28 (m, 2 H), 7.18-7.15 (m, 1 H), 7.12-7.08 (m, 2 H), 5.86 (br, 2 H), 3.67 (s, 2 H), 3.29 (br, 4 H), 1.76 (br, 4 H), 1.60 (br, 2 H); ESMS m/z 441.2 (M + H⁺). |

Examples 137-141

By repeating the procedures described in examples 30, 92 and/or 107, using appropriate starting materials, the following compounds identified in Table 9, are obtained.

TABLE 9

| Compound # | Structure | NMR and/or ESMS |
|---|---|---|
| 137 | 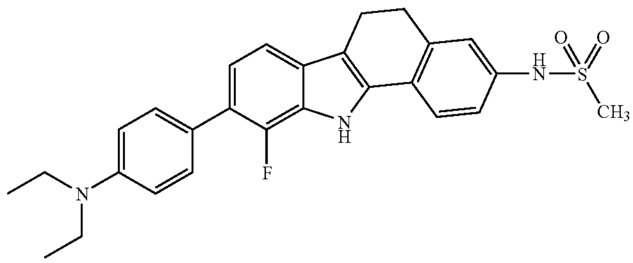 | $^1$H NMR (400 MHz, CD$_3$OD, HCl salt) δ 7.92 (d, 2 H), 7.71-7.65 (m, 3 H), 7.39 (d, 1 H), 7.22-7.11 (m, 3 H), 3.82-3.70 (m, 4 H), 3.12-2.91 (m, 7 H), 1.20 (t, 6 H); ESMS m/z 478.2 (M + H$^+$). |
| 138 | 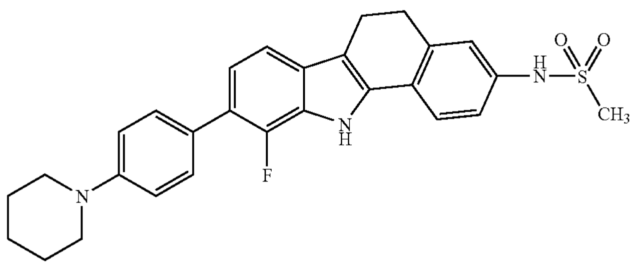 | $^1$H NMR (400 MHz, CD$_3$OD, TFA salt) δ 7.82 (d, 2 H), 7.75-7.65 (m, 3 H), 7.39 (d, 1 H), 7.22-7.15 (m, 2 H), 7.11 (dd, 1 H), 3.72-3.64 (m, 4 H), 3.11-2.90 (m, 7 H), 2.11-2.04 (m, 4 H), 1.89-1.81 (m, 2 H), ESMS m/z 490.2 (M + H$^+$). |
| 139 | 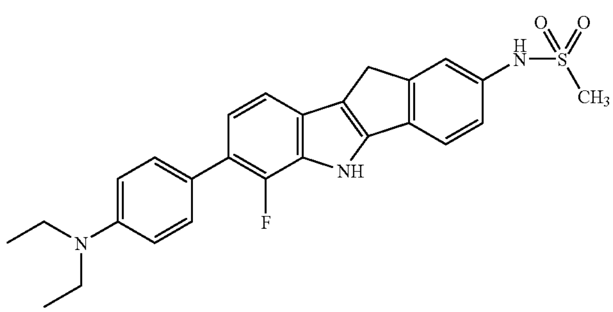 | $^1$H NMR (400 MHz, CD$_3$OD, HCl salt) δ 7.92 (d, 2 H), 7.68 (d, 2 H), 7.60 (d, 1 H), 7.51 (s, 1 H), 7.45 (d, 1 H), 7.24 (d, 1 H), 7.19 (dd, 1 H), 3.80-3.70 (m, 6 H), 2.99 (s, 3 H), 1.19 (t, 6 H); ESMS m/z 464.2 (M + H$^+$). |
| 140 | 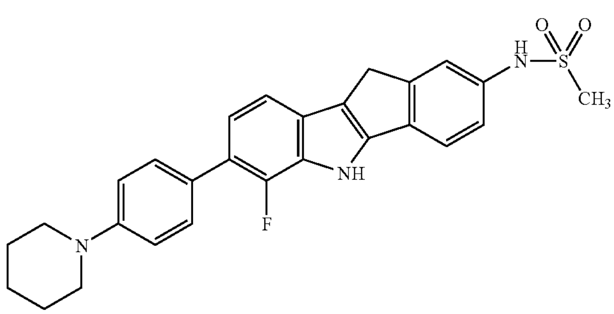 | $^1$H NMR (400 MHz, CD$_3$OD, TFA salt) δ 7.88 (d, 2 H), 7.71 (d, 2 H), 7.57 (d, 1 H), 7.49 (s, 1 H), 7.44 (d, 1 H), 7.23 (d, 1 H), 7.13 (dd, 1 H), 3.76 (s, 2 H), 3.72-3.62 (m, 4 H), 2.99 (s, 3 H), 2.10-2.01 (m, 4 H), 1.88-1.77 (m, 2 H); ESMS m/z 476.2 (M + H$^+$). |
| 141 | 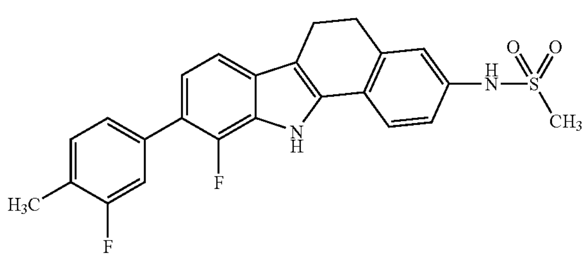 | $^1$H NMR (400 MHz, DMSO-d6) δ 11.83 (s, 1 H), 9.77 (s, 1 H), 7.80 (d, J = 8.1 Hz, 1 H), 7.51 (m, 1 H), 7.44 (m, 1 H), 7.36 (d, J = 8.2 Hz, 1 H), 7.24 (m, 1 H), 7.14 (m, 2 H), 7.07 (dd, J = 8.1, 7.0 Hz, 1 H), 30.03 (s, 3 H), 2.98 (m, 2 H), 2.91 (m, 2 H), 2.32 (m, 3 H); ESMS m/z 439.3 (M + H$^+$). |

Example 142

7-(4-Butyl-phenyl)-6-fluoro-10,10-dimethyl-5,10-dihydro-indeno[1,2-b]indole-2-carboxylic acid

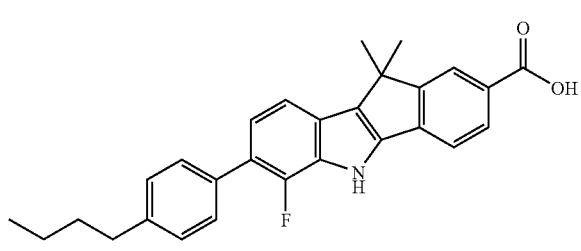

Example 84 (10 mg, 0.023 mmol) is dissolved in a mixture of methanol (2 mL) and HCl (5N, 2 mL). The solution is heated at 95° C. overnight. The mixture is diluted with water, and extracted with ethyl acetate (2×10 mL). The combined organic extracts are concentrated. The residue is treated with ethanol (1 mL) and water (0.3 mL) followed by LiOH (3 mg, 0.115 mmol). The mixture is then heated at 120° C. under microwave irradiation for 7 min. The mixture is filtered and purified by reverse phase HPLC to afford the title compound as a yellow solid. LC/MS calculated for [M+H]$^+$ $C_{28}H_{27}FNO_2$: 428.2, found: 428.2.

Example 143

6-Fluoro-10,10-dimethyl-7-(4-piperidin-1-yl-phenyl-5,10-dihydro-indeno[1,2-b]indole-2-carboxylic acid

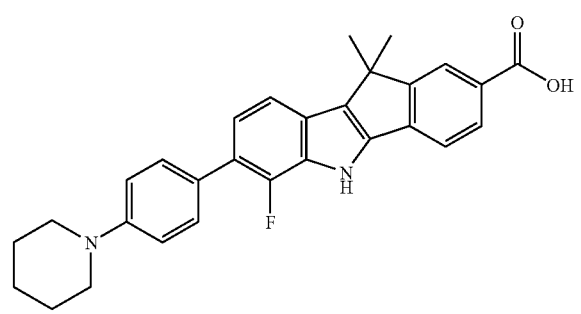

By repeating the procedures described in examples 82, 107 and 142, using appropriate starting materials, the title material is obtained as a tan solid: $^1$H NMR (400 MHz, CD3OD, HCl salt) δ 8.12 (s, 1H), 8.06 (d, 1H), 7.89 (d, 2H), 7.74 (d, 2H), 7.65 (d, 1H), 7.56 (d, 1H), 7.19 (dd, 1H), 3.80-3.70 (m, 4H), 2.12-2.06 (m, 4H), 1.92-1.78 (m, 2H), 1.66 (s, 6H); ESMS m/z 455.2 (M+H$^+$).

Example 144

N-[10-Fluoro-5,5-dimethyl-9-(4-piperidin-1-yl-phenyl)-5,11-dihydro-6H-benzo[a]carbazol-3-yl]-methanesulfonamide

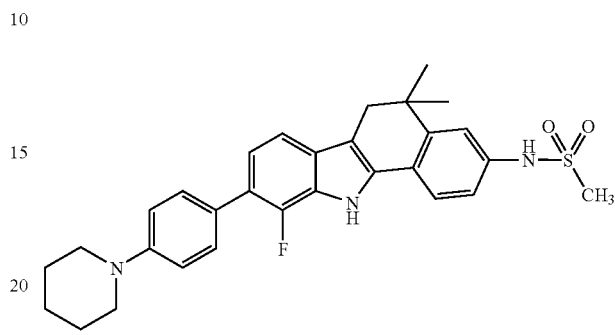

By repeating the procedures described in examples 82 (steps 1 and 2) and 92, using appropriate starting materials, the title material is obtained as a tan solid: $^1$H NMR (400 MHz, DMSO-d6, HCl salt) δ 11.85 (s, 1H), 9.79 (s, 1H), 7.84 (d, 2H), 7.68 (bs, 2H), 7.36 (d, 2H), 7.29 (d, 2H), 7.15 (m, 1H), 7.10 (m, 1H), 3.56 (s, 2H), 3.51-3.45 (bs, 4H), 3.03 (s, 3H), 2.84 (s, 2H), 1.93-1.82 (bs, 4H), 1.72-1.85 (bs, 2H), 1.29 (s, 6H); ESMS m/z 518.1 (M+H$^+$).

Example 145

N-(7-Benzooxazol-2-yl-5,10-dihydro-indeno[1,2-b]indol-2-yl)-acetamide

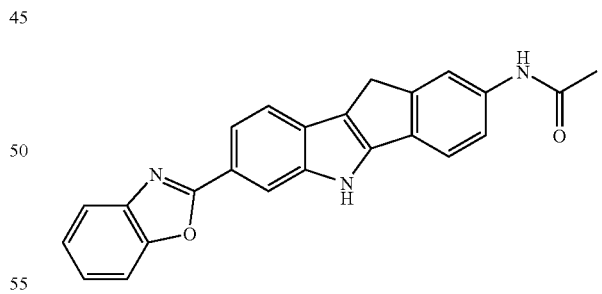

By repeating the procedures described in example 1 (steps 2 and 3), using appropriate starting materials (3-benzooxazol-2-yl-phenylamine is prepared as described in WO 03/074516), the title material is obtained as a solid: $^1$H NMR (400 MHz, DMSO-d6) δ 12.01 (s, 1H), 10.06 (s, 1H), 8.27 (s, 1H), 7.92 (m, 2H), 7.90 (m, 1H), 7.77 (m, 2H), 7.71 (d, J=8.4 Hz, 1H), 7.59 (s, 2H), 7.39 (m, 2H), 3.76 (s, 2H), 2.09 (s, 3H); ESMS m/z 380.2 (M+H$^+$).

Example 146

[9-(4-Butyl-phenyl)-10-fluoro-5,11-dihydro-6H-benzo[a]carbazol-3-yl]-urea

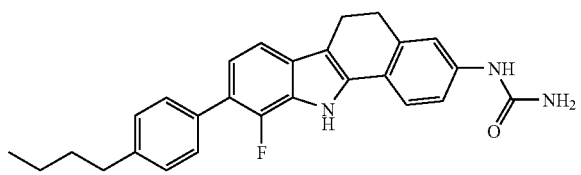

By repeating the procedures described in example 98, using appropriate starting materials, the title material is obtained as a tan solid: $^1$H NMR (400 MHz, Acetone-d6) δ 10.84 (bs, 1H), 8.16 (bs, 1H), 7.68 (d, 1H), 7.53 (d, 2H), 7.48 (d, 1H), 7.45 (s, 1H), 7.33 (d, 1H), 7.29 (d, 2H), 7.11 (dd, 1H), 5.50 (bs, 2H), 3.08-2.90 (m, 4H), 2.69 (t, 2H), 1.69-1.60 (m, 2H), 1.45-1.33 (m, 2H), 0.98 (t, 3H); ESMS m/z 428.2 (M+H$^+$).

Example 147

3-Amino-7-(4-butyl-phenyl)-6-fluoro-5,10-dihydro-indeno[1,2-b]indole-2-carboxylic acid

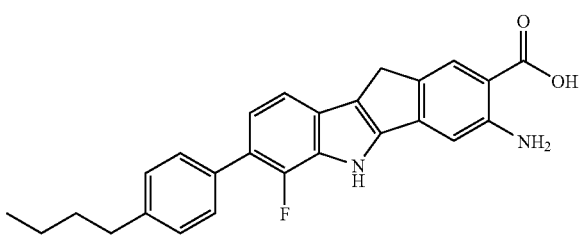

By purifying the product of example 100, step 4 using reverse phase HPLC, the title material is obtained as a tan solid: $^1$H NMR (400 MHz, Acetone-d6) δ 11.18 (s, 1H), 8.00 (s, 1H), 7.55 (dd, 2H), 7.50 (d, 1H), 7.32 (d, 2H), 7.22-7.18 (m, 1H), 7.10 (s, 1H), 3.71 (s, 2H), 2.69 (t, 2H), 1.71-1.63 (m, 2H), 1.44-1.34 (m, 2H), 0.95 (t, 3H); ESMS m/z 415.2 (M+H$^+$).

Example 148

7-(4-Butyl-phenyl)-6-fluoro-2-tetrazol-1-yl-5,10-dihydro-indeno[1,2-b]indole

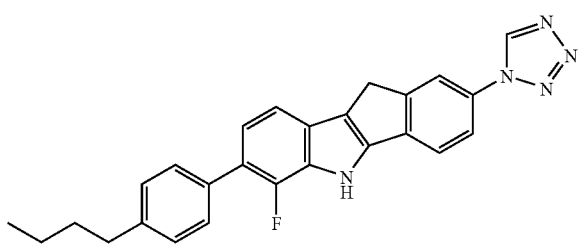

7-(4-Butyl-phenyl)-6-fluoro-5,10-dihydro-indeno[1,2-b]indol-2-ylamine (example 98, step 1, 60 mg, 0.1620 mmol) is dissolved in AcOH (1.6 mL). Triethyl orthoformate (38 mg, 0.2591 mmol, 1.6 eq.) and sodium azide (15 mg, 0.2429 mmol, 1.5 eq.) are added to the starting material solution sequentially at room temperature. The resulting reaction mixture is heated to 80° C. for 3.5 h. After cooling to room temperature, the reaction is diluted with EtOAc and sequentially washed with H$_2$O, 1 N HCl (aq), and saturated aqueous NaCl. The organic solution is dried over Na$_2$SO$_4$ and concentrated. The resulting residue is purified by reverse phase HPLC to afford the title compound as a tan solid: $^1$H NMR (400 MHz, Acetone-d6) δ 11.31 (bs, 1H), 9.77 (s, 1H), 8.15 (s, 1H), 7.97 (s, 2H), 7.62-7.52 (m, 3H), 7.38 (d, 2H), 7.21 (dd, 1H), 3.99 (s, 2H), 2.69 (t, 2H), 1.72-1.63 (m, 2H), 1.50-1.40 (m, 2H), 0.99 (t, 3H); ESMS m/z 424.1 (M+H$^+$).

Example 149

3-[9-(4-Butyl-phenyl)-10-fluoro-5,11-dihydro-6H-benzo[a]carbazol-3-yl]-4H-[1,2,4]oxadiazol-5-one

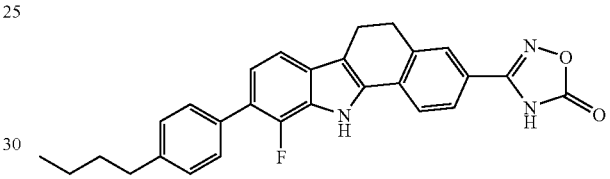

Step 1: 9-(4-Butyl-phenyl)-10-fluoro-5,11-dihydro-6H-benzo[a]carbazole-3-carbonitrile (obtained by repeating the procedures described in example 78, using appropriate starting materials, 76 mg, 0.1927 mmol, 1 eq.), hydroxylamine HCl salt (27 mg, 0.3853 mmol, 2 eq.) and Na$_2$CO$_3$ (61 mg, 0.5780 mmol, 3 eq.) are added to EtOH (3.5 mL), H$_2$O (1.0 mL) and 1 N NaOH (0.35 mL). N$_2$ gas is bubbled through the reaction mixture for 5 min. The reaction is heated in a sealed tube at 80° C. overnight. The reaction is concentrated to dryness and taken forward crude to the next step without purification: ESMS m/z 428.1 (M+H$^+$).

Step 2: The crude product from step 1 and pyridine (12 mg, 0.15 mmol) are dissolved in anhyd. THF (2 mL) and cooled to 0° C. 2-ethylhexyl chloroformate (0.03 mL, 0.15 mmol) is added dropwise. The resulting reaction mixture is stirred at 0° C. for 45 min. The reaction is diluted with EtOAc and sequentially washed with H$_2$O and saturated aqueous NaCl. The organic solution is dried over Na$_2$SO$_4$ and concentrated. The resulting residue is purified on silica gel (2:1 hexanes/EtOAc) to afford the acylation product as an off-white solid.

Steps 3: The product from step 2 (23 mg, 0.04 mmol) is dissolved in anhydrous toluene (2 mL). N$_2$ gas is bubbled through the reaction mixture for 5 min. The reaction is heated in a sealed tube at 125° C. overnight. The reaction mixture is concentrated to dryness and purified by reverse phase HPLC to afford the title compound as a light yellow solid: ESMS m/z 454.2 (M+H$^+$).

Assays

Compounds of the present invention are assayed to measure their potency as mimetics of TPO in an in vitro proliferation assay using the murine BaF3 cell line transfected with human TPO receptor (TPO-R):

Luciferase Reporter Assays

Ba/F3-TpoR cells are washed and resuspended in RPMI-1640 supplemented with 1% or 20% of FBS, MS, HS or (human serum albumin+alpha1 acid glycoprotein), 1% Pen-Strep-Glu and 1 mM or 25 μM $ZnSO_4$ at 8×104 cells/mL and dispensed to 384-well plates at 50 mL/well for overnight starvation (18-20 hr). The $2^{nd}$ day, the starved cells are treated with 0.5 mL of DMSO, compound or rhTpo (30 ng/mL) at 37° C., 5% $CO_2$ for 7 hours. Perkin Elmer Britelite (25 mL) diluted to 60% in water is added to each well and a few minutes later, the plates are read on a CLIPR to record the luminescence signal.

Proliferation Assay

Ba/F3-TPO-R cells are washed and resuspended in RPMI-1640 supplemented with 1% FBS, 1% Pen-Strep-Glu and 1 mM or 25 μM $ZnSO_4$ at 8×104 cells/mL and dispensed to 384-well plates at 50 mL/well for overnight starvation (18-20 hours). The $2^{nd}$ day, the starved cells are treated with 0.5 mL of DMSO, compound or rhTpo (30 ng/mL) at 37° C., 5% $CO_2$ for 48 hours. Alamar Blue reagent (3.5 μL at ~7% final concentration) is added to each well, the plates are incubated for 4 hours and read on an Analyst GT to record the fluorescence signal.

CFU-Meg Assay

CD34+ cells and MegaCult-C kit (StemCell Technologies, Inc., Vancouver, Canada) are used for the assay. CD34+ cells are mixed with the MegaCult-C collagen solution according to the manufacturer's protocol at 104 cells per slide. After addition of TPO or a compound of the invention at different concentrations, the slides are incubated at 37° C., 5% $CO_2$ for 12 days, fixed, stained for human CFU-Meg and colonies are quantitated using an inverted microscope.

Compounds of Formula I, in free form or in pharmaceutically acceptable salt form, exhibit valuable pharmacological properties, for example, as indicated by the in vitro tests described in this application. The compounds of the invention preferably exhibit TPO mimetic activity with an IC50 in the range of $1×10^{-9}$ to $1×10^{-5}$M, preferably less than 500 nM, more preferably less than 250 nM. Compounds of Formula I exhibit efficacy in the range of 25% to 150% relative to TPO.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A compound of Formula I:

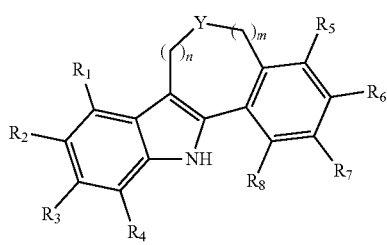

I in which:
n is selected from 0, 1, 2 and 3;
m is selected from 0 and 1;

Y is selected from $CR_9R_{10}$, $NR_9$, O and $S(O)_2$; wherein $R_9$ and $R_{10}$ are independently selected from hydrogen and $C_{1-6}$alkyl;

$R_1$ is selected from hydrogen, halo, cyano, nitro, $NR_9R_{10}$, $C_{1-6}$alkyl, $C_{1-6}$alkoxy, halo-substituted-$C_{1-6}$alkoxy, halo-substituted-$C_{1-6}$alkyl, $C_{3-12}$cycloalkyl and $C_{3-8}$heterocycloalkyl; wherein $R_9$ and $R_{10}$ are independently selected from hydrogen and $C_{1-6}$alkyl;

$R_2$ and $R_3$ are independently selected from halo, cyano, $C_{1-6}$alkyl, $C_{2-6}$alkenyl, $C_{2-6}$alkynyl, halo-substituted-$C_{1-6}$alkyl, $C_{6-10}$aryl, $C_{1-10}$heteroaryl, $C_{3-8}$heterocycloalkyl and $C_{3-12}$cycloalkyl; wherein any alkyl, alkenyl, alkynyl, aryl, heteroaryl, cycloalkyl or heterocycloalkyl of $R_2$ or $R_3$ is optionally substituted by 1 to 3 radicals independently selected from halo, $C_{1-6}$alkyl, $C_{1-6}$alkoxy, cyano-$C_{1-6}$alkyl, hydroxy-$C_{1-6}$alkyl, halo-substituted-$C_{1-6}$alkyl, halo-substituted-$C_{1-6}$alkoxy, $-NR_{12}R_{13}$, $-XOR_{13}$, $-S(O)_2R_{13}$, $C_{3-12}$cycloalkyl, $C_{3-8}$heterocycloalkyl, $C_{6-10}$aryl and $C_{1-10}$heteroaryl; wherein X is a bond or $C_{1-6}$alkylene and $R_{12}$ and $R_{13}$ are independently selected from $C_{1-6}$alkyl, cyano-$C_{1-6}$alkyl, hydroxy-$C_{1-6}$alkyl, halo-substituted-$C_{1-6}$alkyl and halo-substituted-$C_{1-6}$alkoxy; wherein any aryl, heteroaryl, cycloalkyl and heterocycloalkyl substituents of $R_2$ and $R_3$ are optionally further substituted with 1 to 3 radicals independently selected from halo, $C_{1-6}$alkyl, $C_{1-6}$alkoxy, cyano-$C_{1-6}$alkyl, hydroxy-$C_{1-6}$alkyl, halo-substituted-$C_{1-6}$alkyl and halo-substituted-$C_{1-6}$alkoxy;

$R_4$ is selected from hydrogen, halo, cyano, nitro, $XNR_9R_{10}$, $OXNR_9R_{10}$, $C_{1-6}$alkyl, $C_{1-6}$alkoxy, halo-substituted-$C_{1-6}$alkoxy, halo-substituted-$C_{1-6}$alkyl, $C_{3-12}$cycloalkyl, $C_{3-8}$heterocycloalkyl, $C_{6-10}$aryl and $C_{1-10}$heteroaryl; wherein X is a bond or $C_{1-6}$alkylene and $R_9$ and $R_{10}$ are independently selected from hydrogen and $C_{1-6}$alkyl;

$R_5$ is hydrogen, $C_{3-8}$heterocycloalkyl, $C_{6-10}$aryl, $OS(O)_2R_{11}$, $NR_{11}S(O)_2R_{14}$, $NR_{11}C(O)R_{14}$, $NR_{11}C(O)NR_{11}R_{14}$, $NR_{11}C(O)C(O)OR_{14}$, $NR_{11}C(O)OR_{14}$, $OC(O)NR_{11}R_{14}$, $C(O)R_{15}$, and $NR_{11}R_{14}$, $NR_{11}R_{15}$; wherein $R_{11}$ and $R_{14}$ are independently selected from hydrogen, $C_{1-6}$alkyl, halo-substituted-$C_{1-6}$alkyl, $C_{1-6}$alkoxy, cyano-$C_{1-6}$alkyl, hydroxy-$C_{1-6}$alkyl and $C_{1-6}$alkyl substituted with $NR_9R_{10}$; $R_{15}$ is $C_{3-8}$heterocycloalkyl optionally substituted with 1 to 3 $C_{1-6}$alkyl radicals; wherein any aryl, or heterocycloalkyl of $R_5$ can be optionally further substituted with 1 to 3 radicals independently selected from halo, $C_{1-6}$alkyl, $C_{1-6}$alkoxy, cyano-$C_{1-6}$alkyl, hydroxy-$C_{1-6}$alkyl, halo-substituted-$C_{1-6}$alkyl, halo-substituted-$C_{1-6}$alkoxy, $OS(O)_2R_{11}$, $NR_{11}S(O)_2R_{14}$, $NR_{11}C(O)R_{14}$, $NR_{11}C(O)NR_{11}R_{14}$, $NR_{11}C(O)C(O)OR_{14}$, $NR_{11}C(O)OR_{14}$, $OC(O)NR_{11}R_{14}$, $C(O)OR_{11}$ $C(O)R_{15}$, $NR_{11}R_{14}$, $NR_{11}R_{15}$ and $C(O)NR_{11}R_{14}$; wherein $R_{11}$, $R_{14}$ and $R_{15}$ are as defined above;

$R_6$ and $R_7$ are independently selected from hydrogen, hydroxyl, $C_{3-8}$heterocycloalkyl, $C_{1-10}$heteroaryl, $C_{6-10}$aryl, $OS(O)_2R_{11}$, $NR_{11}S(O)_2R_{14}$, $NR_{11}C(O)R_{14}$, $NR_{11}C(O)NR_{11}R_{14}$, $NR_{11}C(O)C(O)OR_{14}$, $NR_{11}C(O)OR_{14}$, $OC(O)NR_{11}R_{14}$, $C(O)OR_{11}$, $C(O)R_{15}$, $NR_{11}R_{14}$, $NR_{11}R_{15}$ and $C(O)NR_{11}R_{14}$; wherein $R_{11}$ and $R_{14}$ are independently selected from hydrogen, $C_{1-6}$alkyl, halo-substituted-$C_{1-6}$alkyl, $C_{1-6}$alkoxy, cyano-$C_{1-6}$alkyl, hydroxy-$C_{1-6}$alkyl and $C_{1-6}$alkyl substituted with $NR_9R_{10}$; $R_{15}$ is $C_{3-8}$heterocycloalkyl optionally substituted with 1 to 3 $C_{1-6}$alkyl radicals; wherein any aryl, heterocycloalkyl or heteroaryl of $R_6$ and $R_7$ can be optionally further substituted with 1 to 3 radicals independently selected from halo, $C_{1-6}$alkyl, $C_{1-6}$alkoxy, cyano-$C_{1-6}$alkyl, hydroxy-$C_{1-6}$alkyl, halo-substituted-$C_{1-6}$alkyl, halo-substituted-$C_{1-6}$alkoxy, $OS(O)_2R_{11}$, $NR_{11}S(O)_2R_{14}$, $NR_{11}C(O)R_{14}$, $NR_{11}C(O)NR_{11}R_{14}$, $NR_{11}C(O)C(O)OR_{14}$, $NR_{11}C(O)OR_{14}$, $OC(O)NR_{11}R_{14}$, $C(O)OR_{11}$, $C(O)R_{15}$, $NR_{11}R_{14}$, $NR_{11}R_{15}$ and $C(O)NR_{11}R_{14}$; wherein $R_{11}$, $R_{14}$ and $R_{15}$ are as defined above;

$R_8$ is selected from hydrogen, halo, cyano, $C_{1-6}$alkoxy, halo-substituted-$C_{1-6}$alkyl, halo-substituted-$C_{1-6}$alkoxy and $C_{1-6}$alkyl; and the pharmaceutically acceptable salts, hydrates, solvates and isomers thereof.

2. The compound of claim 1 in which:

n is selected from 0, 1 and 2;

Y is selected from $CR_9R_{10}$, O and $S(O)_2$; wherein $R_9$ and $R_{10}$ are independently selected from hydrogen and $C_{1-6}$alkyl;

$R_1$ is selected from hydrogen, $C_{1-6}$alkyl and halo-substituted-$C_{1-6}$alkyl;

$R_2$ is selected from halo, $C_{6-10}$aryl, $C_{1-6}$alkyl and $C_{2-6}$alkenyl; wherein any aryl of $R_2$ is optionally substituted by 1 to 3 radicals independently selected from halo, $C_{1-6}$alkyl and $C_{1-6}$alkoxy;

$R_3$ is selected from halo, hydroxy, cyano, $C_{1-6}$alkyl, $C_{2-6}$alkenyl, halo-substituted-$C_{1-6}$alkyl, $C_{6-10}$aryl and $C_{1-10}$heteroaryl; wherein any aryl or heteroaryl of $R_3$ is optionally substituted by 1 to 3 radicals independently selected from halo, $C_{1-6}$alkyl, $C_{1-6}$alkoxy, cyano-$C_{1-6}$alkyl, halo-substituted-$C_{1-6}$alkyl, halo-substituted-$C_{1-6}$alkoxy, —$NR_{12}R_{13}$, —$XOR_{13}$, —$S(O)_2R_{13}$ and $C_{3-8}$heterocycloalkyl; wherein X is a bond or $C_{1-6}$alkylene and $R_{12}$ and $R_{13}$ are independently selected from hydrogen and $C_{1-6}$alkyl;

$R_4$ is selected from hydrogen and halo;

$R_5$ is hydrogen;

$R_6$ is selected from $C_{1-10}$heteroaryl, $OS(O)_2R_{11}$, $NR_{11}S(O)_2R_{14}$, $NR_{11}C(O)R_{14}$, $NR_{11}C(O)OR_{14}$, $C(O)OR_{11}R_{15}$, $NR_{11}R_{14}$ and $C(O)NR_{11}R_{14}$; wherein $R_{11}$ and $R_{14}$ are independently selected from hydrogen, $C_{1-6}$alkyl, hydroxy-$C_{1-6}$alkyl and halo-substituted-$C_{1-6}$alkyl; $R_{15}$ is $C_{3-8}$heterocycloalkyl optionally substituted with 1 to 3 $C_{1-6}$alkyl radicals;

$R_7$ is selected from hydrogen, hydroxyl, $NR_{11}S(O)_2R_{14}$ and $NR_{11}R_{14}$; wherein $R_{11}$ and $R_{14}$ are as defined above;

$R_8$ is selected from hydrogen and $C_{1-6}$alkyl.

3. The compound of claim 2 in which: n is selected from 0 and 1; and Y is selected from $CR_9R_{10}$, O and $S(O)_2$; wherein $R_9$ and $R_{10}$ are independently selected from hydrogen and methyl.

4. The compound of claim 3 in which: $R_1$ is selected from hydrogen and trifluoromethyl; and $R_2$ is selected from hydrogen, bromo, chloro, iodo, allyl, trifluoromethyl, and phenyl optionally substituted with 1 to 3 radicals independently selected from methyl and ethyl.

5. The compound of claim 4 in which $R_3$ is selected from hydrogen, bromo, chloro, cyano, trifluoromethyl, allyl, pyrimidinyl, pyridinyl, piperidinyl, benzoxazolyl, thiazolyl and phenyl; wherein said pyrimidinyl, thiazolyl and phenyl are optionally substituted by 1 to 3 radicals independently selected from chloro, fluoro, methyl, ethyl, propyl, butyl, iso-butyl, t-butyl, isopropoxy, propoxy, methoxy, dimethylamino, methoxy-methyl, hydroxy, cyclohexyl, pyridinyl, methylsulfonyl, ethylsulfonyl, morpholino, diethylamino, pyrazinyl, piperidinyl, phenyl, trifluoromethyl, hexanyl and cyano-methyl.

6. The compound of claim 5 in which $R_4$ is selected from hydrogen, fluoro and bromo; and $R_5$ and $R_8$ are both hydrogen.

7. The compound of claim 6 in which $R_6$ is selected from amino, ureido, hydroxy-acetyl-amino, carboxyl, methoxy-carbonyl, methoxycarbonyl-amino, 4H-[1,2,4]oxadiazol-5-one, tetrazolyl, methyl-aminocarbonyl, dimethyl-aminocarbonyl, methyl-carbonyl-amino, morpholino-carbonyl, methyl-piperazinyl-carbonyl, cyano, tetrazolyl, amino-carbonyl, methyl-sulfonyl-amino, methyl-sulfonyl-amino-carbonyl, t-butoxy-carbonyl-amino, carbonyl-amino, hydroxy-carbonyl-methyl-amino, hydroxy-methyl-carbonyl-amino, oxalyl-amino and trifluoromethyl-sulfonyloxy; and $R_7$ is selected from hydrogen, hydroxyl, methyl-carbonyl-amino, amino and amino-carbonyl.

8. A pharmaceutical composition comprising a therapeutically effective amount of a compound of claim 1 in combination with a pharmaceutically acceptable excipient.

9. A method for treating thrombocytopenia in an animal, which method comprises administering to the animal a therapeutically effective amount of a compound of claim 1.

10. A compound selected from:

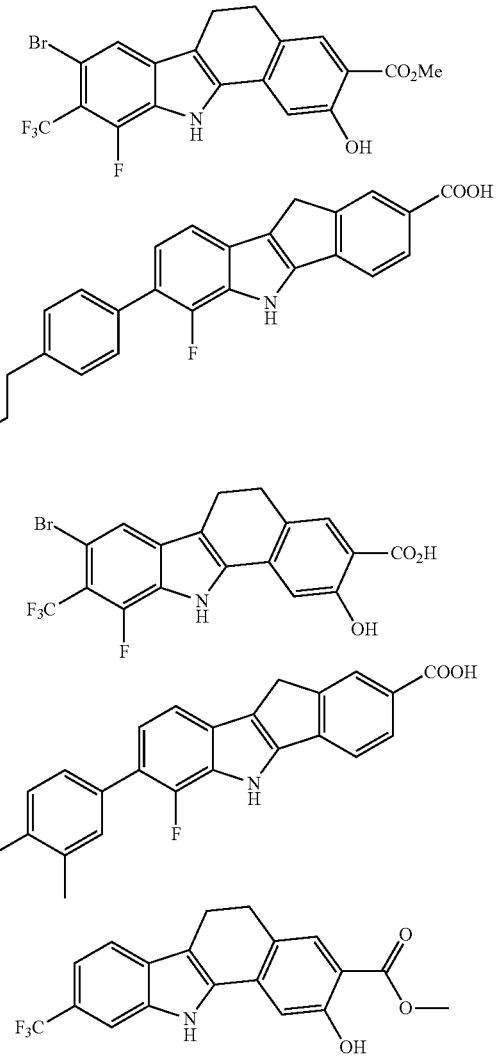

85
-continued
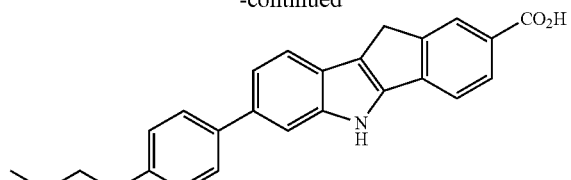
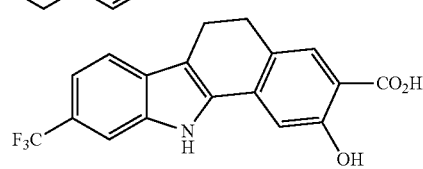
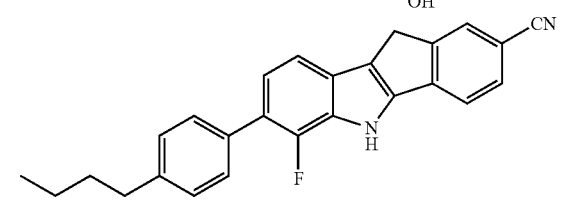
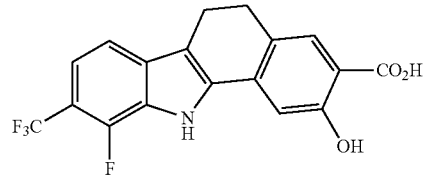
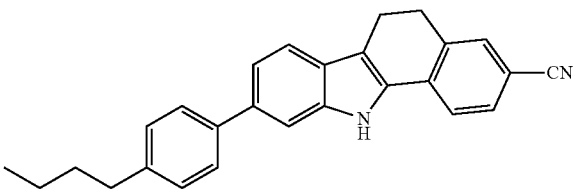
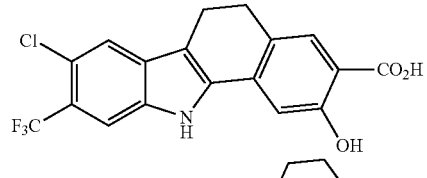
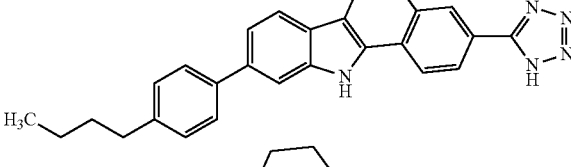
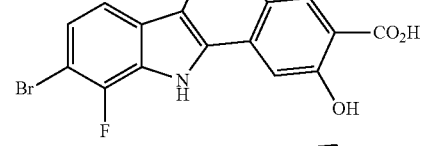
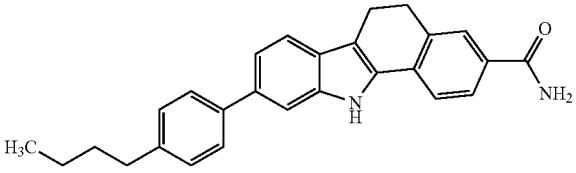
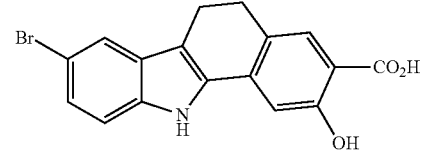
86
-continued
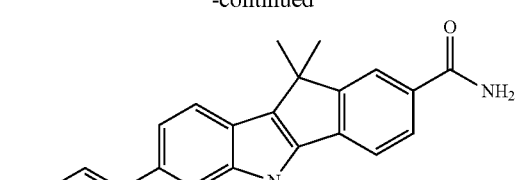
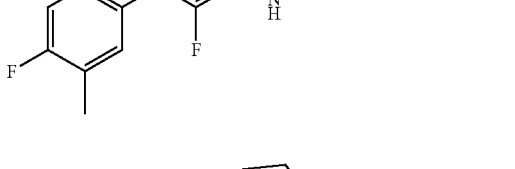
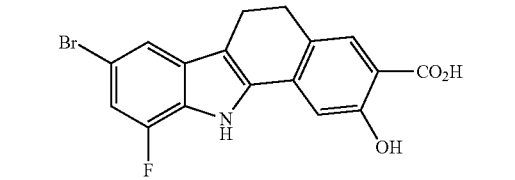
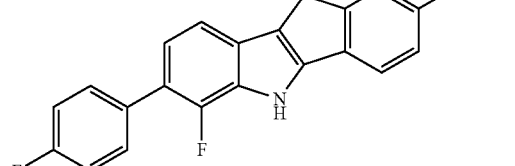
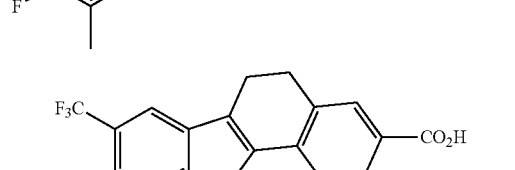
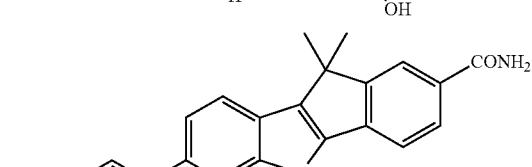
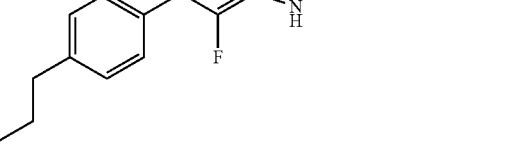
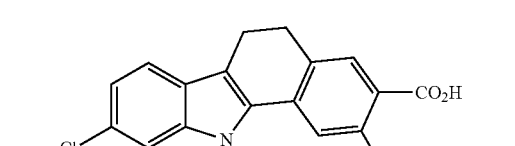
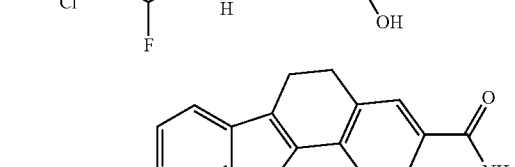
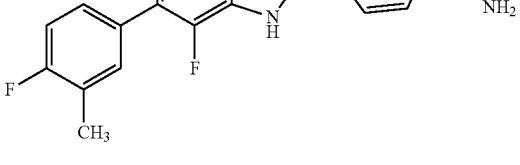

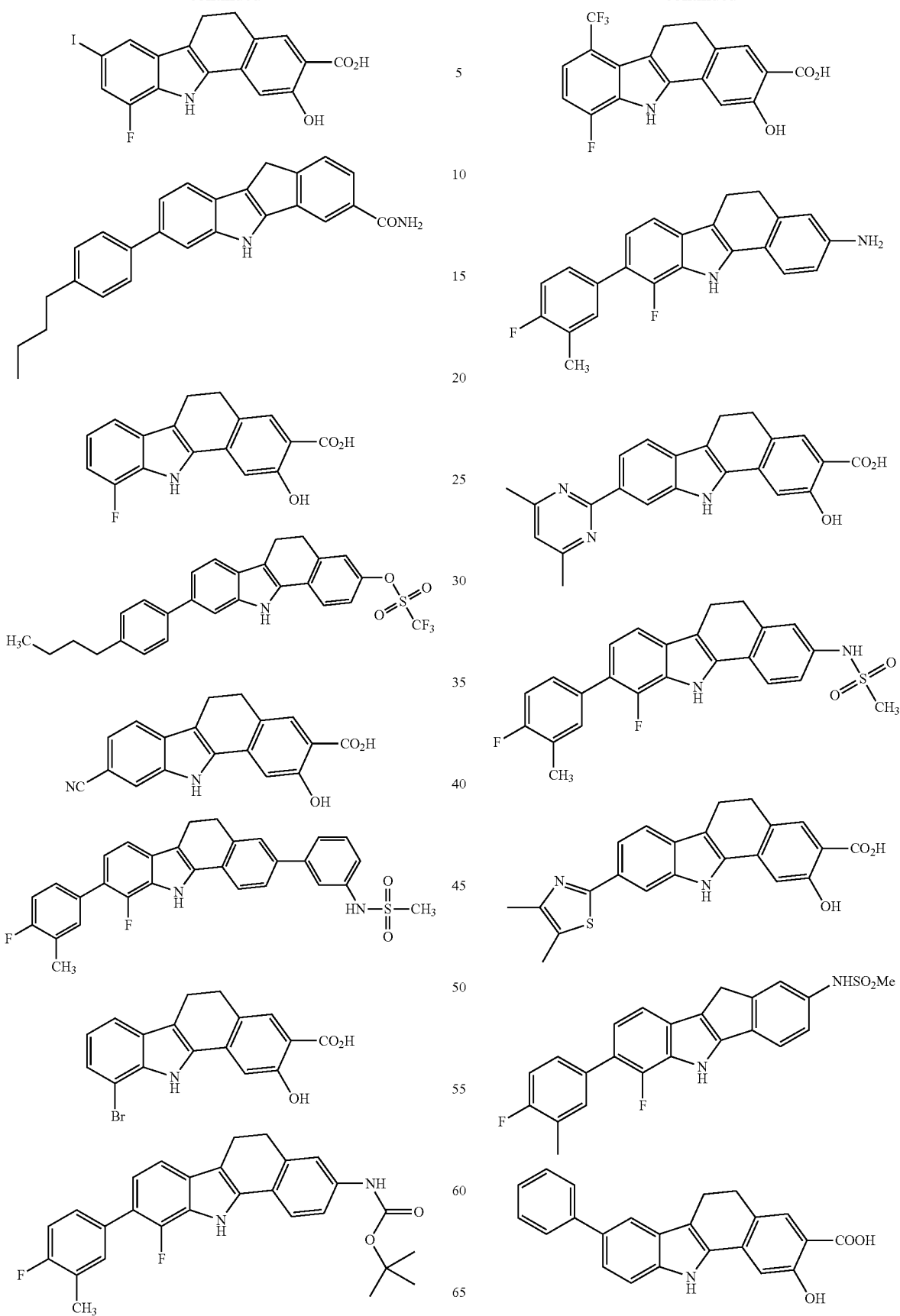

89
-continued
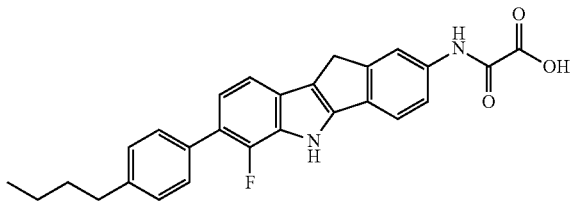
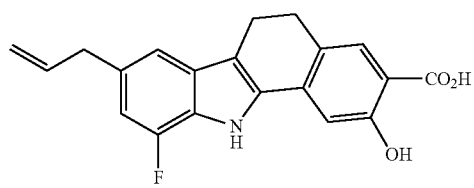
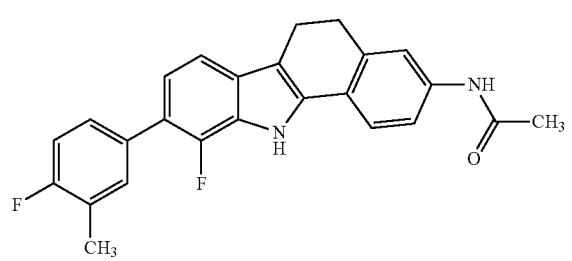
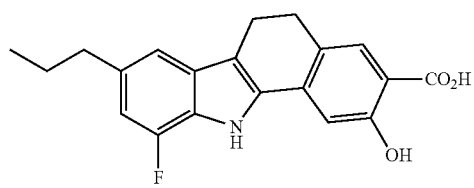
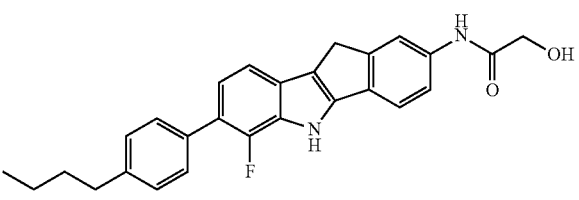
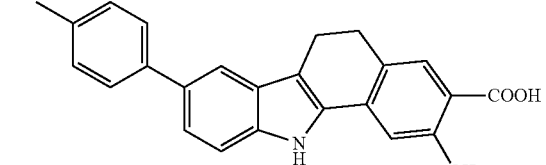
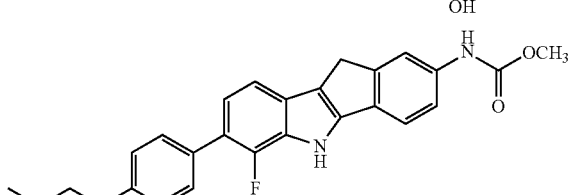
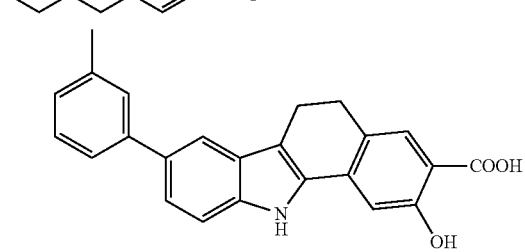
90
-continued
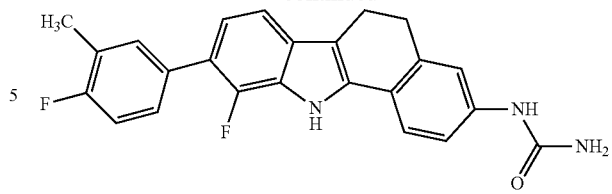
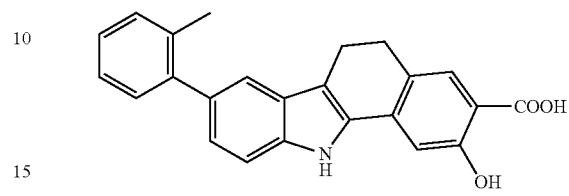
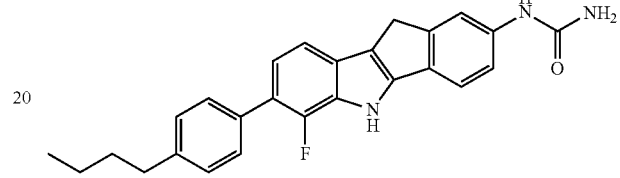
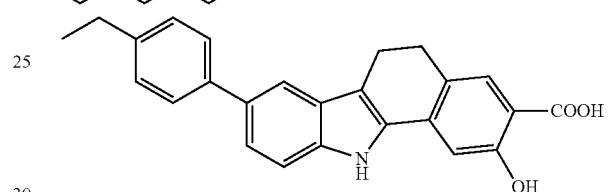
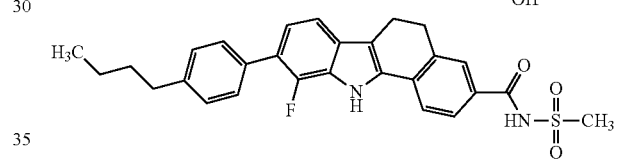
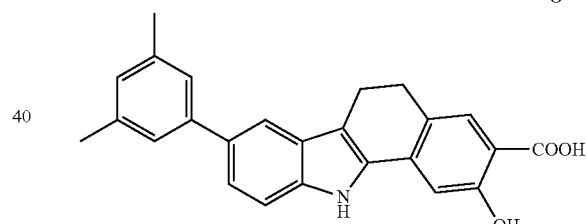
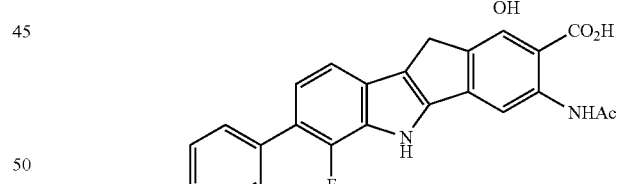
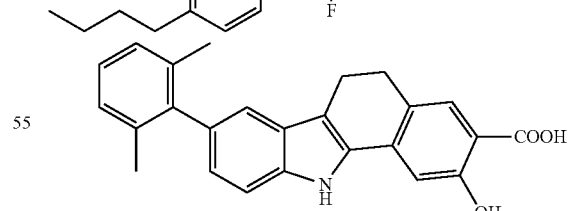
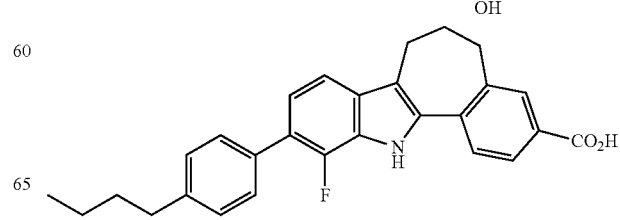

91
-continued
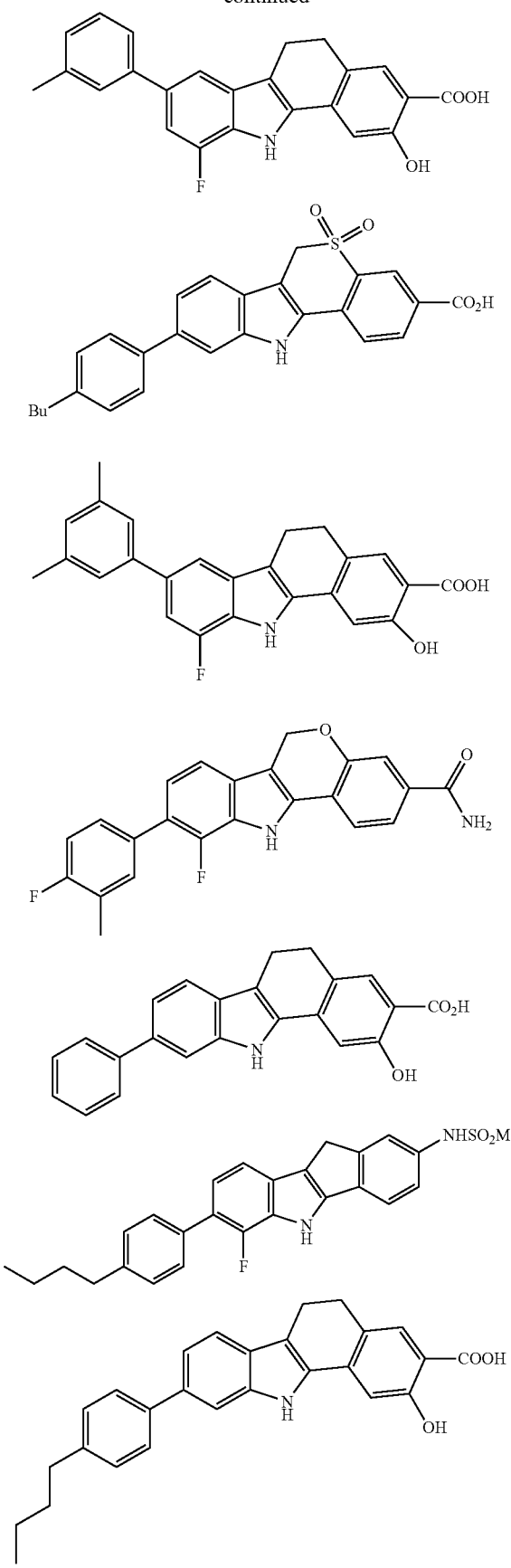
92
-continued
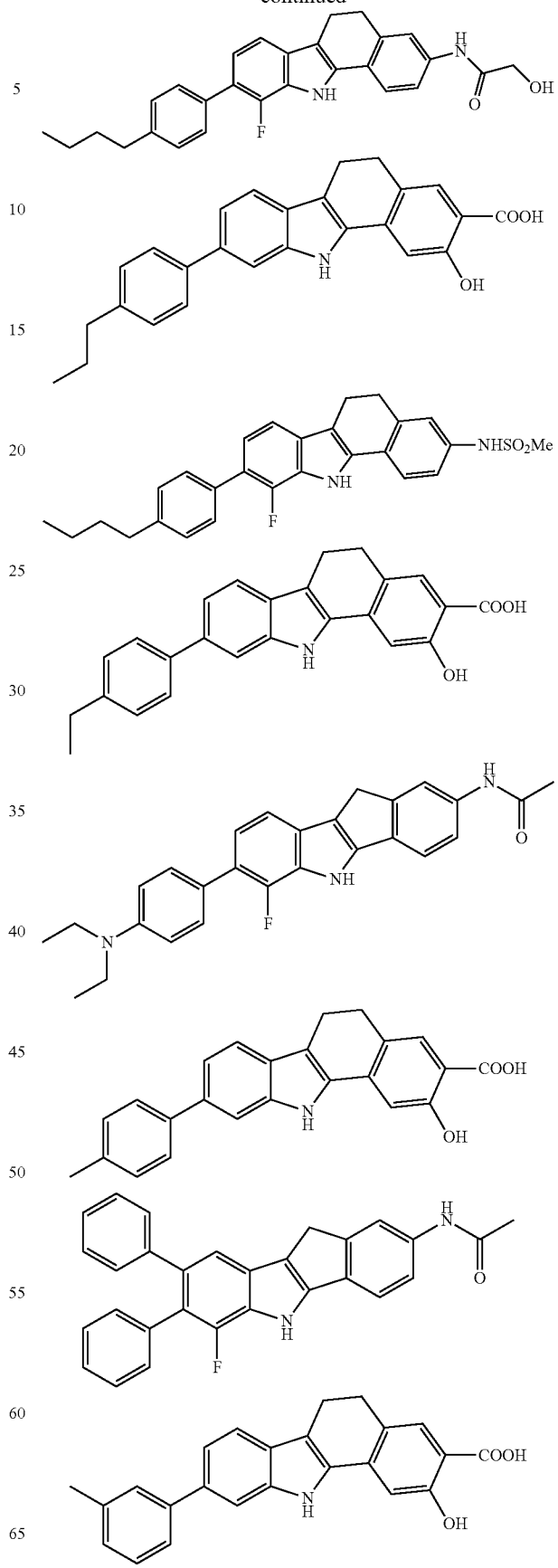

93
-continued
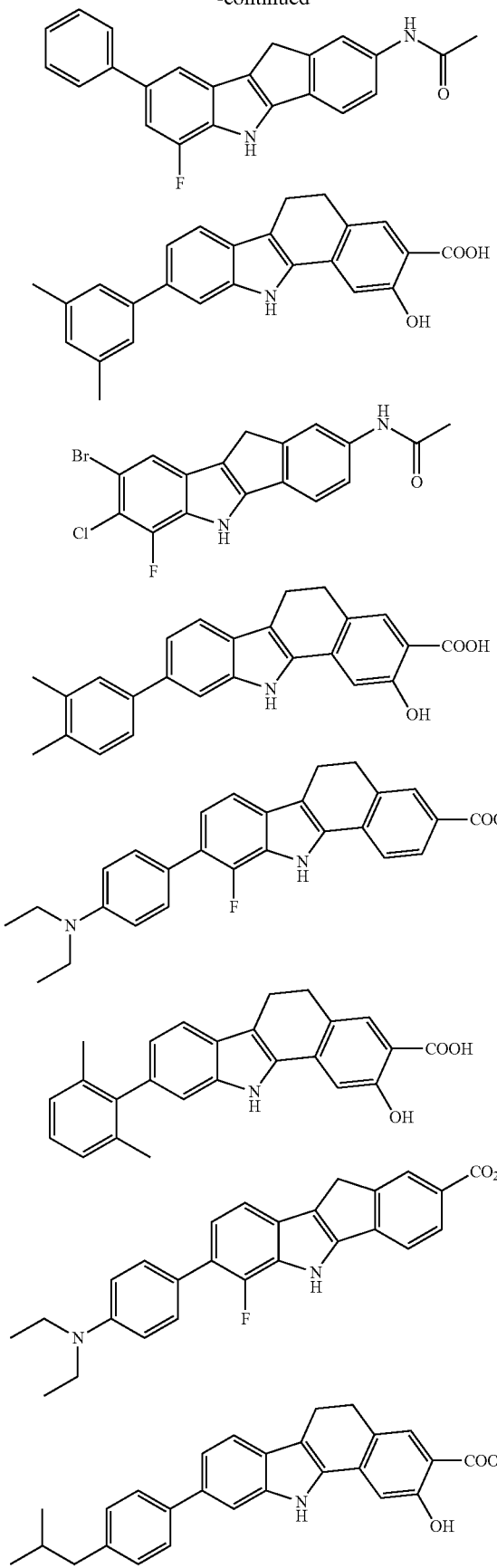
94
-continued
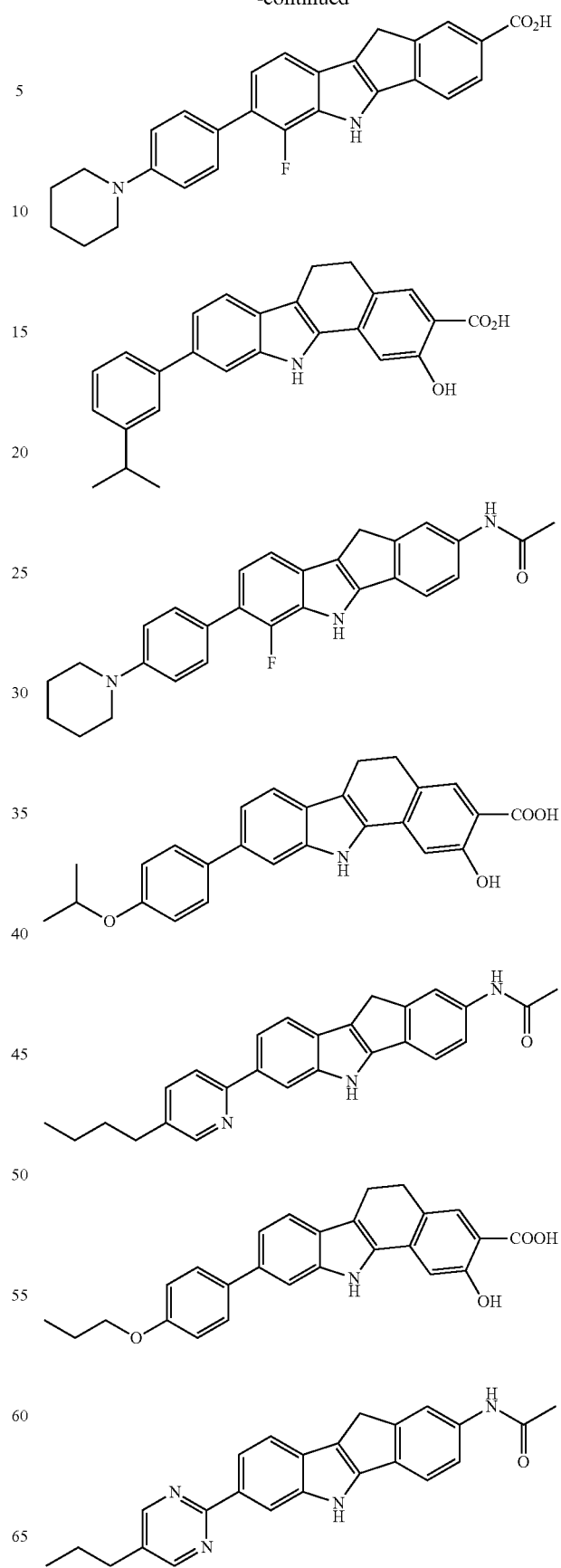

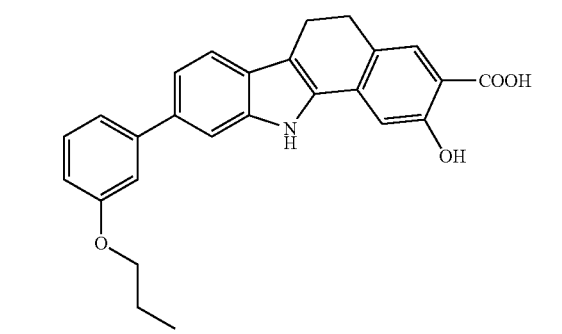
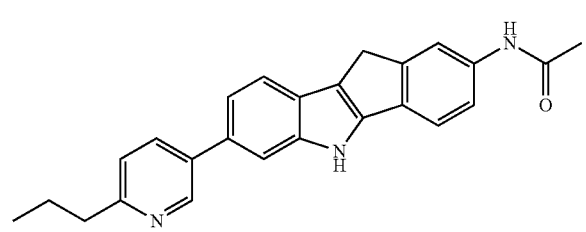
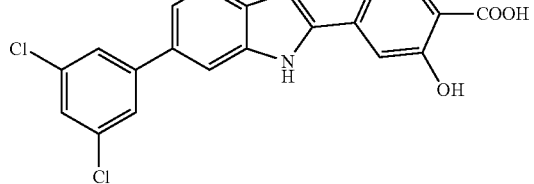
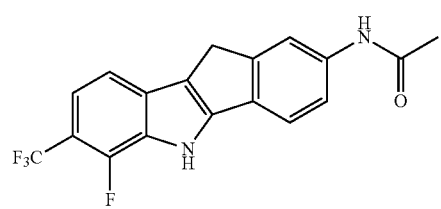
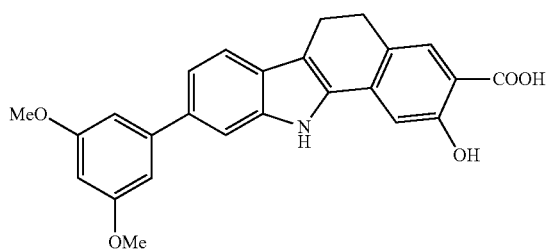
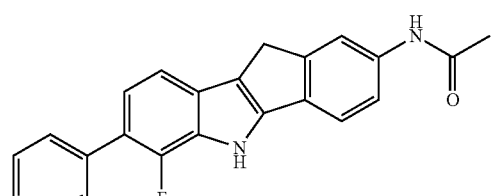
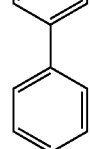
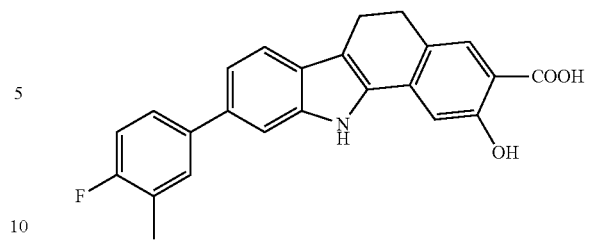
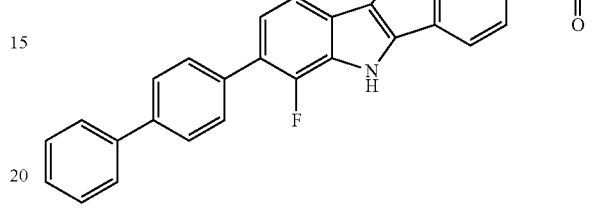
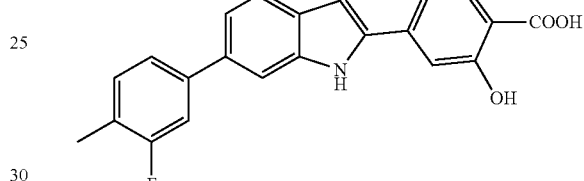
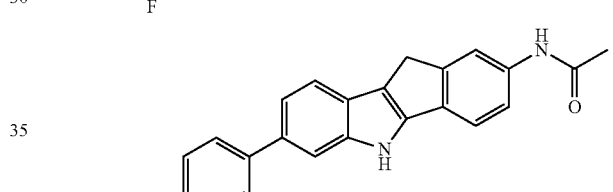
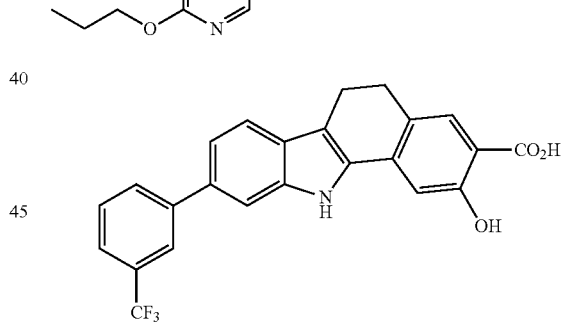
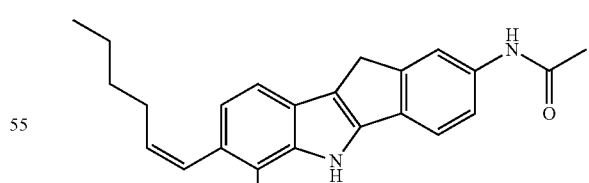
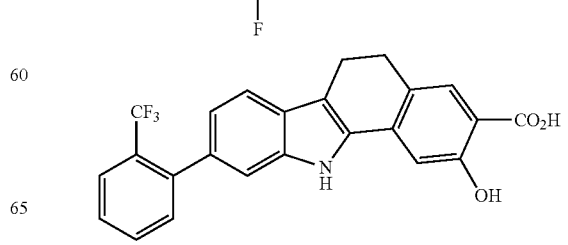

97
-continued
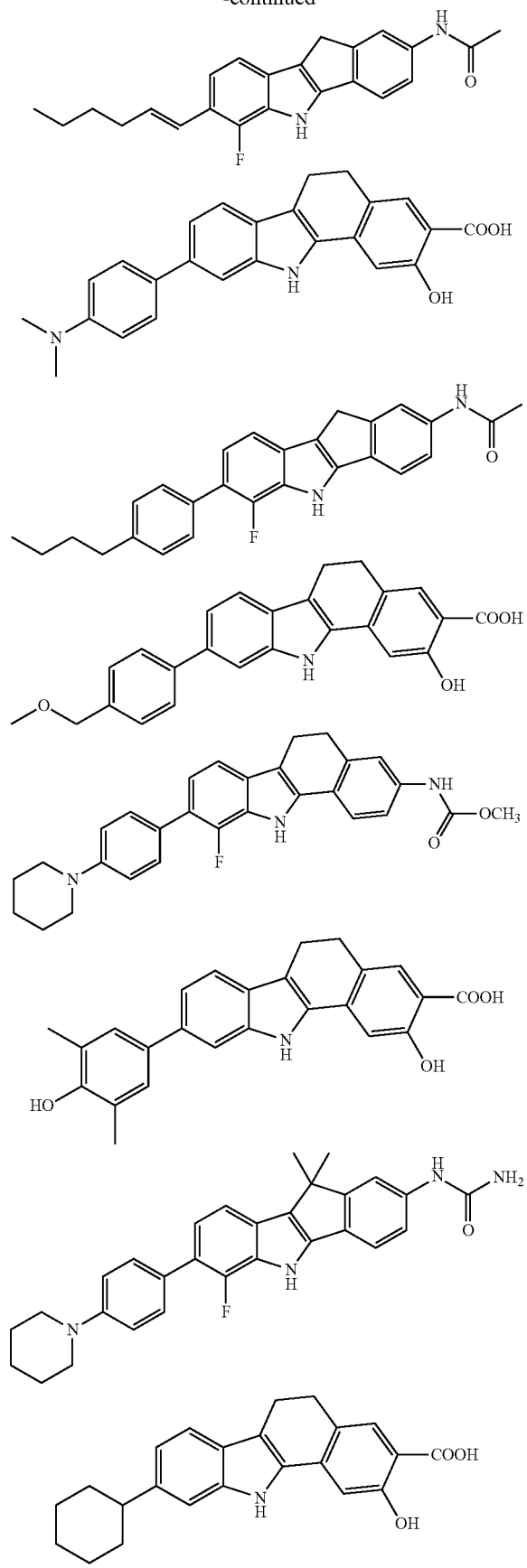
98
-continued
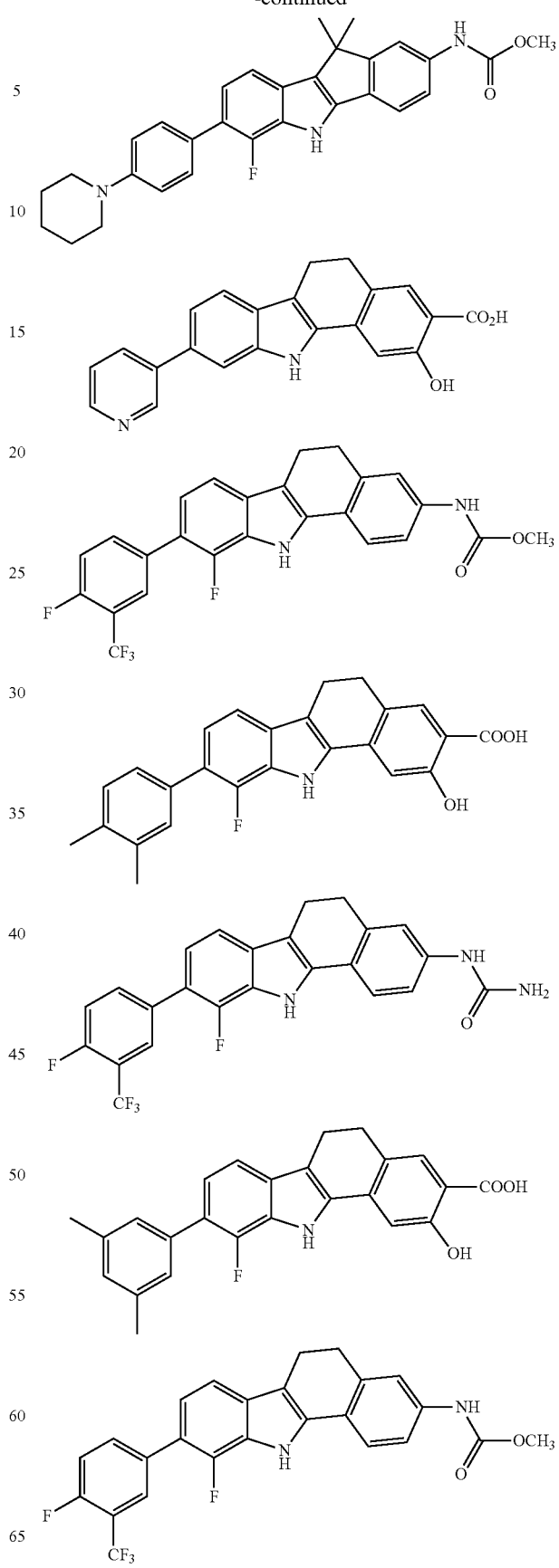

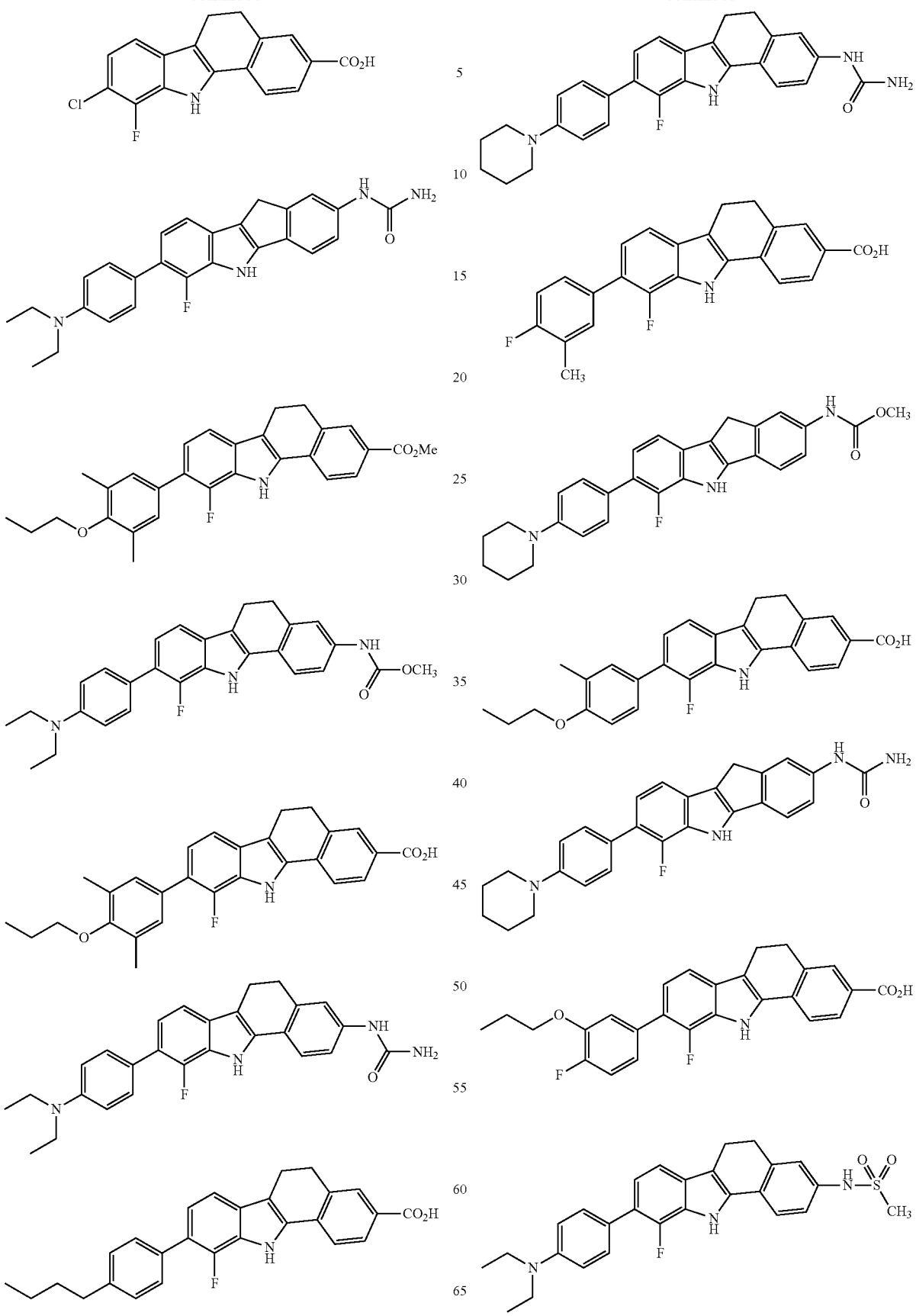

101
-continued
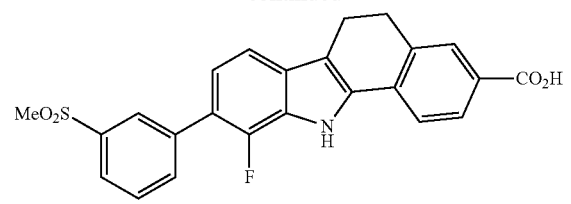
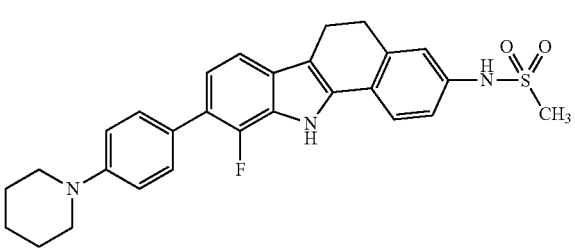
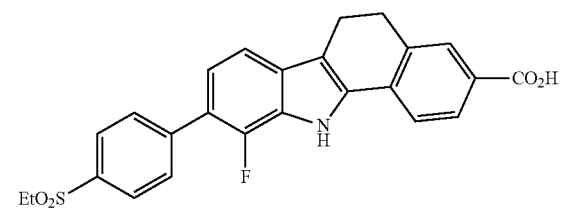
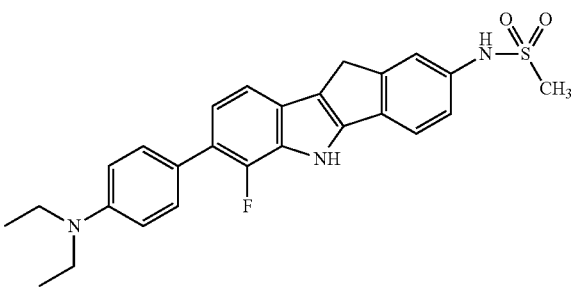
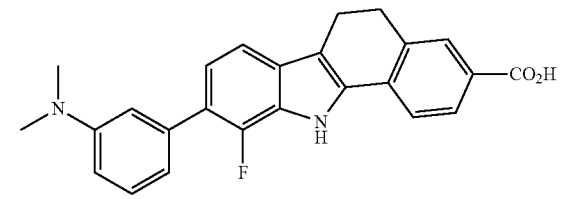
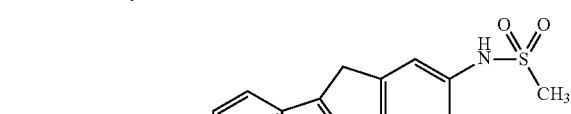
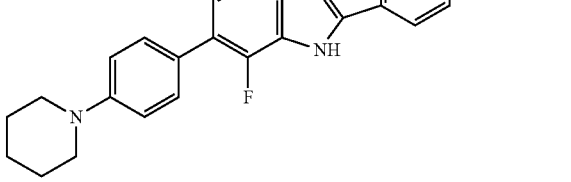
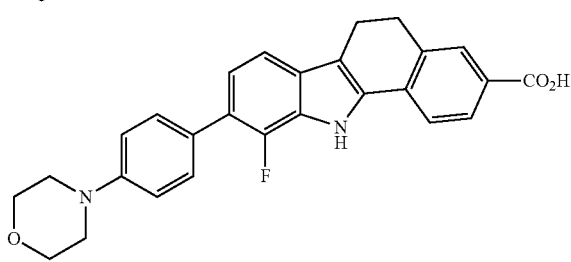
102
-continued
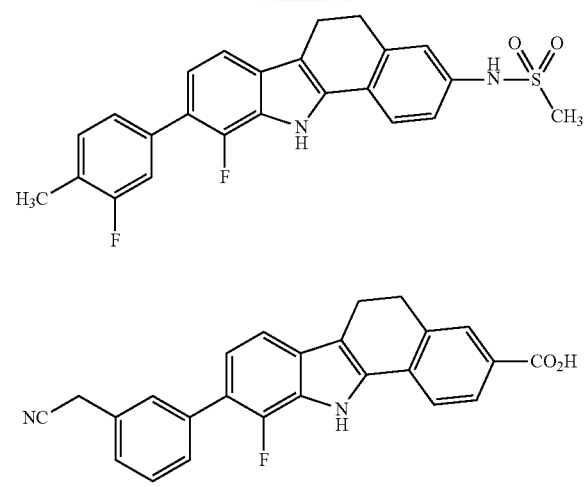
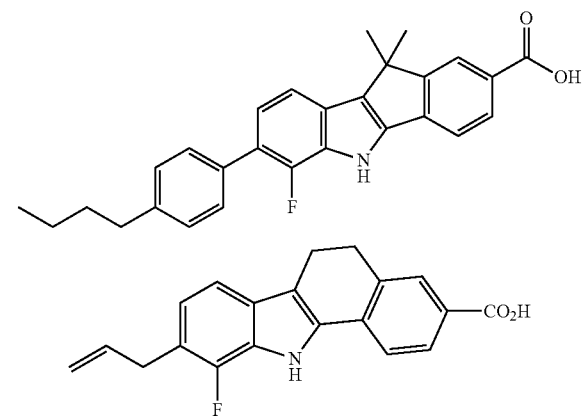
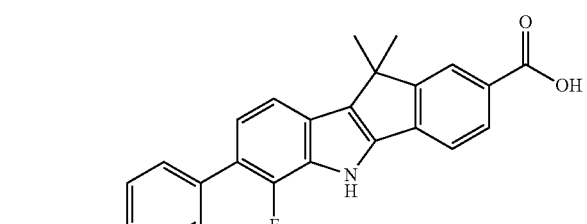
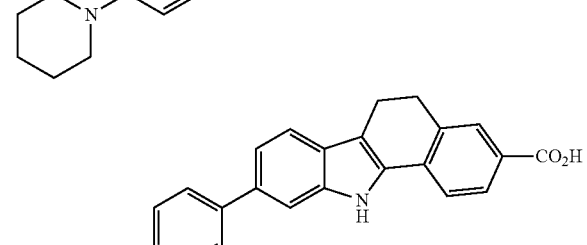
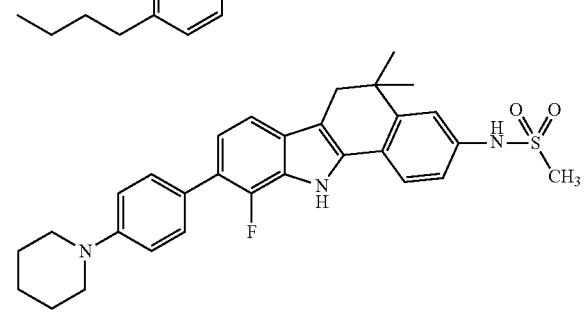

103
-continued
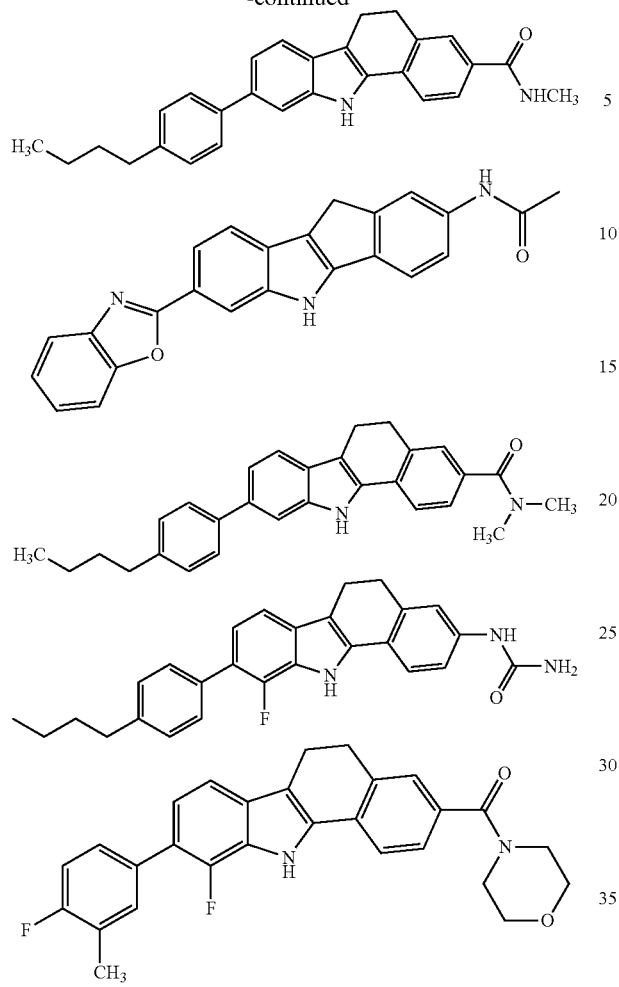
104
-continued
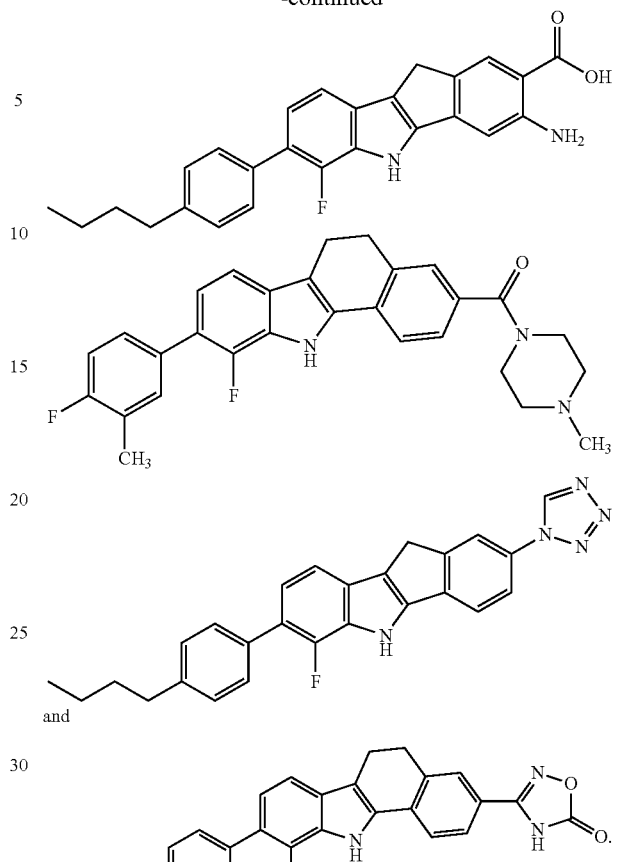
* * * * *